(12) United States Patent
Tamura et al.

(10) Patent No.: US 7,708,999 B2
(45) Date of Patent: May 4, 2010

(54) REMEDIES FOR ARTHRITIS

(75) Inventors: Tadafumi Tamura, Shizuoka (JP); Masako Uchii, Mishima (JP); Toshio Suda, Fukuoka (JP); Ichiro Miki, Mishima (JP); Akira Tanaka, Tochigi (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 724 days.

(21) Appl. No.: 10/500,207

(22) PCT Filed: Dec. 26, 2002

(86) PCT No.: PCT/JP02/13650

§ 371 (c)(1),
(2), (4) Date: Jan. 4, 2005

(87) PCT Pub. No.: WO03/057251

PCT Pub. Date: Jul. 17, 2003

(65) Prior Publication Data

US 2005/0175608 A1 Aug. 11, 2005

(30) Foreign Application Priority Data

Dec. 28, 2001 (JP) .............................. 2001-400677

(51) Int. Cl.
*A61K 39/395* (2006.01)
*A61K 39/00* (2006.01)

(52) U.S. Cl. .............. 424/145.1; 424/130.1; 424/133.1; 424/141.1

(58) Field of Classification Search ........................ None
See application file for complete search history.

(56) References Cited

U.S. PATENT DOCUMENTS 5,491,220 A * 2/1996 Seddon et al. ............... 530/399
5,952,472 A * 9/1999 Hanai et al. ............... 530/387.1
6,037,329 A * 3/2000 Baird et al. .................... 514/44

FOREIGN PATENT DOCUMENTS

| EP | 799835 A2 | 10/1997 |
|---|---|---|
| EP | 0799835 A2 | 10/1997 |
| EP | 0 882 794 A2 | 12/1998 |
| EP | 0882794 A2 | 12/1998 |
| EP | 882794 A2 | 12/1998 |
| JP | 2001-46066 | 2/2001 |
| JP | 2001-46066 A | 2/2001 |
| WO | 00/62809 A1 | 10/2000 |
| WO | WO00/62809 | 10/2000 |
| WO | 03/002608 A1 | 1/2003 |

OTHER PUBLICATIONS

Owen et al. Journal of Immunological Methods, 1994, 168:149-165.*
The Merck Manuals Online Medical Library, [online]. Whitehouse Station, NJ: Merck Research Laboratories, 2006-2007. [retrieved on Oct. 10, 2007]. Retrieved from the Internet: < URL:http://www.merck.com/mmpe/print/sec04/ch034/ch034b.html>. Rheumatoid Arthritis (RA), see pp. 1-9.*
Rader et al. PNAS. 1998. 95:8910-8915.*
Rudikoff et al. PNAS 1982 vol. 79, pp. 1979-1983.*
Supplementary European Search Report issued in connection with EP 02 79 2021 dated Mar. 22, 2006.
Kurihara et al; "Cooperation of Endothelin-1 and FGF8 in Meckel's Cartilage Formation"; Development Growth & Differentiation, Jun. 2001, vol. 43.
Praul et al; Effect of Fibroblast Growth Factors, 1, 2, 4, 5, 6, 7, 8, 9 and 10 on Avian Chondrocyte Proliferation, Journal of Cellular Biochemistry, Oct. 2001, vol. 84, No. 2, pp. 359-366.

* cited by examiner

*Primary Examiner*—Phillip Gambel
*Assistant Examiner*—Sharon Wen
(74) *Attorney, Agent, or Firm*—Nixon & Vanderhye, P.C.

(57) ABSTRACT

The invention provides an agent for preventing or treating arthritis, a cartilage protecting agent, a joint destruction inhibitor and a synovial membrane growth inhibitor comprising an anti-FGF-8 neutralizing antibody as an active ingredient, as well as a diagnostic agent of arthritis comprising an anti-FGF-8 antibody as an active ingredient and a method for judging arthritis using the antibody.

4 Claims, 34 Drawing Sheets

```
SEQUENCE LISTING

<160> NUMBER OF SEQ ID NOS: 51

<210> SEQ ID NO 1
<211> LENGTH: 420
<212> TYPE: DNA
<213> ORGANISM: Mus musculus
<220> FEATURE:
<221> NAME/KEY: source
<222> LOCATION: (1)..(420)
<223> OTHER INFORMATION: /organism="Mus musculus"
<220> FEATURE:
<221> NAME/KEY: CDS
<222> LOCATION: (1)..(420)
<220> FEATURE:
<221> NAME/KEY: sig_peptide
<222> LOCATION: (1)..(57)

<400> SEQUENCE: 1 atg gaa tgg atc tgg atc ttt ctc ttc ttc ctc tca gga act aca ggt    48
Met Glu Trp Ile Trp Ile Phe Leu Phe Phe Leu Ser Gly Thr Thr Gly
```

```
                 1               5              10              15
gtc tac tcc cag gtt cag ctg cag cag tct gga gct gag gtg gcg agg        96
Val Tyr Ser Gln Val Gln Leu Gln Gln Ser Gly Ala Glu Val Ala Arg
                20              25              30 ccc ggg gct tca gtg aaa ctg tcc tgc aag gct tct ggc tac acc ttc       144
Pro Gly Ala Ser Val Lys Leu Ser Cys Lys Ala Ser Gly Tyr Thr Phe
            35              40              45 act gac tac tat cta aac tgg gtg aag cag agg tct gga cag ggc ctt       192
Thr Asp Tyr Tyr Leu Asn Trp Val Lys Gln Arg Ser Gly Gln Gly Leu
         50              55              60 gag tgg att gga gag att gat cct gga agt gat agt ata tat tat aat       240
Glu Trp Ile Gly Glu Ile Asp Pro Gly Ser Asp Ser Ile Tyr Tyr Asn
 65              70              75              80 gaa aac ttg gag ggc agg gcc aca ctg act gca gac aaa tcc tcc agc       288
Glu Asn Leu Glu Gly Arg Ala Thr Leu Thr Ala Asp Lys Ser Ser Ser
                85              90              95 aca gcc tac atg cag ctc aac agc ctg aca tct gag gac tct gca gtc       336
Thr Ala Tyr Met Gln Leu Asn Ser Leu Thr Ser Glu Asp Ser Ala Val
            100             105             110 tat ttc tgt gca aga tat ggg tat tct aga tac gac gta agg ttt gtc       384
Tyr Phe Cys Ala Arg Tyr Gly Tyr Ser Arg Tyr Asp Val Arg Phe Val
        115             120             125 tac tgg ggc caa ggg act ctg gtc act gtc tct aca                       420
Tyr Trp Gly Gln Gly Thr Leu Val Thr Val Ser Thr
    130             135             140

<210> SEQ ID NO 2
<211> LENGTH: 140
<212> TYPE: PRT
<213> ORGANISM: Mus musculus
<220> FEATURE:
<221> NAME/KEY: SIGNAL
<222> LOCATION: (1)..(19)

<400> SEQUENCE: 2

Met Glu Trp Ile Trp Ile Phe Leu Phe Phe Leu Ser Gly Thr Thr Gly
 1               5                  10                  15

Val Tyr Ser Gln Val Gln Leu Gln Gln Ser Gly Ala Glu Val Ala Arg
                20                  25                  30

Pro Gly Ala Ser Val Lys Leu Ser Cys Lys Ala Ser Gly Tyr Thr Phe
            35                  40                  45

Thr Asp Tyr Tyr Leu Asn Trp Val Lys Gln Arg Ser Gly Gln Gly Leu
        50                  55                  60

Glu Trp Ile Gly Glu Ile Asp Pro Gly Ser Asp Ser Ile Tyr Tyr Asn
 65                 70                  75                  80

Glu Asn Leu Glu Gly Arg Ala Thr Leu Thr Ala Asp Lys Ser Ser Ser
                85                  90                  95

Thr Ala Tyr Met Gln Leu Asn Ser Leu Thr Ser Glu Asp Ser Ala Val
            100                 105                 110

Tyr Phe Cys Ala Arg Tyr Gly Tyr Ser Arg Tyr Asp Val Arg Phe Val
        115                 120                 125

Tyr Trp Gly Gln Gly Thr Leu Val Thr Val Ser Thr
    130                 135                 140

<210> SEQ ID NO 3
<211> LENGTH: 393
<212> TYPE: DNA
<213> ORGANISM: Mus musculus
<220> FEATURE:
<221> NAME/KEY: source
```

<222> LOCATION: (1)..(393)
<223> OTHER INFORMATION: /organism="Mus musculus"
<220> FEATURE:
<221> NAME/KEY: CDS
<222> LOCATION: (1)..(393)
<220> FEATURE:
<221> NAME/KEY: sig_peptide
<222> LOCATION: (1)..(57)

<400> SEQUENCE: 3

```
atg aag ttg cct gtt agg ctg ttg gtg ctg atg ttc tgg att cct gct        48
Met Lys Leu Pro Val Arg Leu Leu Val Leu Met Phe Trp Ile Pro Ala
 1               5                  10                  15 tcc agg agt gat gtt ttg atg acc caa act cca ctc tcc ctg cct gtc        96
Ser Arg Ser Asp Val Leu Met Thr Gln Thr Pro Leu Ser Leu Pro Val
             20                  25                  30 agt ctt gga gat caa gcc tcc atc tct tgc aga tct agt cag agt ctt       144
Ser Leu Gly Asp Gln Ala Ser Ile Ser Cys Arg Ser Ser Gln Ser Leu
         35                  40                  45 gta cat agt aat gga aga acc tat tta gaa tgg tac ctg cag aaa cct       192
Val His Ser Asn Gly Arg Thr Tyr Leu Glu Trp Tyr Leu Gln Lys Pro
     50                  55                  60 ggc cag tca cca aag gtc ctg atc tac aaa gtt tcc aac cga att tct       240
Gly Gln Ser Pro Lys Val Leu Ile Tyr Lys Val Ser Asn Arg Ile Ser
 65                  70                  75                  80 ggg gtc cca gac agg ttc agt ggc agt gga tca ggg aca gat ttc aca       288
Gly Val Pro Asp Arg Phe Ser Gly Ser Gly Ser Gly Thr Asp Phe Thr
                 85                  90                  95 ctc aaa atc agc aga gtg gag gct gag gat ctg gga gtt tat ttc tgc       336
Leu Lys Ile Ser Arg Val Glu Ala Glu Asp Leu Gly Val Tyr Phe Cys
            100                 105                 110 ttt cag ggt tca cat gtt ccg tac acg ttc gga ggg ggg acc aag ctg       384
Phe Gln Gly Ser His Val Pro Tyr Thr Phe Gly Gly Gly Thr Lys Leu
        115                 120                 125 gaa ata aaa                                                            393
Glu Ile Lys
    130
```

<210> SEQ ID NO 4
<211> LENGTH: 131
<212> TYPE: PRT
<213> ORGANISM: Mus musculus
<220> FEATURE:
<221> NAME/KEY: SIGNAL
<222> LOCATION: (1)..(19)

<400> SEQUENCE: 4

```
Met Lys Leu Pro Val Arg Leu Leu Val Leu Met Phe Trp Ile Pro Ala
 1               5                  10                  15

Ser Arg Ser Asp Val Leu Met Thr Gln Thr Pro Leu Ser Leu Pro Val
             20                  25                  30

Ser Leu Gly Asp Gln Ala Ser Ile Ser Cys Arg Ser Ser Gln Ser Leu
         35                  40                  45

Val His Ser Asn Gly Arg Thr Tyr Leu Glu Trp Tyr Leu Gln Lys Pro
     50                  55                  60

Gly Gln Ser Pro Lys Val Leu Ile Tyr Lys Val Ser Asn Arg Ile Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Phe Cys
            100                 105                 110
```

```
Phe Gln Gly Ser His Val Pro Tyr Thr Phe Gly Gly Thr Lys Leu
        115                 120                 125

Glu Ile Lys
        130

<210> SEQ ID NO 5
<211> LENGTH: 121
<212> TYPE: PRT
<213> ORGANISM: Mus musculus

<400> SEQUENCE: 5

Gln Val Gln Leu Gln Gln Ser Gly Ala Glu Val Ala Arg Pro Gly Ala
  1               5                  10                  15

Ser Val Lys Leu Ser Cys Lys Ala Ser Gly Tyr Thr Phe Thr Asp Tyr
             20                  25                  30

Tyr Leu Asn Trp Val Lys Gln Arg Ser Gly Gln Gly Leu Glu Trp Ile
         35                  40                  45

Gly Glu Ile Asp Pro Gly Ser Asp Ser Ile Tyr Tyr Asn Glu Asn Leu
     50                  55                  60

Glu Gly Arg Ala Thr Leu Thr Ala Asp Lys Ser Ser Ser Thr Ala Tyr
 65                  70                  75                  80

Met Gln Leu Asn Ser Leu Thr Ser Glu Asp Ser Ala Val Tyr Phe Cys
                 85                  90                  95

Ala Arg Tyr Gly Tyr Ser Arg Tyr Asp Val Arg Phe Val Tyr Trp Gly
            100                 105                 110

Gln Gly Thr Leu Val Thr Val Ser Thr
        115                 120

<210> SEQ ID NO 6
<211> LENGTH: 112
<212> TYPE: PRT
<213> ORGANISM: Mus musculus

<400> SEQUENCE: 6

Asp Val Leu Met Thr Gln Thr Pro Leu Ser Leu Pro Val Ser Leu Gly
  1               5                  10                  15

Asp Gln Ala Ser Ile Ser Cys Arg Ser Ser Gln Ser Leu Val His Ser
             20                  25                  30

Asn Gly Arg Thr Tyr Leu Glu Trp Tyr Leu Gln Lys Pro Gly Gln Ser
         35                  40                  45

Pro Lys Val Leu Ile Tyr Lys Val Ser Asn Arg Ile Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Phe Gln Gly
                 85                  90                  95

Ser His Val Pro Tyr Thr Phe Gly Gly Thr Lys Leu Glu Ile Lys
            100                 105                 110

<210> SEQ ID NO 7
<211> LENGTH: 5
<212> TYPE: PRT
<213> ORGANISM: Mus musculus

<400> SEQUENCE: 7

Asp Tyr Tyr Leu Asn
  1               5
```

<210> SEQ ID NO 8
<211> LENGTH: 17
<212> TYPE: PRT
<213> ORGANISM: Mus musculus

<400> SEQUENCE: 8

Glu Ile Asp Pro Gly Ser Asp Ser Ile Tyr Tyr Asn Glu Asn Leu Glu
 1               5                  10                  15
Gly

<210> SEQ ID NO 9
<211> LENGTH: 12
<212> TYPE: PRT
<213> ORGANISM: Mus musculus

<400> SEQUENCE: 9

Tyr Gly Tyr Ser Arg Tyr Asp Val Arg Phe Val Tyr
 1               5                  10

<210> SEQ ID NO 10
<211> LENGTH: 16
<212> TYPE: PRT
<213> ORGANISM: Mus musculus

<400> SEQUENCE: 10

Arg Ser Ser Gln Ser Leu Val His Ser Asn Gly Arg Thr Tyr Leu Glu
 1               5                  10                  15

<210> SEQ ID NO 11
<211> LENGTH: 7
<212> TYPE: PRT
<213> ORGANISM: Mus musculus

<400> SEQUENCE: 11

Lys Val Ser Asn Arg Ile Ser
 1               5

<210> SEQ ID NO 12
<211> LENGTH: 9
<212> TYPE: PRT
<213> ORGANISM: Mus musculus

<400> SEQUENCE: 12

Phe Gln Gly Ser His Val Pro Tyr Thr
 1               5

<210> SEQ ID NO 13
<211> LENGTH: 22
<212> TYPE: DNA
<213> ORGANISM: Artificial Sequence
<220> FEATURE:
<223> OTHER INFORMATION: a primer for amplification of KM1334 VH

<400> SEQUENCE: 13
ctgaattcgc ggccgctagt cc                                      22

<210> SEQ ID NO 14
<211> LENGTH: 39
<212> TYPE: DNA
<213> ORGANISM: Artificial Sequence
<220> FEATURE:
<223> OTHER INFORMATION: a primer for amplification of KM1334 VH

<400> SEQUENCE: 14
atgggccctt ggtggaggct gtagagacag tgaccagag                    39

<210> SEQ ID NO 15
<211> LENGTH: 22
<212> TYPE: DNA
<213> ORGANISM: Artificial Sequence
<220> FEATURE:
<223> OTHER INFORMATION: a primer for amplification of KM1334 VL

<400> SEQUENCE: 15
ctgaattcgc ggccgctgct gt                                              22

<210> SEQ ID NO 16
<211> LENGTH: 28
<212> TYPE: DNA
<213> ORGANISM: Artificial Sequence
<220> FEATURE:
<223> OTHER INFORMATION: a primer for amplification of KM1334 VL

<400> SEQUENCE: 16
atcgtacgtt ttatttccag cttggtcc                                        28

<210> SEQ ID NO 17
<211> LENGTH: 25
<212> TYPE: PRT
<213> ORGANISM: Artificial Sequence
<220> FEATURE:
<223> OTHER INFORMATION: human FGF-8 peptide (amino acid residues 23-46)
      added an cystein residue at its C-terminus

<400> SEQUENCE: 17

Gln Val Thr Val Gln Ser Ser Pro Asn Phe Thr Gln His Val Arg Glu
 1               5                  10                  15

Gln Ser Leu Val Thr Asp Gln Leu Cys
             20                  25

<210> SEQ ID NO 18
<211> LENGTH: 121
<212> TYPE: PRT
<213> ORGANISM: Artificial Sequence
<220> FEATURE:
<223> OTHER INFORMATION: HV.0, a designed amino acid sequence of VH of
      an anti-FGF-8 CDR-grafted neutralizing antibody

<400> SEQUENCE: 18

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
             20                  25                  30

Tyr Leu Asn Trp Val Arg Gln Ala Pro Gly Gln Gly Leu Glu Trp Met
         35                  40                  45

Gly Glu Ile Asp Pro Gly Ser Asp Ser Ile Tyr Tyr Asn Glu Asn Leu
     50                  55                  60

Glu Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Gly Tyr Ser Arg Tyr Asp Val Arg Phe Val Tyr Trp Gly
            100                 105                 110

Gln Gly Thr Leu Val Thr Val Ser Ser
        115                 120

<210> SEQ ID NO 19

```
<211> LENGTH: 112
<212> TYPE: PRT
<213> ORGANISM: Artificial Sequence
<220> FEATURE:
<223> OTHER INFORMATION: LV.0, a designed amino acid sequence of VL of
      an anti-FGF-8 CDR-grafted neutralizing antibody

<400> SEQUENCE: 19

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Arg Thr Tyr Leu Glu Trp Tyr Leu Gln Lys Pro Gly Gln Ser
        35                  40                  45

Pro Gln Leu Leu Ile Tyr Lys Val Ser Asn Arg Ile Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Val Glu Ile Lys
            100                 105                 110

<210> SEQ ID NO 20
<211> LENGTH: 121
<212> TYPE: PRT
<213> ORGANISM: Artificial Sequence
<220> FEATURE:
<223> OTHER INFORMATION: HV.6, a designed amino acid sequence of VH of
      an anti-FGF-8 CDR-grafted neutralizing antibody

<400> SEQUENCE: 20

Gln Val Gln Leu Val Gln Ser Gly Ala Glu Val Ala Arg Pro Gly Ala
1               5                   10                  15

Ser Val Lys Val Ser Cys Lys Ala Ser Gly Tyr Thr Phe Thr Asp Tyr
            20                  25                  30

Tyr Leu Asn Trp Val Arg Gln Arg Ser Gly Gln Gly Leu Glu Trp Ile
        35                  40                  45

Gly Glu Ile Asp Pro Gly Ser Asp Ser Ile Tyr Tyr Asn Glu Asn Leu
    50                  55                  60

Glu Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Tyr Gly Tyr Ser Arg Tyr Asp Val Arg Phe Val Tyr Trp Gly
            100                 105                 110

Gln Gly Thr Leu Val Thr Val Ser Ser
        115                 120

<210> SEQ ID NO 21
<211> LENGTH: 112
<212> TYPE: PRT
<213> ORGANISM: Artificial Sequence
<220> FEATURE:
<223> OTHER INFORMATION: LV.6, a designed amino acid sequence of VL of
      an anti-FGF-8 CDR-grafted neutralizing antibody

<400> SEQUENCE: 21

Asp Val Val Met Thr Gln Ser Pro Leu Ser Leu Pro Val Ser Leu Gly
1               5                   10                  15
```

```
Glu Pro Ala Ser Ile Ser Cys Arg Ser Ser Gln Ser Leu Val His Ser
            20                  25                  30

Asn Gly Arg Thr Tyr Leu Glu Trp Tyr Leu Gln Lys Pro Gly Gln Ser
        35                  40                  45

Pro Lys Val Leu Ile Tyr Lys Val Ser Asn Arg Ile Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Ser His Val Pro Tyr Thr Phe Gly Gln Gly Thr Lys Val Glu Ile Lys
            100                 105                 110

<210> SEQ ID NO 22
<211> LENGTH: 504
<212> TYPE: DNA
<213> ORGANISM: Artificial Sequence
<220> FEATURE:
<223> OTHER INFORMATION: a DNA encoding HV.0
<220> FEATURE:
<221> NAME/KEY: CDS
<222> LOCATION: (47)..(466)
<220> FEATURE:
<221> NAME/KEY: sig_peptide
<222> LOCATION: (47)..(103)

<400> SEQUENCE: 22
caggaaacag ctatgacgaa ttcgcggccg cacactgact ctaacc atg gaa tgg      55
                                                   Met Glu Trp atc tgg atc ttt ctc ttc ttc ctc tca gga act aca ggt gtc tac tcc    103
Ile Trp Ile Phe Leu Phe Phe Leu Ser Gly Thr Thr Gly Val Tyr Ser
    -15                 -10                 -5                  -1 cag gtg cag ctg gtg cag tct ggg gct gag gtg aag aag ccc ggg gcc    151
Gln Val Gln Leu Val Gln Ser Gly Ala Glu Val Lys Lys Pro Gly Ala
1               5                   10                  15 tca gtg aag gtc tcc tgc aag gct tct gga tac acc ttc act gac tac    199
Ser Val Lys Val Ser Cys Lys Ala Ser Gly Tyr Thr Phe Thr Asp Tyr
                20                  25                  30 tat cta aac tgg gtg cgg cag gcc ccc gga caa ggg ctt gag tgg atg    247
Tyr Leu Asn Trp Val Arg Gln Ala Pro Gly Gln Gly Leu Glu Trp Met
        35                  40                  45 gga gag atc gat cct gga agt gat agt ata tat tat aat gaa aac ttg    295
Gly Glu Ile Asp Pro Gly Ser Asp Ser Ile Tyr Tyr Asn Glu Asn Leu
    50                  55                  60 gag ggc aga gtc acg att acc gcg gac aca tcc acg agc aca gcc tac    343
Glu Gly Arg Val Thr Ile Thr Ala Asp Thr Ser Thr Ser Thr Ala Tyr
65                  70                  75                  80 atg gag ctg agc agc ctg aga tct gag gac acg gcc gtg tat tac tgt    391
Met Glu Leu Ser Ser Leu Arg Ser Glu Asp Thr Ala Val Tyr Tyr Cys
                85                  90                  95 gcg aga tat ggg tat tct aga tac gac gta agg ttt gtc tac tgg ggc    439
Ala Arg Tyr Gly Tyr Ser Arg Tyr Asp Val Arg Phe Val Tyr Trp Gly
            100                 105                 110 cag gga acc ctg gtc acc gtc tcc tca gcctccacca agggcccact          486
Gln Gly Thr Leu Val Thr Val Ser Ser
                115                 120 agtcgtgact gggaaaac                                                504

<210> SEQ ID NO 23
<211> LENGTH: 141
<212> TYPE: DNA
```

<213> ORGANISM: Artificial Sequence
<220> FEATURE:
<223> OTHER INFORMATION: a synthetic DNA for construction of a DNA encoding HV.0

<400> SEQUENCE: 23
caggaaacag ctatgacgaa ttcgcggccg cacactgact ctaaccatgg aatggatctg    60
gatctttctc ttcttcctct caggaactac aggtgtctac tcccaggtgc agctggtgca   120
gtctggggct gaggtgaaga a                                              141

<210> SEQ ID NO 24
<211> LENGTH: 141
<212> TYPE: DNA
<213> ORGANISM: Artificial Sequence
<220> FEATURE:
<223> OTHER INFORMATION: a synthetic DNA for construction of a DNA encoding HV.0

<400> SEQUENCE: 24
aggatcgatc tctcccatcc actcaagccc ttgtccgggg gcctgccgca cccagtttag    60
atagtagtca gtgaaggtgt atccagaagc cttgcaggag accttcactg aggccccggg   120
cttcttcacc tcagccccag a                                              141

<210> SEQ ID NO 25
<211> LENGTH: 141
<212> TYPE: DNA
<213> ORGANISM: Artificial Sequence
<220> FEATURE:
<223> OTHER INFORMATION: a synthetic DNA for construction of a DNA encoding HV.0

<400> SEQUENCE: 25
ggatgggaga gatcgatcct ggaagtgata gtatatatta taatgaaaac ttggagggca    60
gagtcacgat taccgcggac acatccacga gcacagccta catggagctg agcagcctga   120
gatctgagga cacggccgtg t                                              141

<210> SEQ ID NO 26
<211> LENGTH: 141
<212> TYPE: DNA
<213> ORGANISM: Artificial Sequence
<220> FEATURE:
<223> OTHER INFORMATION: a synthetic DNA for construction of a DNA encoding HV.0

<400> SEQUENCE: 26
gttttcccag tcacgactag tgggcccttg gtggaggctg aggagacggt gaccagggtt    60
ccctggcccc agtagacaaa ccttacgtcg tatctagaat acccatatct cgcacagtaa   120
tacacggccg tgtcctcaga t                                              141

<210> SEQ ID NO 27
<211> LENGTH: 504
<212> TYPE: DNA
<213> ORGANISM: Artificial Sequence
<220> FEATURE:
<223> OTHER INFORMATION: a DNA encoding HV.6
<220> FEATURE:
<221> NAME/KEY: CDS
<222> LOCATION: (47)..(466)
<220> FEATURE:
<221> NAME/KEY: sig_peptide
<222> LOCATION: (47)..(103)

<400> SEQUENCE: 27

-continued

```
caggaaacag ctatgacgaa ttcgcggccg cacactgact ctaacc atg gaa tgg        55
                                                   Met Glu Trp atc tgg atc ttt ctc ttc ttc ctc tca gga act aca ggt gtc tac tcc       103
Ile Trp Ile Phe Leu Phe Phe Leu Ser Gly Thr Thr Gly Val Tyr Ser
    -15             -10                 -5                  -1 cag gtg cag ctg gtg cag tct ggg gct gag gtg gcg agg ccc ggg gcc       151
Gln Val Gln Leu Val Gln Ser Gly Ala Glu Val Ala Arg Pro Gly Ala
 1               5                  10                  15 tca gtg aag gtc tcc tgc aag gct tct gga tac acc ttc act gac tac       199
Ser Val Lys Val Ser Cys Lys Ala Ser Gly Tyr Thr Phe Thr Asp Tyr
             20                  25                  30 tat cta aac tgg gtg cgg cag agg tct gga caa ggg ctt gag tgg att       247
Tyr Leu Asn Trp Val Arg Gln Arg Ser Gly Gln Gly Leu Glu Trp Ile
         35                  40                  45 gga gag atc gat cct gga agt gat agt ata tat tat aat gaa aac ttg       295
Gly Glu Ile Asp Pro Gly Ser Asp Ser Ile Tyr Tyr Asn Glu Asn Leu
 50                  55                  60 gag ggc aga gtc acg att acc gcg gac aca tcc acg agc aca gcc tac       343
Glu Gly Arg Val Thr Ile Thr Ala Asp Thr Ser Thr Ser Thr Ala Tyr
 65                  70                  75                  80 atg gag ctg agc agc ctg aga tct gag gac acg gcc gtg tat ttc tgt       391
Met Glu Leu Ser Ser Leu Arg Ser Glu Asp Thr Ala Val Tyr Phe Cys
                 85                  90                  95 gcg aga tat ggg tat tct aga tac gac gta agg ttt gtc tac tgg ggc       439
Ala Arg Tyr Gly Tyr Ser Arg Tyr Asp Val Arg Phe Val Tyr Trp Gly
                100                 105                 110 cag gga acc ctg gtc acc gtc tcc tca    gcctccacca agggcccact          486
Gln Gly Thr Leu Val Thr Val Ser Ser
                115                 120 agtcgtgact gggaaaac                                                   504

<210> SEQ ID NO 28
<211> LENGTH: 141
<212> TYPE: DNA
<213> ORGANISM: Artificial Sequence
<220> FEATURE:
<223> OTHER INFORMATION: a synthetic DNA for construction of a DNA
      encoding HV.6

<400> SEQUENCE: 28
caggaaacag ctatgacgaa ttcgcggccg cacactgact ctaaccatgg aatggatctg     60
gatctttctc ttcttcctct caggaactac aggtgtctac tcccaggtgc agctggtgca    120
gtctggggct gaggtggcga g                                              141

<210> SEQ ID NO 29
<211> LENGTH: 141
<212> TYPE: DNA
<213> ORGANISM: Artificial Sequence
<220> FEATURE:
<223> OTHER INFORMATION: a synthetic DNA for construction of a DNA
      encoding HV.6

<400> SEQUENCE: 29
aggatcgatc tctccaatcc actcaagccc ttgtccagac ctctgccgca cccagtttag     60
atagtagtca gtgaaggtgt atccagaagc cttgcaggag accttcactg aggccccggg    120
cctcgccacc tcagccccag a                                              141

<210> SEQ ID NO 30
<211> LENGTH: 141
```

```
<212> TYPE: DNA
<213> ORGANISM: Artificial Sequence
<220> FEATURE:
<223> OTHER INFORMATION: a synthetic DNA for construction of a DNA
      encoding HV.6

<400> SEQUENCE: 30
ggattggaga gatcgatcct ggaagtgata gtatatatta taatgaaaac ttggagggca      60
gagtcacgat taccgcggac acatccacga gcacagccta catggagctg agcagcctga     120
gatctgagga cacggccgtg t                                                141

<210> SEQ ID NO 31
<211> LENGTH: 141
<212> TYPE: DNA
<213> ORGANISM: Artificial Sequence
<220> FEATURE:
<223> OTHER INFORMATION: a synthetic DNA for construction of a DNA
      encoding HV.6

<400> SEQUENCE: 31
gttttcccag tcacgactag tgggcccttg gtggaggctg aggagacggt gaccagggtt      60
ccctggcccc agtagacaaa ccttacgtcg tatctagaat acccatatct cgcacagaaa     120
tacacggccg tgtcctcaga t                                                141

<210> SEQ ID NO 32
<211> LENGTH: 459
<212> TYPE: DNA
<213> ORGANISM: Artificial Sequence
<220> FEATURE:
<223> OTHER INFORMATION: a DNA encoding LV.0
<220> FEATURE:
<221> NAME/KEY: CDS
<222> LOCATION: (40)..(432)
<220> FEATURE:
<221> NAME/KEY: sig_peptide
<222> LOCATION: (40)..(96)

<400> SEQUENCE: 32
caggaaacag ctatgacgaa ttcaggttgc ctcctcaaa atg aag ttg cct gtt          54
                                            Met Lys Leu Pro Val
                                                            -15 agg ctg ttg gtg ctg atg ttc tgg att cct gct tcc agg agt gat atc       102
Arg Leu Leu Val Leu Met Phe Trp Ile Pro Ala Ser Arg Ser Asp Ile
            -10                 -5                  -1  1 gtg atg act cag tct cca ctc tcc ctg ccc gtc acc cct gga gag ccg       150
Val Met Thr Gln Ser Pro Leu Ser Leu Pro Val Thr Pro Gly Glu Pro
         5                 10                  15 gcc tcc atc tcc tgc aga tct agt cag agt ctt gta cat agt aat gga       198
Ala Ser Ile Ser Cys Arg Ser Ser Gln Ser Leu Val His Ser Asn Gly
     20                  25                  30 aga acc tat tta gaa tgg tac ctg cag aag cca ggc cag tct cca cag       246
Arg Thr Tyr Leu Glu Trp Tyr Leu Gln Lys Pro Gly Gln Ser Pro Gln
 35                  40                  45                  50 ctc ctg atc tat aaa gtt tcc aac cga att tct ggg gtc cca gac agg       294
Leu Leu Ile Tyr Lys Val Ser Asn Arg Ile Ser Gly Val Pro Asp Arg
                 55                  60                  65 ttc agt ggc agt gga tcc ggg aca gat ttc aca ctg aaa atc agc agg       342
Phe Ser Gly Ser Gly Ser Gly Thr Asp Phe Thr Leu Lys Ile Ser Arg
             70                  75                  80 gtg gag gct gag gac gtc ggg gtt tat tac tgc ttt cag ggt tca cat       390
Val Glu Ala Glu Asp Val Gly Val Tyr Tyr Cys Phe Gln Gly Ser His
         85                  90                  95
```

```
gtt ccg tac acg ttc ggc caa ggg acc aag gtg gaa atc aaa          432
Val Pro Tyr Thr Phe Gly Gln Gly Thr Lys Val Glu Ile Lys
    100                 105                 110 cgtacgacta gtcgtgactg ggaaaac                                    459

<210> SEQ ID NO 33
<211> LENGTH: 130
<212> TYPE: DNA
<213> ORGANISM: Artificial Sequence
<220> FEATURE:
<223> OTHER INFORMATION: a synthetic DNA for construction of a DNA
      encoding LV.0

<400> SEQUENCE: 33
caggaaacag ctatgacgaa ttcaggttgc ctcctcaaaa tgaagttgcc tgttaggctg    60
ttggtgctga tgttctggat tcctgcttcc aggagtgata tcgtgatgac tcagtctcca   120
ctctccctgc                                                          130

<210> SEQ ID NO 34
<211> LENGTH: 130
<212> TYPE: DNA
<213> ORGANISM: Artificial Sequence
<220> FEATURE:
<223> OTHER INFORMATION: a synthetic DNA for construction of a DNA
      encoding LV.0

<400> SEQUENCE: 34
agactggcct ggcttctgca ggtaccattc taaataggtt cttccattac tatgtacaag    60
actctgacta gatctgcagg agatggaggc cggctctcca ggggtgacgg gcagggagag   120
tggagactga                                                          130

<210> SEQ ID NO 35
<211> LENGTH: 130
<212> TYPE: DNA
<213> ORGANISM: Artificial Sequence
<220> FEATURE:
<223> OTHER INFORMATION: a synthetic DNA for construction of a DNA
      encoding LV.0

<400> SEQUENCE: 35
tgcagaagcc aggccagtct ccacagctcc tgatctataa agtttccaac cgaatttctg    60
gggtcccaga caggttcagt ggcagtggat ccgggacaga tttcacactg aaaatcagca   120
gggtggaggc                                                          130

<210> SEQ ID NO 36
<211> LENGTH: 129
<212> TYPE: DNA
<213> ORGANISM: Artificial Sequence
<220> FEATURE:
<223> OTHER INFORMATION: a synthetic DNA for construction of a DNA
      encoding LV.0

<400> SEQUENCE: 36
gttttcccag tcacgactag tcgtacgttt gatttccacc ttggtccctt ggccgaacgt    60
gtacggaaca tgtgaaccct gaaagcagta ataaacccg acgtcctcag cctccaccct   120
gctgatttt                                                           129

<210> SEQ ID NO 37
<211> LENGTH: 459
<212> TYPE: DNA
<213> ORGANISM: Artificial Sequence
```

```
<220> FEATURE:
<223> OTHER INFORMATION: a DNA encoding LV.6
<220> FEATURE:
<221> NAME/KEY: CDS
<222> LOCATION: (40)..(432)
<220> FEATURE:
<221> NAME/KEY: sig_peptide
<222> LOCATION: (40)..(96)

<400> SEQUENCE: 37
caggaaacag ctatgacgaa ttcaggttgc ctcctcaaa atg aag ttg cct gtt         54
                                             Met Lys Leu Pro Val
                                                             -15 agg ctg ttg gtg ctg atg ttc tgg att cct gct tcc agg agt gat gtt       102
Arg Leu Leu Val Leu Met Phe Trp Ile Pro Ala Ser Arg Ser Asp Val
            -10                 -5                 -1   1 gtg atg act cag tct cca ctc tcc ctg ccc gtc agt ctt gga gag ccg       150
Val Met Thr Gln Ser Pro Leu Ser Leu Pro Val Ser Leu Gly Glu Pro
              5                  10                  15 gcc tcc atc tcc tgc aga tct agt cag agt ctt gta cat agt aat gga      198
Ala Ser Ile Ser Cys Arg Ser Ser Gln Ser Leu Val His Ser Asn Gly
         20                  25                  30 aga acc tat tta gaa tgg tac ctg cag aag cca ggc cag tct cca aag      246
Arg Thr Tyr Leu Glu Trp Tyr Leu Gln Lys Pro Gly Gln Ser Pro Lys
 35                  40                  45                  50 gtc ctg atc tat aaa gtt tcc aac cga att tct ggg gtc cca gac agg      294
Val Leu Ile Tyr Lys Val Ser Asn Arg Ile Ser Gly Val Pro Asp Arg
                 55                  60                  65 ttc agt ggc agt gga tcc ggg aca gat ttc aca ctg aaa atc agc agg      342
Phe Ser Gly Ser Gly Ser Gly Thr Asp Phe Thr Leu Lys Ile Ser Arg
             70                  75                  80 gtg gag gct gag gac gtc ggg gtt tat ttc tgc ttt cag ggt tca cat      390
Val Glu Ala Glu Asp Val Gly Val Tyr Phe Cys Phe Gln Gly Ser His
         85                  90                  95 gtt ccg tac acg ttc ggc caa ggg acc aag gtg gaa atc aaa              432
Val Pro Tyr Thr Phe Gly Gln Gly Thr Lys Val Glu Ile Lys
    100                 105                 110 cgtacgacta gtcgtgactg ggaaaac                                         459

<210> SEQ ID NO 38
<211> LENGTH: 130
<212> TYPE: DNA
<213> ORGANISM: Artificial Sequence
<220> FEATURE:
<223> OTHER INFORMATION: a synthetic DNA for construction of a DNA
      encoding LV.6

<400> SEQUENCE: 38
caggaaacag ctatgacgaa ttcaggttgc ctcctcaaaa tgaagttgcc tgttaggctg     60
ttggtgctga tgttctggat tcctgcttcc aggagtgatg ttgtgatgac tcagtctcca   120
ctctccctgc                                                           130

<210> SEQ ID NO 39
<211> LENGTH: 130
<212> TYPE: DNA
<213> ORGANISM: Artificial Sequence
<220> FEATURE:
<223> OTHER INFORMATION: a synthetic DNA for construction of a DNA
      encoding LV.6

<400> SEQUENCE: 39
agactggcct ggcttctgca ggtaccattc taaataggtt cttccattac tatgtacaag     60
```

```
actctgacta gatctgcagg agatggaggc cggctctcca agactgacgg gcagggagag      120
tggagactga                                                            130
```

<210> SEQ ID NO 40
<211> LENGTH: 130
<212> TYPE: DNA
<213> ORGANISM: Artificial Sequence
<220> FEATURE:
<223> OTHER INFORMATION: a synthetic DNA for construction of a DNA
      encoding LV.6

<400> SEQUENCE: 40

```
tgcagaagcc aggccagtct ccaaaggtcc tgatctataa agtttccaac cgaatttctg      60
gggtcccaga caggttcagt ggcagtggat ccgggacaga tttcacactg aaaatcagca     120
gggtggaggc                                                            130
```

<210> SEQ ID NO 41
<211> LENGTH: 129
<212> TYPE: DNA
<213> ORGANISM: Artificial Sequence
<220> FEATURE:
<223> OTHER INFORMATION: a synthetic DNA for construction of a DNA
      encoding LV.6

<400> SEQUENCE: 41

```
gttttcccag tcacgactag tcgtacgttt gatttccacc ttggtccctt ggccgaacgt      60
gtacggaaca tgtgaaccct gaaagcagaa ataaaccccg acgtcctcag cctccaccct     120
gctgattt                                                              129
```

<210> SEQ ID NO 42
<211> LENGTH: 112
<212> TYPE: PRT
<213> ORGANISM: Artificial Sequence
<220> FEATURE:
<223> OTHER INFORMATION: LV.4-1, a designed amino acid sequence of VL of
      an anti-FGF-8 CDR-grafted neutralizing antibody

<400> SEQUENCE: 42

```
Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val His Ser
            20                  25                  30

Asn Gly Arg Thr Tyr Leu Glu Trp Tyr Leu Gln Lys Pro Gly Gln Ser
        35                  40                  45

Pro Lys Val Leu Ile Tyr Lys Val Ser Asn Arg Ile Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Ser His Val Pro Tyr Thr Phe Gly Gln Gly Thr Lys Val Glu Ile Lys
            100                 105                 110
```

<210> SEQ ID NO 43
<211> LENGTH: 112
<212> TYPE: PRT
<213> ORGANISM: Artificial Sequence
<220> FEATURE:
<223> OTHER INFORMATION: LV.4-2, a designed amino acid sequence of VL of
      an anti-FGF-8 CDR-grafted neutralizing antibody

<400> SEQUENCE: 43

```
Asp Val Val Met Thr Gln Ser Pro Leu Ser Leu Pro Val Ser Leu Gly
 1               5                  10                  15
Glu Pro Ala Ser Ile Ser Cys Arg Ser Ser Gln Ser Leu Val His Ser
             20                  25                  30
Asn Gly Arg Thr Tyr Leu Glu Trp Tyr Leu Gln Lys Pro Gly Gln Ser
         35                  40                  45
Pro Gln Leu Leu Ile Tyr Lys Val Ser Asn Arg Ile Ser Gly Val Pro
     50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Phe Cys Phe Gln Gly
                 85                  90                  95
Ser His Val Pro Tyr Thr Phe Gly Gln Gly Thr Lys Val Glu Ile Lys
            100                 105                 110
```

<210> SEQ ID NO 44
<211> LENGTH: 112
<212> TYPE: PRT
<213> ORGANISM: Artificial Sequence
<220> FEATURE:
<223> OTHER INFORMATION: LV.3-1, a designed amino acid sequence of VL of an anti-FGF-8 CDR-grafted neutralizing antibody

<400> SEQUENCE: 44

```
Asp Val Val Met Thr Gln Ser Pro Leu Ser Leu Pro Val Thr Pro Gly
 1               5                  10                  15
Glu Pro Ala Ser Ile Ser Cys Arg Ser Ser Gln Ser Leu Val His Ser
             20                  25                  30
Asn Gly Arg Thr Tyr Leu Glu Trp Tyr Leu Gln Lys Pro Gly Gln Ser
         35                  40                  45
Pro Gln Val Leu Ile Tyr Lys Val Ser Asn Arg Ile Ser Gly Val Pro
     50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Phe Cys Phe Gln Gly
                 85                  90                  95
Ser His Val Pro Tyr Thr Phe Gly Gln Gly Thr Lys Val Glu Ile Lys
            100                 105                 110
```

<210> SEQ ID NO 45
<211> LENGTH: 112
<212> TYPE: PRT
<213> ORGANISM: Artificial Sequence
<220> FEATURE:
<223> OTHER INFORMATION: LV.3-2, a designed amino acid sequence of VL of an anti-FGF-8 CDR-grafted neutralizing antibody

<400> SEQUENCE: 45

```
Asp Ile Val Met Thr Gln Ser Pro Leu Ser Leu Pro Val Ser Leu Gly
 1               5                  10                  15
Glu Pro Ala Ser Ile Ser Cys Arg Ser Ser Gln Ser Leu Val His Ser
             20                  25                  30
Asn Gly Arg Thr Tyr Leu Glu Trp Tyr Leu Gln Lys Pro Gly Gln Ser
         35                  40                  45
Pro Gln Leu Leu Ile Tyr Lys Val Ser Asn Arg Ile Ser Gly Val Pro
     50                  55                  60
Asp Arg Phe Ser Gly Ser Gly Ser Gly Thr Asp Phe Thr Leu Lys Ile
```

```
                65                  70                  75                  80
Ser Arg Val Glu Ala Glu Asp Val Gly Val Tyr Phe Cys Phe Gln Gly
                    85                  90                  95

Ser His Val Pro Tyr Thr Phe Gly Gln Gly Thr Lys Val Glu Ile Lys
            100                 105                 110

<210> SEQ ID NO 46
<211> LENGTH: 112
<212> TYPE: PRT
<213> ORGANISM: Artificial Sequence
<220> FEATURE:
<223> OTHER INFORMATION: LV.2-1, a designed amino acid sequence of VL of
      an anti-FGF-8 CDR-grafted neutralizing antibody

<400> SEQUENCE: 46

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Val His Ser
                20                  25                  30

Asn Gly Arg Thr Tyr Leu Glu Trp Tyr Leu Gln Lys Pro Gly Gln Ser
            35                  40                  45

Pro Gln Val Leu Ile Tyr Lys Val Ser Asn Arg Ile Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Phe Gln Gly
                    85                  90                  95

Ser His Val Pro Tyr Thr Phe Gly Gln Gly Thr Lys Val Glu Ile Lys
            100                 105                 110

<210> SEQ ID NO 47
<211> LENGTH: 112
<212> TYPE: PRT
<213> ORGANISM: Artificial Sequence
<220> FEATURE:
<223> OTHER INFORMATION: LV.2-2, a designed amino acid sequence of VL of
      an anti-FGF-8 CDR-grafted neutralizing antibody

<400> SEQUENCE: 47

Asp Val Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Val His Ser
                20                  25                  30

Asn Gly Arg Thr Tyr Leu Glu Trp Tyr Leu Gln Lys Pro Gly Gln Ser
            35                  40                  45

Pro Gln Leu Leu Ile Tyr Lys Val Ser Asn Arg Ile Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Phe Gln Gly
                    85                  90                  95

Ser His Val Pro Tyr Thr Phe Gly Gln Gly Thr Lys Val Glu Ile Lys
            100                 105                 110

<210> SEQ ID NO 48
<211> LENGTH: 39
<212> TYPE: DNA
<213> ORGANISM: Artificial Sequence
<220> FEATURE:
<223> OTHER INFORMATION: a primer for construction of DNA encoding
```

```
        LV.3-1

<400> SEQUENCE: 48
atggtacctg cagaagccag gccagtctcc acaggtcct                                39

<210> SEQ ID NO 49
<211> LENGTH: 39
<212> TYPE: DNA
<213> ORGANISM: Artificial Sequence
<220> FEATURE:
<223> OTHER INFORMATION: a primer for construction of DNA encoding
      LV.2-2

<400> SEQUENCE: 49
atggtacctg cagaagccag gccagtctcc acagctcct                                39

<210> SEQ ID NO 50
<211> LENGTH: 112
<212> TYPE: PRT
<213> ORGANISM: Artificial Sequence
<220> FEATURE:
<223> OTHER INFORMATION: LV.4-3, a designed amino acid sequence of VL of
      an anti-FGF-8 CDR-grafted neutralizing antibody

<400> SEQUENCE: 50

Asp Ile Val Met Thr Gln Ser Pro Leu Ser Leu Pro Val Ser Leu Gly
 1               5                  10                  15

Glu Pro Ala Ser Ile Ser Cys Arg Ser Ser Gln Ser Leu Val His Ser
            20                  25                  30

Asn Gly Arg Thr Tyr Leu Glu Trp Tyr Leu Gln Lys Pro Gly Gln Ser
        35                  40                  45

Pro Gln Val Leu Ile Tyr Lys Val Ser Asn Arg Ile Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Ser His Val Pro Tyr Thr Phe Gly Gln Gly Thr Lys Val Glu Ile Lys
            100                 105                 110

<210> SEQ ID NO 51
<211> LENGTH: 112
<212> TYPE: PRT
<213> ORGANISM: Artificial Sequence
<220> FEATURE:
<223> OTHER INFORMATION: LV.3-3, a designed amino acid sequence of VL of
      an anti-FGF-8 CDR-grafted neutralizing antibody

<400> SEQUENCE: 51

Asp Ile Val Met Thr Gln Ser Pro Leu Ser Leu Pro Val Ser Leu Gly
 1               5                  10                  15

Glu Pro Ala Ser Ile Ser Cys Arg Ser Ser Gln Ser Leu Val His Ser
            20                  25                  30

Asn Gly Arg Thr Tyr Leu Glu Trp Tyr Leu Gln Lys Pro Gly Gln Ser
        35                  40                  45

Pro Gln Val Leu Ile Tyr Lys Val Ser Asn Arg Ile Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95
```

```
Ser His Val Pro Tyr Thr Phe Gly Gln Gly Thr Lys Val Glu Ile Lys
        100                 105                 110
```

REMEDIES FOR ARTHRITIS

This application is the US national phase of international application PCT/JP02/13650 filed 26 Dec. 2002, which designated the US and claims benefit of JP 2001-400677 filed 28 Dec. 2001, the entire contents of each of which are incorporated herein by reference.

TECHNICAL FIELD

The present invention relates to an agent for preventing or treating arthritis, an agent for inhibiting joint destruction, an agent for protecting cartilage, an agent for inhibiting growth of synovial membrane and a diagnostic agent for arthritis comprising an anti-FGF-8 antibody as an active ingredient, as well as a method for judging arthritis using the antibody.

BACKGROUND ART

The number of persons complaining of arthropathy has been surely increased in the aging society. It is very important to perform early diagnosis or screening of diseases such as osteoarthritis and rheumatoid arthritis as typical articular diseases or exact prognostic analysis of patients, and the treatment thereof leads to the improve in quality of life of many aged persons. However, satisfactory diagnostic and therapeutic methods have not yet been established.

The articular cartilage is a tissue that comprises a small number of chondrocytes covering the movable surface of the joint and a large number of extracellular matrix. Blood vessels or nerves are not distributed therein, and nutrients are supplied mainly from a synovial fluid produced from the synovial membrane covering the inner surface of the joint. Further, it is not only avascular but also exhibits strong resistance to invasion of blood vessels from the peripheral tissues rich in vasoganglion. Chondrocytes intricately control both of synthesis and degradation of extracellular matrix to play a major role in maintaining homeostasis of extracellular matrix. Chemical factors such as cytokines and growth factors and dynamic factors such as weight loading act on chondrocytes and change the balance of both the synthesis and the degradation of extracellular matrix to influence metabolism of extracellular matrix.

Osteoarthritis is caused by the aging or mechanical stresses to thereby induce disruption of the articular cartilage surface accompanied by growth of new cartilages around joints, deformation of joints and failure of adaptability and to lead to inflammation of synovial membranes of joints. The osteoarthritis is a monoarthritis disease with delayed denaturation of the articular cartilage, and characteristics thereof are often pains and functional loss (Manek M. J. and Lane N. E., Am. Fam. Physician, 61, 1795-1804, 2000).

In rheumatoid arthritis, inflammatory cells invade synovial membranes because of immunological abnormality or infectious diseases, and the growth of synovial fibroblasts progresses according to angiogenesis to form an inflammatory synovial granulation tissue called pannus. When the pannus is formed, destruction of bones or cartilages proceeds to cause irreversible disorder in joints. During the destruction of bones or cartilages, various extracellular matrix present in large quantities, such as collagen and proteoglycan are degraded.

In articular diseases such as osteoarthritis and rheumatoid arthritis, the synovitis and the destruction of extracellular matrix lead to the functional loss of articular cartilages.

Osteoarthritis and rheumatoid arthritis are quite different diseases, but have many common points in the articular cartilage destruction mechanism. Many types of matrix metalloproteases are produced and secreted in the articular synovial fluid and articular portions such as a synovial membrane and a cartilage, and matrix metalloproteases are excessively detected in the articular portions. Matrix metalloproteases degrade many types of extracellular matrix, which is one cause of articular destruction. They are produced not only from inflamed synovial membranes, macrophages and neutrophils but also from chondrocytes. This production is controlled by various cytokines produced or secreted in the same articular portions, superoxide anion, nitric oxide, prostaglandins, growth factors and the like. It has been reported that these induce the production of matrix metalloproteases from synovial cells and chondrocytes to promote degradation of extracellular matrix.

From these reports, it is considered that osteoarthritis and rheumatoid arthritis as well as arthritic diseases such as systemic lupus erythematosus which is an cryptogenic disease with an inflammatory tissue disorder caused by appearance of autoantibody and tissue deposition of an antigen-antibody complex and in which arthropathy occurs at a high rate, arthropathy, psoriatic arthritis leading to bone destruction with synovial membrane growth complicated in psoriatic patients, discopathy in which destruction of extracellular matrix of the intervertebral disc disease is observed and acute crystalline synovitis (gout, pseudogout) (Ryumachi Gaku, compiled by Hirohata Kazushi et al., Dobun Shoin, 1989) can be treated by inhibiting growth of the synovial membrane or destruction of cartilages.

In the pharmacotherapy of rheumatoid arthritis, various non-steroidal antiinflammatory agents, steroidal agents such as prednisolone and antirheumatic agents such as methotrexate have been so far used mainly to reduce pains and inflammation of joints (Chiryo, 78, 3553-3558, Nanzando, 1996). In osteoarthritis, various non-steroidal antiinflammatory agents, analgesic agents, hyaluronic acid pharmaceutical preparations as an intraarticular injection and the like have been administered to remove pains and inflammation. Hyaluronic acid which inhibits destruction of cartilages has been used as an agent for protecting cartilage (Creamer P., J. Rheum., 20, 1461-1464, 1993, Arthritis Rheum., 43, 1905-1915, 2000). Further, physical therapy and operative treatments such as osteotomy and artificial joint replacement have been carried out. Non-steroidal antiinflammatory agents and steroidal agents such as prednisolone are used in systemic lupus erythematosus, non-steroidal antiinflammatory agents and sulfasalazine as an antirheumatic drug in ankylotic arthropathy, non-steroidal antiinflammatory agents, antirheumatic drugs and steroidal intraarticular injections in psoriatic arthritis which involves synovial membrane growth complicated in psoriatic patients and leads to bone destruction, non-steroidal antiinflammatory agents and analgesic agents in intervertebral disc disease in which destruction of extracellular matrix of the intervertebral disk is observed, and non-steroidal antiinflammatory agents, colchicine and the like in acute crystalline synovitis respectively (Ryumachi Gaku, compiled by Hirohata Kazushi et al., Dobun Shoin, 1989). However, such a pharmacotherapy is a symptomatic therapy, and it has hardly inhibited the destruction of joints sufficiently.

In the therapy of rheumatoid arthritis, the selection of the positive therapy to prevent the destruction of joints as much as possible is currently being accepted. The point of this therapy is that a disease is diagnosed as rheumatoid arthritis at the earliest possible stage and antirheumatic drugs such as methotrexate are properly selected. However, sufficient diagnosis has not yet been provided.

A fibroblast growth factor (hereinafter abbreviated as FGF), one of various growth factors existing in vivo, has been known as a heparin-binding growth factor that affects vascular endothelial cells. Further, the FGF family involves 19 types or more, and FGF-2 (basic FGF), FGF-1 (acidic FGF) and the like have been long known. As an FGF receptor, seven types have been to date found, and encode a tyrosine kinase in the intracellular region.

FGF-8 is a factor isolated from a culture supernatant of mouse breast cancer cell line SC-3 (Nakamura N. et al., J. Steroid Biochem., 27, 459-464, 1987) showing sex hormone-dependent growth as an androgen-induced growth factor (AIGF). It is a growth factor which is inductively produced by androgen stimulation and enhances the growth of SC-3 cells in an autocrine manner (Tanaka A. et al., Proc. Natl. Acad. Sci. USA, 89, 8928-8932, 1992). It is reported that FGF-8 accelerates the growth of cells of prostate cancer or fibroblasts (Tanaka A. et al., FEBS Lett., 363, 226-230, 1995). It is reported that FGF-8 bound to three receptors, FGF receptor-2IIIc, FGF receptor-3IIIc and FGF receptor-4 (Ornitz D. M. et al., J. Biol. Chem., 271, 15292-15297, 1996). Moreover, binding to membrane type heparan sulfate proteoglycan such as syndecan is required for the function of FGF. Binding to heparan sulfate is necessary to the stable and local accumulation of FGF. In the situation of tissue remodelingion such as inflammation, it is considered that heparan sulfate is degraded to liberate FGF from extracellular matrix to exhibit its activity. A strong angiogenesis factor such as FGF-2 is comprised in cartilages (Satoh H. et al., J. Biol. Chem., 273, 12307-12315, 1998). In the arthritis, synovial cells, chondrocytes and inflammatory cells invaded synthesize FGF-1 or FGF-2 at an extremely high level (Sano H. et al., J. Cell Biol., 110, 1417-1426, 1990, Remmers E. F., Growth factors, 2, 179-188, 1990), and the FGF-2 concentration in a synovial fluid of rheumatic patients correlates with arthritis (Manabe N. et al., Rheumatology, 38, 714-720, 1999). FGF-2 is involved in osteophyte formation in osteoarthritis (Uchino M. et al., Clin. Orthop., 377, 119-125, 2000). These reports prove that FGF-1 or FGF-2 is involved in arthritis.

In the report using FGF-8 knockout mice, FGF-8 expressed at the stage of the development of joints (Haraguchi R. et al., Development, 127, 2471-2479, 2000; Lewandoski M. et al., Nat. Genet., 26, 460-463, 2000). Nevertheless, it is unknown that FGF-8 is involved in arthritis.

DISCLOSURE OF THE INVENTION

It is an object of the invention to provide an agent for preventing or treating arthritis, an agent for inhibiting joint destruction, an agent for cartilage protection, an agent for inhibiting the growth of synovial membrane and a diagnostic agent for arthritis, as well as a diagnostic method for arthritis.

DISCLOSURE OF THE INVENTION

The invention provides the following (1) to (51).

(1) An agent for preventing or treating arthritis, comprising, as an active ingredient, an antibody which specifically binds to FGF-8 to inhibit activity of FGF-8.

(2) The agent according to (1), wherein the antibody which specifically binds to FGF-8 to inhibit activity of FGF-8 is a monoclonal antibody.

(3) The agent according to (2), wherein the monoclonal antibody is an antibody selected from an antibody produced by a hybridoma, a humanized antibody and an antibody fragment thereof.

(4) The agent according to (3), wherein the hybridoma is hybridoma KM1334 (FERM BP-5451).

(5) The agent according to (3), wherein the humanized antibody is a human chimeric antibody or a human complementarity determining region (CDR)-grafted antibody.

(6) The agent according to (5), wherein the human chimeric antibody comprises an antibody heavy chain variable region (VH) and an antibody light chain variable region (VL) of a monoclonal antibody which specifically binds to FGF-8 to inhibit activity of FGF-8, and an antibody heavy chain constant region (CH) and an antibody light chain constant region (CL) of a human antibody.

(7) The agent according to (6), wherein the human chimeric antibody is any of the following human chimeric antibodies (a) to (c), (a) a human chimeric antibody in which VH comprises an amino acid sequence represented by SEQ ID NO. 5, (b) a human chimeric antibody in which VL comprises an amino acid sequence represented by SEQ ID NO. 6, and (c) a human chimeric antibody in which VH comprises an amino acid sequence represented by SEQ ID NO. 5 and VL comprises an amino acid sequence represented by SEQ ID NO. 6.

(8) The agent according to (7), wherein the human chimeric antibody is a human chimeric antibody produced by transformant KM3034 (FERM BP-7836).

(9) The agent according to (5), wherein the human CDR-grafted antibody comprises CDRs of VH and VL of a monoclonal antibody which specifically binds to FGF-8 to inhibit activity of FGF-8 and CH and CL of a human antibody.

(10) The agent according to (9), wherein the human CDR-grafted antibody comprises CDRs of VH and VL of a monoclonal antibody which specifically binds to FGF-8 to inhibit activity of FGF-8, framework regions (FRs) of VH and VL of a human antibody and CH and CL of a human antibody.

(11) The agent according to (9) or (10), wherein the human CDR-grafted antibody is any of the following human CDR-grafted antibodies (a) to (c), (a) a human CDR-grafted antibody in which CDR1, CDR2 and CDR3 of VH comprise amino acid sequences represented by SEQ ID NOS. 7, 8 and 9 respectively, (b) a human CDR-grafted antibody in which CDR1, CDR2 and CDR3 of VL comprise amino acid sequences represented by SEQ ID NOS. 10, 11 and 12 respectively, and (c) a human CDR-grafted antibody in which CDR1, CDR2 and CDR3 of VH comprise amino acid sequences represented by SEQ ID NOS. 7, 8 and 9 respectively and CDR1, CDR2 and CDR3 of VL comprise amino acid sequences represented by SEQ ID NOS. 10, 11 and 12 respectively.

(12) The agent according to (9) or (10), wherein the human CDR-grafted antibody is any of the following human CDR-grafted antibodies (a) to (c), (a) a human CDR-grafted antibody in which VH comprises an amino acid sequence represented by SEQ ID NO. 18 in which at least one or more amino acid residue selected from Lys at position 12, Lys at position 13, Ala at position 40, Pro at position 41, Met at position 48, Val at position 68, Ile at position 70, Thr at position 74, Thr at position 76, Glu at position 82, Ser at position 84, Arg at position 87 and Tyr at position 95 is replaced with another amino acid residue, (b) a human CDR-grafted antibody in which VL comprises an amino acid sequence represented by SEQ ID NO. 19 in which at least one or more amino acid residue selected from Ile at position 2, Val at position 3, Thr at position 14, Pro at position 15, Gln at position 50, Leu at position 51 and Tyr at position 92 is replaced with another amino acid residue, and (c) a human CDR-grafted antibody in which VH comprises an amino acid sequence represented by SEQ ID NO. 18 in which at least one or more amino acid residue selected from Lys at position 12, Lys at position 13, Ala at position 40, Pro at position 41, Met at position 48, Val at position 68, Ile at position 70, Thr at position 74, Thr at position 76, Glu at position 82, Ser at position 84, Arg at position 87 and Tyr at position 95 is replaced with another amino acid residue, and VL comprises an amino acid sequence represented by SEQ ID NO. 19 in which at least one or more amino acid residue selected from Ile at position 2, Val at position 3, Thr at position 14, Pro at position 15, Gln at position 50, Leu at position 51 and Tyr at position 92 is replaced with another amino acid residue.

(13) The agent according to (9) or (10), wherein the human CDR-grafted antibody is any of the following human CDR-grafted antibodies (a) to (c), (a) a human CDR-grafted antibody in which VH comprises an amino acid sequence represented by SEQ ID NO. 18 or 20, (b) a human CDR-grafted antibody in which VL comprises an amino acid sequence represented by SEQ ID NO. 19, 21, 42, 43, 44, 45, 46, 47, 50 or 51, and (c) a human CDR-grafted antibody in which VH comprises an amino acid sequence represented by SEQ ID NO. 18 or 20 and VL comprises an amino acid sequence represented by SEQ ID NO. 19, 21, 42, 43, 44, 45, 46, 47, 50 or 51.

(14) The agent according to (13), wherein the human CDR-grafted antibody is any of the following human CDR-grafted antibodies (a) to (c), (a) a human CDR-grafted antibody in which VH comprises an amino acid sequence represented by SEQ ID NO. 18 and VL comprises an amino acid sequence represented by SEQ ID NO. 21, (b) a human CDR-grafted antibody in which VH comprises an amino acid sequence represented by SEQ ID NO. 18 and VL comprises an amino acid sequence represented by SEQ ID NO. 44, and (c) a human CDR-grafted antibody in which VH comprises an amino acid sequence represented by SEQ ID NO. 18 and VL comprises an amino acid sequence represented by SEQ ID NO. 50.

(15) The agent according to (9) or (10), wherein the human CDR-grafted antibody is any of the following human CDR-grafted antibodies (a) to (c), (a) a human CDR-grafted antibody produced by transformant KM8037 (FERM BP-8084), (b) a human CDR-grafted antibody produced by transformant KM8035 (FERM BP-8082), and (c) a human CDR-grafted antibody produced by transformant KM8036 (FERM BP-8083).

(16) The agent according to (3), wherein the antibody fragment is an antibody fragment selected from Fab, Fab', F(ab')$_2$, a single chain antibody (scFv), a dimerized variable region (V region) fragment (diabody), a disulfide-stabilized V region fragment (dsFv) and a CDR-containing peptide.

(17) A diagnostic agent of arthritis comprising an antibody which specifically binds to FGF-8 as an active ingredient.

(18) The diagnostic agent according to (17), wherein the antibody which specifically binds to FGF-8 is a polyclonal antibody or a monoclonal antibody.

(19) The diagnostic agent according to (18), wherein the monoclonal antibody is an antibody selected from an antibody produced by a hybridoma, a humanized antibody and an antibody fragment thereof.

(20) The diagnostic agent according to (19), wherein the hybridoma is hybridoma KM1334 (FERM BP-5451).

(21) The diagnostic agent according to (19), wherein the humanized antibody is a human chimeric antibody or a human CDR-grafted antibody.

(22) The diagnostic agent according to (21), wherein the human chimeric antibody is a human chimeric antibody comprising VH and VL of a monoclonal antibody which specifically binds to FGF-8 and CH and CL of a human antibody.

(23) The diagnostic agent according to (22), wherein the human chimeric antibody is any of the following human chimeric antibodies (a) to (c), (a) a human chimeric antibody in which VH comprises an amino acid sequence represented by SEQ ID NO. 5, (b) a human chimeric antibody in which VL comprises an amino acid sequence represented by SEQ ID NO. 6, and (c) a human chimeric antibody in which VH comprises an amino acid sequence represented by SEQ ID NO. 5 and VL comprises an amino acid sequence represented by SEQ ID NO. 6.

(24) The diagnostic agent according to (23), wherein the human chimeric antibody is a human chimeric antibody produced by transformant KM3034 (FERM BP-7836).

(25) The diagnostic agent according to (21), wherein the human CDR-grafted antibody is a human CDR-grafted antibody comprising CDRs of VH and VL of a monoclonal antibody which specifically binds to FGF-8 and CH and CL of a human antibody.

(26) The diagnostic agent according to (25), wherein the human CDR-grafted antibody is a human CDR-grafted antibody comprising CDRs of VH and VL of a monoclonal antibody which specifically binds to FGF-8, FRs of VH and VL of a human antibody and CH and CL of a human antibody.

(27) The diagnostic agent according to (25) or (26), wherein the human CDR-grafted antibody is any of the following human CDR-grafted antibodies (a) to (c), (a) a human CDR-grafted antibody in which CDR1, CDR2 and CDR3 of VH comprise amino acid sequences represented by SEQ ID NOS. 7, 8 and 9 respectively, (b) a human CDR-grafted antibody in which CDR1, CDR2 and CDR3 of VL comprise amino acid sequences represented by SEQ ID NOS. 10, 11 and 12 respectively, and (c) a human CDR-grafted antibody in which CDR1, CDR2 and CDR3 of VH comprise amino acid sequences represented by SEQ ID NOS. 7, 8 and 9 respectively, and CDR1, CDR2 and CDR3 of VL comprise amino acid sequences represented by SEQ ID NOS. 10, 11 and 12 respectively.

(28) The diagnostic agent according to (25) or (26), wherein the human CDR-grafted antibody is any of the following human CDR-grafted antibodies (a) to (c), (a) a human CDR-grafted antibody in which VH comprises an amino acid sequence represented by SEQ ID NO. 18 in which at least one or more amino acid residue selected from Lys at position 12, Lys at position 13, Ala at position 40, Pro at position 41, Met at position 48, Val at position 68, Ile at position 70, Thr at position 74, Thr at position 76, Glu at position 82, Ser at position 84, Arg at position 87 and Tyr at position 95 is replaced with another amino acid residue, (b) a human CDR-grafted antibody in which VL comprises an amino acid sequence represented by SEQ ID NO. 19 in which at least one or more amino acid residue selected from Ile at position 2, Val at position 3, Thr at position 14, Pro at position 15, Gln at position 50, Leu at position 51 and Tyr at position 92 is replaced with another amino acid residue, and (c) a human CDR-grafted antibody in which VH comprises an amino acid sequence represented by SEQ ID NO. 18 in which at least one or more amino acid residue selected from Lys at position 12, Lys at position 13, Ala at position 40, Pro at position 41, Met at position 48, Val at position 68, Ile at position 70, Thr at position 74, Thr at position 76, Glu at position 82, Ser at position 84, Arg at position 87 and Tyr at position 95 is replaced with another amino acid residue, and VL comprises an amino acid sequence represented by SEQ ID NO. 19 in which at least one or more amino acid residue selected from Ile at position 2, Val at position 3, Thr at position 14, Pro at position 15, Gln at position 50, Leu at position 51 and Tyr at position 92 is replaced with another amino acid residue.

(29) The diagnostic agent according to (25) or (26), wherein the human CDR-grafted antibody is any of the following human CDR-grafted antibodies (a) to (c), (a) a human CDR-grafted antibody in which VH comprises an amino acid sequence represented by SEQ ID NO. 18 or 20, (b) a human CDR-grafted antibody in which VL comprises an amino acid sequence represented by SEQ ID NO. 19, 21, 42, 43, 44, 45, 46, 47, 50 or 51, and (c) a human CDR-grafted antibody in which VH comprises an amino acid sequence represented by SEQ ID NO. 18 or 20 and VL comprises an amino acid sequence represented by SEQ ID NO. 19, 21, 42, 43, 44, 45, 46, 47, 50 or 51.

(30) The diagnostic agent according to (29), wherein the human CDR-grafted antibody is any of the human CDR-grafted antibodies (a) to (c), (a) a human CDR-grafted antibody in which VH comprises an amino acid sequence represented by SEQ ID NO. 18 and VL comprises an amino acid sequence represented by SEQ ID NO. 21, (b) a human CDR-grafted antibody in which VH comprises an amino acid sequence represented by SEQ ID NO. 18 and VL comprises an amino acid sequence represented by SEQ ID NO. 44, and (c) a human CDR-grafted antibody in which VH comprises an amino acid sequence represented by SEQ ID NO. 18 and VL comprises an amino acid sequence represented by SEQ ID NO. 50.

(31) The diagnostic agent according to (25) or (26), wherein the human CDR-grafted antibody is any of the following human CDR-grafted antibodies (a) to (c), (a) a human CDR-grafted antibody produced by transformant KM8037 (FERM BP-8084), (b) a human CDR-grafted antibody produced by transformant KM8035 (FERM BP-8082), and (c) a human CDR-grafted antibody produced by transformant KM8036 (FERM BP-8083).

(32) The diagnostic agent according to (19), wherein the antibody fragment is an antibody fragment selected from Fab, Fab', F(ab')$_2$, a single-chain antibody (scFv), a dimerized V region fragment (diabody), a disulfide-stabilized V region fragment (dsFv) and a CDR-containing peptide.

(33) A diagnostic method for arthritis, which comprises detecting and/or determining FGF-8 in a sample using an antibody which specifically binds to FGF-8.

(34) The diagnostic method according to (33), wherein the antibody which specifically binds to FGF-8 is a polyclonal antibody or a monoclonal antibody.

(35) The diagnostic method according to (34), wherein the monoclonal antibody is an antibody selected from an antibody produced by a hybridoma, a humanized antibody and an antibody fragment thereof.

(36) The diagnostic method according to (35), wherein the hybridoma is hybridoma KM1334 (FERM BP-5451).

(37) The diagnostic method according to (35), wherein the humanized antibody is a human chimeric antibody or a human CDR-grafted antibody.

(38) The diagnostic method according to (37), wherein the human chimeric antibody is a human chimeric antibody comprising VH and VL of a monoclonal antibody which specifically binds to FGF-8 and CH and CL of a human antibody.

(39) The diagnostic method according to (38), wherein the human chimeric antibody is any of the following human chimeric antibodies (a) to (c), (a) a human chimeric antibody in which VH comprises an amino acid sequence represented by SEQ ID NO. 5, (b) a human chimeric antibody in which VL comprises an amino acid sequence represented by SEQ ID NO. 6, and (c) a human chimeric antibody in which VH comprises an amino acid sequence represented by SEQ ID NO. 5 and VL comprises an amino acid sequence represented by SEQ ID NO. 6.

(40) The diagnostic method according to (39), wherein the human chimeric antibody is a human chimeric antibody produced by transformant KM3034 (FERM BP-7836).

(41) The diagnostic method according to (37), wherein the human CDR-grafted antibody is a human CDR-grafted antibody comprising CDRs of VH and VL of a monoclonal antibody which specifically binds to FGF-8 and CH and CL of a human antibody.

(42) The diagnostic method according to (41), wherein the human CDR-grafted antibody is a human CDR-grafted antibody comprising CDRs of VH and VL of a monoclonal antibody which specifically binds to FGF-8, FRs of VH and VL of a human antibody and CH and CL of a human antibody.

(43) The diagnostic method according to (41) or (42), wherein the human CDR-grafted antibody is any of the following human CDR-grafted antibodies (a) to (c), (a) a human CDR-grafted antibody in which CDR1, CDR2 and CDR3 of VH comprise amino acid sequences represented by SEQ ID NOS. 7, 8 and 9 respectively, (b) a human CDR-grafted antibody in which CDR1, CDR2 and CDR3 of VL comprise amino acid sequences represented by SEQ ID NOS. 10, 11 and 12 respectively, and (c) a human CDR-grafted antibody in which CDR1, CDR2 and CDR3 of VH comprise amino acid sequences represented by SEQ ID NOS. 7, 8 and 9 respectively, and CDR1, CDR2 and CDR3 of VL comprise amino acid sequences represented by SEQ ID NOS. 10, 11 and 12 respectively.

(44) The diagnostic method according to (41) or (42), wherein the human CDR-grafted antibody is any of the following human CDR-grafted antibodies (a) to (c), (a) a human CDR-grafted antibody in which VH comprises an amino acid sequence represented by SEQ ID NO. 18 in which at least one amino or more acid residue selected from Lys at position 12, Lys at position 13, Ala at position 40, Pro at position 41, Met at position 48, Val at position 68, Ile at position 70, Thr at position 74, Thr at position 76, Glu at position 82, Ser at position 84, Arg at position 87 and Tyr at position 95 is replaced with another amino acid residue, (b) a human CDR-grafted antibody in which VL comprises an amino acid sequence represented by SEQ ID NO. 19 in which at least one amino or more acid residue selected from Ile at position 2, Val at position 3, Thr at position 14, Pro at position 15, Gln at position 50, Leu at position 51 and Tyr at position 92 is replaced with another amino acid residue, and (c) a human CDR-grafted antibody in which VH comprises an amino acid sequence represented by SEQ ID NO. 18 in which at least one or more amino acid residue selected from Lys at position 12, Lys at position 13, Ala at position 40, Pro at position 41, Met at position 48, Val at position 68, Ile at position 70, Thr at position 74, Thr at position 76, Glu at position 82, Ser at position 84, Arg at position 87 and Tyr at position 95 is replaced with another amino acid residue, and VL comprises an amino acid sequence represented by SEQ ID NO. 19 in which at least one or more amino acid residue selected from Ile at position 2, Val at position 3, Thr at position 14, Pro at position 15, Gln at position 50, Leu at position 51 and Tyr at position 92 is replaced with another amino acid residue.

(45) The diagnostic method according to (41) or (42), wherein the human CDR-grafted antibody is any of the following human CDR-grafted antibodies (a) to (c), (a) a human CDR-grafted antibody in which VH comprises an amino acid sequence represented by SEQ ID NO. 18 or 20, (b) a human CDR-grafted antibody in which VL comprises an amino acid sequence represented by SEQ ID NO. 19, 21, 42, 43, 44, 45, 46, 47, 50 or 51, and (c) a human CDR-grafted antibody in which VH comprises an amino acid sequence represented by SEQ ID NO. 18 or 20 and VL comprises an amino acid sequence represented by SEQ ID NO. 19, 21, 42, 43, 44, 45, 46, 47, 50 or 51.

(46) The diagnostic method according to (45), wherein the human CDR-grafted antibody is any of the following human CDR-grafted antibodies (a) to (c), (a) a human CDR-grafted antibody in which VH comprises an amino acid sequence represented by SEQ ID NO. 18 and VL comprises an amino acid sequence represented by SEQ ID NO. 21, (b) a human CDR-grafted antibody in which VH comprises an amino acid sequence represented by SEQ ID NO. 18 and VL comprises an amino acid sequence represented by SEQ ID NO. 44, and (c) a human CDR-grafted antibody in which VH comprises an amino acid sequence represented by SEQ ID NO. 18 and VL comprises an amino acid sequence represented by SEQ ID NO. 50.

(47) The diagnostic method according to (41) or (42), wherein the human CDR-grafted antibody is any of the following human CDR-grafted antibodies (a) to (c), (a) a human CDR-grafted antibody produced by transformant KM8037 (FERM BP-8084), (b) a human CDR-grafted antibody produced by transformant KM8035 (FERM BP-8082), and (c) a human CDR-grafted antibody produced by transformant KM8036 (FERM BP-8083).

(48) The diagnostic method according to (35), wherein the antibody fragment is an antibody fragment selected from Fab, Fab', F(ab')$_2$, a single chain antibody (scFv), a dimerized V region fragment (diabody), a disulfide-stabilized V region fragment (dsFv) and a CDR-containing peptide.

(49) An agent for inhibiting a joint destruction comprising, as an active ingredient, an antibody which specifically binds to FGF-8 to inhibit activity of FGF-8.

(50) An agent for protecting cartilage comprising, as an active ingredient, an antibody which specifically binds to FGF-8 to inhibit activity of FGF-8.

(51) An agent for inhibiting growth of synovial membrane comprising, as an active ingredient, an antibody which specifically binds to FGF-8 to inhibit activity of FGF-8.

The antibody used in the agent for preventing or treating arthritis in the present invention may be any antibody so long as it is an antibody which specifically binds to FGF-8 to inhibit activity of FGF-8 (hereinafter also referred to as an anti-FGF-8 neutralizing antibody). Examples include an antibody having neutralizing activity to FGF-8 and a fragment thereof.

The anti-FGF-8 neutralizing antibody used in the agent for preventing or treating arthritis in the present invention can be obtained by selecting an antibody capable of inhibiting activity of FGF-8 from among antibodies which specifically binds to FGF-8 (hereinafter also referred to as anti-FGF-8 antibodies). The activity of FGF-8 may be any of biological activities that FGF-8 possesses. Specific examples thereof can include an activity that promotes growth of mouse breast cancer cell line SC-3 (Nakamura N. et al., J. Steroid Biochem., 27, 459-464, 1987), mouse fibroblast cell line NIH/3T3 (ATCC No: CRL-1658) or human prostate cancer cell line LNCaP (ATCC No: CRL-1740), an activity that promotes the growth of synovial cells, an activity that promotes degradation of extracellular matrix of chondrocytes and an activity that promotes production of matrix metalloproteinase-3 from chondrocytes.

An anti-FGF-8 antibody can be produced by the known method (Harlow E. and Lane D., Antibodies: A Laboratory Manual, Cold Spring Harbor Laboratory, 1988, hereinafter referred to as Antibodies A Laboratory Manual).

As the anti-FGF-8 neutralizing antibody used in the agent for preventing or treating arthritis of the present invention, a polyclonal antibody and a monoclonal antibody can both be used. A monoclonal antibody is preferably used.

Examples of the monoclonal antibody can include an antibody produced by a hybridoma, a humanized antibody and an antibody fragment thereof.

The anti-FGF-8 neutralizing monoclonal antibody produced by the hybridoma as used in the agent for preventing or treating arthritis in the invention specifically is produced by the following method.

That is, an FGF-8 protein is prepared as an antigen, and plasma cells having a specificity for the antigen are induced in an animal immunized with this antigen. The plasma cells are further fused with myeloma cells to prepare hybridomas, and the hybridomas are cultured. Or the hybridoma cells are administered to an animal to cause ascitic canceration in the animal. Antibodies which specifically binds to FGF-8 are separated from the culture solution or the ascitic fluid, and purified. An antibody that inhibits activity of FGF-8 is selected from among the resulting antibodies. The anti-FGF-8 neutralizing monoclonal antibody includes monoclonal antibody KM1334 produced by hybridoma KM1334 (FERM BP-5451) belonging to mouse IgG1 subclass as described in Japanese published unexamined application No. 271391/97.

The humanized antibody used in the agent for preventing or treating arthritis of the present invention includes the foregoing anti-FGF-8 neutralizing monoclonal antibody which is modified by a gene recombination technology. The antibody having low antigenicity and prolonged blood half-life is preferably in the preventing or treating agent.

The humanized antibody used in the agent for preventing or treating arthritis of the present invention includes a human chimeric antibody and a human complementary determining region (hereinafter abbreviated as CDR)-grafted antibody.

The human chimeric antibody means an antibody comprising the antibody heavy-chain variable region (the variable region is hereinafter referred to as V region and the heavy-chain variable region as VH) and light-chain V region (hereinafter referred to as VL) of a non-human animal, and the human antibody heavy-chain constant region (the constant region is hereinafter referred to as C region and the heavy-chain constant region as CH) and the human antibody light-chain C region (hereinafter referred to as CL). As the non-human animal, any of animals from which a hybridoma can be prepared, such as mice, rats, hamsters and rabbits, can be used.

The human chimeric antibody used in the agent for preventing or treating arthritis of the present invention can be prepared by obtaining DNAs encoding VH and VL from cDNAs encoding H chain and L chain of the antibody obtained from the hybridoma producing the anti-FGF-8 neutralizing monoclonal antibody, individually inserting the DNAs into a vector for expression in animal cells carrying DNAs encoding human antibody CH and CL to construct a human chimeric antibody expression vector and introducing the vector into the animal cell for expression.

As CH of the human chimeric antibodies, any CH of antibodies belonging to human immunoglobulin (hIg) may be used. CH of antibodies belonging to hIgG class is preferable, and any of subclasses such as γ1, γ2, γ3 and γ4 belonging to hIgG class may be used. As CL of the human chimeric antibodies, any CL of antibodies belonging to hIg, for example, κ class or λ class, may be used.

The human chimeric antibody which specifically binds to FGF-8 to inhibit activity of FGF-8 (hereinafter also referred to as an anti-FGF-8 neutralizing chimeric antibody) includes an anti-FGF-8 neutralizing chimeric antibody comprising VH and VL of a monoclonal antibody which specifically binds to FGF-8 to inhibit activity of FGF-8 and VH and CL of a human antibody. Preferable examples thereof include a human chimeric antibody in which VH comprises an amino acid sequence represented by SEQ ID NO. 5, a human chimeric antibody in which VL comprises an amino acid sequence represented by SEQ ID NO. 6, and a human chimeric antibody in which VH comprises an amino acid sequence represented by SEQ ID NO. 5 and VL comprises an amino acid sequence represented by SEQ ID NO. 6. Specific examples thereof include human chimeric antibodies KM3034 and KM3334 in which VH of the antibody comprises an amino acid sequence represented by SEQ ID NO. 5, CH comprises an amino acid sequence of human γ1 subclass, VL of the antibody comprises an amino acid sequence represented by SEQ ID NO. 6 and CL comprises an amino acid sequence of human κ class.

Transformant KM3034 which produces human chimeric antibody KM3034 was deposited as FERM BP-7836 in International Patent Organism Depositary, National Institute of Advanced Industrial Science and Technology (AIST Tsukuba Central 6, 1-1-1 Higashi, Tsukubashishi Ibaraki, 305-8566, Japan) on Dec. 26, 2001.

The human CDR-grafted antibody means an antibody prepared by replacing CDRs of VH and VL of an antibody of a non-human animal with CDR sequences of an antibody of a non-human animal respectively in a human antibody.

The human CDR-grafted antibody used in the agent for preventing or treating arthritis of the present invention can be prepared by constructing DNAs encoding V regions in which CDR sequences of VH and VL of any human antibody are replaced with CDR sequences of VH and VL of an anti-FGF-8 neutralizing antibody of a non-human animal respectively, individually inserting them in a vector for expression in animal cells carrying genes encoding human antibody CH and human antibody CL to construct a human CDR-grafted antibody expression vector and introducing the vector into the animal cell for expression.

As CH of the human CDR-grafted antibodies, any CH of antibodies belonging to hIg may be used. CH of antibodies belonging to hIgG class is preferable, and any of subclasses such as γ1, γ2, γ3 and γ4 belonging to hIgG class may be used. As CL of the human CDR-grafted antibodies, any CL of antibodies belonging to hIg, for example, κ class or λ class, may be used.

The human CDR-grafted antibody which specifically binds to FGF-8 to inhibit activity of FGF-8 (hereinafter also referred to as an anti-FGF-8 neutralizing CDR-grafted antibody) includes a human CDR-grafted antibody comprising CDRs of VH and VL of a monoclonal antibody which specifically binds to FGF-8 to inhibit activity of FGF-8 and human antibody CH and CL, and a human CDR-grafted antibody comprising CDRs of VH and VL of a monoclonal antibody which specifically binds to FGF-8 to inhibit activity of FGF-8, framework regions (hereinafter abbreviated as FRs) of human antibody VH and VL, and human antibody CH and CL. Preferable examples thereof include (a) a human CDR-grafted antibody in which CDR1, CDR2 and CDR3 of VH comprise amino acid sequences represented by SEQ ID NOS. 7, 8 and 9 respectively, (b) a human CDR-grafted antibody in which CDR1, CDR2 and CDR3 of VL comprise amino acid sequences represented by SEQ ID NOS. 10, 11 and 12 respectively and (c) a human CDR-grafted antibody in which CDR1, CDR2 and CDR3 of VH comprise amino acid sequences represented by SEQ ID NOS. 7, 8 and 9 respectively and CDR1, CDR2 and CDR3 of VL comprise amino acid sequences represented by SEQ ID NOS. 10, 11 and 12 respectively. More preferable examples thereof include (a) a human CDR-grafted antibody in which VH comprises an amino acid sequence represented by SEQ ID NO. 18, (b) a human CDR-grafted antibody in which VL comprises an amino acid sequence represented by SEQ ID NO. 19, and (c) a human CDR-grafted antibody in which VH comprises an amino acid sequence represented by SEQ ID NO. 18 and VL comprises an amino acid sequence represented by SEQ ID NO. 19. Further preferable examples thereof include (a) a human CDR-grafted antibody in which VH comprises an amino acid sequence represented by SEQ ID NO. 18 in which at least one or more amino acid residue selected from Lys at position 12, Lys at position 13, Ala at position 40, Pro at position 41, Met at position 48, Val at position 68, Ile at position 70, Thr at position 74, Thr at position 76, Glu at position 82, Ser at position 84, Arg at position 87 and Tyr at position 95 is replaced with another amino acid residue, (b) a human CDR-grafted antibody in which VL comprises an amino acid sequence represented by SEQ ID NO. 19 in which at least one or more amino acid residue selected from Ile at position 2, Val at position 3, Thr at position 14, Pro at position 15, Gln at position 50, Leu at position 51 and Tyr at position 92 is replaced with another amino acid residue, and (c) a human CDR-grafted antibody in which VH comprises an amino acid sequence represented by SEQ ID NO. 18 in which at least one or more amino acid residue selected from Lys at position 12, Lys at position 13, Ala at position 40, Pro at position 41, Met at position 48, Val at position 68, Ile at position 70, Thr at position 74, Thr at position 76, Glu at position 82, Ser at position 84, Arg at position 87 and Tyr at position 95 is replaced with another amino acid residue, and VL comprises an amino acid sequence represented by SEQ ID NO. 19 in which at least one or more amino acid residue selected from Ile at position 2, Val at position 3, Thr at position 14, Pro at position 15, Gln at position 50, Leu at position 51 and Tyr at position 92 Tyr is replaced with another amino acid residue. Specific examples thereof include (a) a human CDR-grafted antibody in which VH comprises an amino acid sequence represented by SEQ ID NO. 18 or 20, (b) a human CDR-grafted antibody in which VL comprises an amino acid sequence represented by SEQ ID NO. 19, 21, 42, 43, 44, 45, 46, 47, 50 or 51, and (c) a human CDR-grafted antibody in which VH comprises an amino acid sequence represented by SEQ ID NO. 18 or 20 and VL comprises an amino acid sequence represented by SEQ ID NO. 19, 21, 42, 43, 44, 45, 46, 47, 50 or 51. Preferable examples thereof include (a) a human CDR-grafted antibody in which VH comprises an amino acid sequence represented by SEQ ID NO. 18 and VL comprises an amino acid sequence represented by SEQ ID NO. 21, (b) a human CDR-grafted antibody in which VH comprises an amino acid sequence represented by SEQ ID NO. 18 and VL comprises an amino acid sequence represented by SEQ ID NO. 44, and (c) a human CDR-grafted antibody in which VH comprises an amino acid sequence represented by SEQ ID NO. 18 and VL comprises an amino acid sequence represented by SEQ ID NO. 50. Examples of such a human CDR-grafted antibody include human CDR-grafted antibodies HV0LV6 and HV0LV6/CHO in which VH comprises an amino acid sequence represented by SEQ ID NO. 18, CH comprises an amino acid sequence of human γ1 subclass, VL comprises an amino acid sequence represented by SEQ ID NO. 21 and CL comprises an amino acid sequence of human κ class, human CDR-grafted antibody HV0LV3-1/CHO in which VH comprises an amino acid sequence represented by SEQ ID NO. 18, CH comprises an amino acid sequence of human γ1 subclass, VL comprises an amino acid sequence represented by SEQ ID NO. 44 and CL comprises an amino acid sequence of human κ class, and human CDR-grafted antibody HV0LV4-3/CHO in which VH comprises an amino acid sequence represented by SEQ ID NO. 18, CH comprises an amino acid sequence of human γ1 subclass, VL comprises an amino acid sequence represented by SEQ ID NO. 50 and CL comprises an amino acid sequence of human κ class.

Transformant KM8037 producing human CDR-grafted antibody HV0LV6 was deposited as FERM BP-8084 in International Patent Organism Depositary, National Institute of Advanced Industrial Science and Technology (AIST Tsukuba Central 6, 1-1-1 Higashi, Tsukubashi Ibaraki, 305-8566, Japan) on Jun. 20, 2002, transformant KM8036 which produces human CDR-grafted antibody HV0LV3-1 was deposited as FERM BP-8083 in International Patent Organism Depositary, National Institute of Advanced Industrial Science and Technology (AIST Tsukuba Central 6, 1-1-1 Higashi, Tsukubashi Ibaraki, 305-8566, Japan) on Jun. 20, 2002, and transformant KM8035 producing human CDR-grafted antibody HV0LV4-3 was deposited as FERM BP-8082 in International Patent Organism Depositary, National Institute of Advanced Industrial Science and Technology (AIST Tsukuba Central 6, 1-1-1 Higashi, Tsukubashi Ibaraki, 305-8566, Japan) on Jun. 20, 2002 respectively.

The anti-FGF-8 neutralizing antibody used in the agent for preventing or treating arthritis of the present invention includes also an antibody fragment. The antibody fragment includes Fab (abbreviated for fragment of antigen binding), F(ab')$_2$, Fab', a single-chain antibody (single chain Fv; hereinafter reffered to as scFv), a dimerized V region fragment (diabody), a disulfide stabilized antibody (disulfide stabilized Fv; hereinafter referred to as dsFv) and a CDR-containing peptide.

The Fab is a fragment having antigen-binding activity and comprising approximately a half of an N-terminal side of H chain and the whole L chain, the fragment being obtained by digesting upper peptide moieties of two disulfide bonds that crosslink two H chains in hinge regions of IgG with an enzyme papain having a molecular weight of approximately 50,000.

The F(ab')$_2$ is an antibody fragment obtained by treating lower moieties of two disulfide bonds in hinge regions of IgG with proteinase pepsin (cleaving in 234th amino acid residue of H chain) in which Fab is slightly larger than that bound through disulfide bonds in hinge regions having a molecular weight of approximately 100,000 and having antigen-binding activity.

The Fab' is a fragment obtained by cleaving disulfide bonds between hinges of F(ab')$_2$ having a molecular weight of approximately 50,000 and antigen-binding activity.

The scFv is a VH-P-VL or VL-P-VH polypeptide in which one VH and one VL are linked with an appropriate peptide linker (hereinafter referred to as P). As VH and VL comprised in scFv used in an agent for preventing or treating arthritis in the invention, any VH and VL of anti-FGF-8 neutralizing monoclonal antibodies can be used.

The diabody is an antibody fragment in which scFvs that have the same or different antigen-binding specificities form a dimer, and this is an antibody fragment having divalent antigen-binding activity to the same antigen or antigen-binding activities specific to different antigens respectively.

The dsFv is a fragment in which polypeptides with one amino acid residue of VH and one amino acid residue of VL replaced with cysteine residues are bound through a disulfide bond. The amino acid residue replaced with the cysteine residue can be selected by estimating a three-dimensional structure of an antibody according to the method indicated by Reiter et al. (Reiter Y. et al., Protein Eng., 7, 697-704, 1994). As VH or VL comprised in dsFv used in the agent for preventing or treating arthritis of the present invention, any VH and VL of anti-FGF-8 neutralizing monoclonal antibodies can be used.

The CDR-containing peptide used in the agent for preventing or treating arthritis of the present invention comprises at least one or more region of CDRs of VH and VL of the anti-FGF-8 neutralizing antibody. The peptide containing plural CDRs can be produced by binding them either directly or through an appropriate peptide linker.

A specific process for producing the anti-FGF-8 neutralizing antibody used of the present invention, a method for evaluating activity thereof, the agent for preventing or treating arthritis comprising the antibody, the diagnostic agent of arthritis comprising the anti-FGF-8 antibody and the method for diagnosing arthritis using the anti-FGF-8 antibody are described below.

1. Process for Producing the Anti-FGF-8 Neutralizing Antibody (Polyclonal Antibody, Monoclonal Antibody)

(1) Preparation of an Antigen

Examples of an antigen necessary for producing the anti-FGF-8 neutralizing antibody include a cell producing FGF-8 or its cell fraction, an FGF-8 protein, a partial fragment of the protein, a peptide having a partial sequence of an amino acid sequence of the protein, and the like.

The FGF-8 protein and the partial fragment of the protein can be produced as such or as a fusion protein intracellularly or in a culture supernatant by constructing a recombinant vector in which a full-length or partial fragment DNA encoding FGF-8 (Tanaka A. et al., Proc. Natl. Acad. Sci. USA, 89, 8928-8932, 1992, Tanaka A. et al., FEBS Lett., 363, 226-230, 1996) is inserted downstream of a promoter of an appropriate vector, introducing the recombinant vector into a host cell to obtain an FGF-8 expression cell and culturing the cell in an appropriate medium. The peptide having the partial sequence of the FGF-8 protein can be prepared using a peptide synthesizer.

The full-length or partial, fragment DNA encoding FGF-8 can be prepared by a polymerase chain reaction [hereinafter referred to as PCR; Sambrook J. et al., Molecular Cloning 3rd edition, Cold Spring Harbor Laboratory, 2001 (hereinafter referred to as "Molecular Cloning 3rd edition"), Ausubel F. M. et al., Current Protocols in Molecular Biology, John Wiley & Sons, 1987-2001 (hereinafter referred to as Current Protocols in Molecular Biology) using a cDNA prepares from cells expressing FGF-8, such as SC-3, as a template.

As a host, any of hosts may be used so long as a desired gene can be expressed therein, examples thereof being bacteria, yeasts, animal cells, insect cells and the like. Examples of bacteria include bacteria belonging to the genus *Escherichia* and the genus *Bacillus*, such as *Escherichia coli* and

*Bacillus subtilis*. Examples of yeasts include *Saccharomyces cerevisiae* and *Schizosaccharomyces pombe*. Examples of animal cells include a Namalwa cell being a human cell, a COS cell being a monkey cell, a CHO cell being a cell of Chinese hamster and the like. Examples of insect cells include Sf9 and Sf21 (manufactured by Pharmingen), High Five (manufactured by Invitrogen) and the like.

As the vector into which to introduce a full-length or partial fragment DNA encoding FGF-8, any of vectors can be used, so long as the DNA can be incorporated therein and expressed in a host cell.

When bacterium such as *Escherichia coli* is used as a host, the expression vector comprising a promoter, a ribosome-binding sequence, a full-length or partial fragment DNA encoding FGF-8, a transcription termination sequence and, as required, a promoter controlling sequence is preferable. Examples thereof include commercially available pGEX-2T (manufactured by Amersham Biosciences) and pET17b (manufactured by Novagen).

As a method for introducing a recombinant vector into bacteria, any method can both be used so long as a DNA is introduced into bacteria, for example, the method using calcium ion (Cohen S. N. et al., Proc. Natl. Acad. Sci., USA, 69, 2110-2114, 1972) and the protoplast method (Japanese published unexamined application No. 248394/88).

When yeasts is using as a host, for example, YEp13 (ATCC 37115), YEp24 (ATCC 37051) and YCp50 (ATCC 37419) are used as the expression vector.

As the method for introducing the recombinant vector into yeasts, any method can be used so long as a DNA is introduced into yeasts. Example includes the electroporation method (Becker D. M. and Guarente L., Methods, Enzymol., 194, 182-187, 1991), the spheroplast method (Hinnen A. et al., Proc. Natl. Acad. Sci. USA, 84, 1929-1933, 1978), the lithium acetate method (Ito H. et al., J. Bacteriol., 153, 163-168, 1983) and the like.

When an animal cell is using as a host, for example, pAGE107 (Japanese published unexamined application No. 22979/91; Miyaji H. et al., Cytotechnology, 3, 133-140, 1990) and pAGE103 (Mizukami T. and Itoh S., J. Biochem., 101, 1307-1310, 1987) are used as the expression vector.

Any promoter can be using, so long as it can be expressed in animal cells can be used. Examples include an IE (immediate early) gene promoter of cytomegalovirus (CMV), a promoter of SV40 or metallothionein, and the like. An enhancer of the IE gene of human CMV may be used along with the promoter.

As a method for introducing a recombinant vector into animal cells, any of methods in which a DNA is introduced into animal cells, such as the electroporation method (Miyaji H. et al., Cytotechnology, 3, 133-140, 1990), the calcium phosphate method (Japanese published unexamined application No. 227075/90) and the lipofection method (Felgner P. L. et al., Proc. Natl. Acad. Sci. USA, 84, 7413-7417, 1987), can be used.

When the insect cells are used as a host, a protein can be expressed by the method described in, for example, Current Protocols in Molecular Biology, O'Reilly et al., Baculovirus Expression Vectors: A Laboratory Manual, Oxford University Press, 1994 or the like. That is, the following recombinant gene introduction vector and baculovirus are co-introduced into insect cells to obtain a recombinant virus in the insect cells culture supernatant, and the insect cells are infected with the recombinant virus to obtain protein expression insect cells.

As the gene introduction vector, for example, pVL1392 and pVL1393 (both manufactured by Pharmingen), pBlue-Bac4.5 (manufactured by Invitrogen) and the like are used.

As the baculovirus, for example, *Autographa californica* nuclear polyhedrosis virus, a virus with which insects of the family *Noctuidae* are infected, is used.

As the method for co-introducing the recombinant gene introduction vector and the baculovirus for preparation of the recombinant virus, for example, the calcium phosphate method (Japanese published unexamined application No. 227075/90) and the lipofection method (Felgner P. L. et al., Proc. Natl. Acad. Sci. USA, 84, 7413-7417, 1987) and the like are used.

A protein may be produced by preparing a recombinant baculovirus using Baculo Gold Starter Kit manufactured by Pharmingen or the like and then infecting insect cells such as Sf9, Sf21, High Five and the like as mentioned above with the recombinant virus (Bio/Technology, 6, 47, 1988).

As the method for expressing the gene, the secretory production, the fusion protein expression and the like, besides the intracellular expression of the FGF-8 protein alone, have been developed, and any of these methods can be used. For example, the expression can be performed according to the method described in Molecular Cloning 3rd edition.

The thus-obtained transformant is cultured in a medium to form and accumulate the FGF-8 protein in the culture, and the FGF-8 protein is extracted from the culture, whereby the full length or the partial fragment of the FGF-8 protein can be produced as such or as a fusion protein.

The method for culturing the transformant in a medium is carried out according to an ordinary method used in culturing a host.

As the medium in for culturing the transformant obtained by using microorganisms such as *Escherichia coli* or yeast as a host, either a natural medium or a synthetic medium can be used, so long as it comprises carbon sources, nitrogen sources, inorganic salts and the like which can be assimilable by the microorganisms and culturing the transformants efficiently can be carried out (Molecular Cloning 3rd edition). The culturing is usually carried out under aerobic conditions such as shaking culture or submerged aeration-agitation culture at 15 to 40° C. for 16 to 96 hours. During the culturing, the pH is maintained at from 3.0 to 9.0. The pH is adjusted with an inorganic or organic acid, an alkaline solution, urea, calcium carbonate, ammonia or the like. If necessary, antibiotics such as ampicillin and tetracycline can be added to the medium during the culturing.

As the medium for culturing the transformant obtained by using animal cells as a host, RPMI 1640 medium, Eagle's MEM medium, these mediums containing fetal bovine serum (hereinafter abbreviated as FBS) and the like which are generally used are available. The culturing is usually carried out in the presence of 5% $CO_2$ at 35 to 37° C. for 3 to 7 days. If necessary, antibiotics such as kanamycin and penicillin can be added to the medium during the culturing.

As the medium for culture the transformant obtained by using insect cells as a host, TNM-FH medium (manufactured by Pharmingen), Sf900IISFM (manufactured by Invitrogen), EX-CELL400 and EX-CELL405 (both manufactured by JRH Biosciences) and the like which are generally used are available. The culturing is carries out at 25 to 30° C. for 1 to 4 days. If necessary, antibiotics such as gentamicin can be added to the medium during the culturing.

In the foregoing culturing of the animal cells and the insect cells, it is preferable, if possible, to use a serum-free medium for facilitating purification of the full length or the partial fragment of FGF-8 as such or as a fusion protein.

When the full length or the partial fragment of FGF-8 is accumulated inside host cells as such or as a fusion protein, the cells are centrifuged after completion of the culturing, suspended in an aqueous buffer, and the ultrasonic disruption method, the French press method or the like. The protein is recovered from the supernatant obtained by centrifugation.

Also, when insolved body is formed intracellularly, a protein can be made into three-dimensional structure by diluting or dialyzing the solubilized solution in at such a concentration of the protein denaturing agent that does not denature protein or without the protein denaturing agent, after solibilized with a protein denaturing agent.

When the full length or the partial fragment of the FGF-8 protein or the fusion protein of these proteins is secreted extracellularly, the expressed protein can be recovered from the culture supernatant.

The isolation and purification can be carried out by using separation procedures such as solvent extraction, fractional precipitation by an organic solvent, salting-out, dialysis, centrifugation, ultrafiltration, ion exchange chromatography, gel filtration chromatography, hydrophobic chromatography, affinity chromatography, reversed phase chromatography, crystallization and electrophoresis alone or in combination.

The peptide having a partial sequence of the amino acid sequence of FGF-8 can be produced by the chemical synthesis methods such as the Fmoc (fluorenylmethyloxycarbonyl) method and the tBoc (t-butyloxycarbonyl) method. It can also be produced using peptide synthesizers of Advanced ChemTech, Applied Biosystems, Protein Technologies, Shimadzu Corporation and the like.

(2) Immunization of Animals and Preparation of Antibody-Producing Cells

Animals are immunized using the above-obtained protein as an antigen. With respect to the immunization method, the antigen may directly be administered to animals subcutaneously, intravenously or intraperitoneally. It is preferable to administer the antigen combined with a carrier protein having high immunogenicity or administer the antigen along with an appropriate adjuvant.

Examples of the carrier protein include Keyhole limpet hemocyanin, bovine serum albumin, bovine thyroglobulin and the like. Examples of the adjuvant include Complete Freund's Adjuvant, aluminum hydroxide gel, pertussis bacteria vaccine and the like.

Examples of immunized animals include non-human mammals such as rabbits, goats, mice, rats and hamsters.

The antigen is administered, after the first administration, 3 to 10 times every 1 to 2 weeks. The dose of the antigen is preferably 50 to 100 μg per animal. The blood sample is collected from the venous plexus of the fundus of the eye or the tail vein of the immunized animal 3 to 7 days after each administration. The specific binding ability with the antigen of the serum is confirmed by enzyme immunoassay [Koso Men-eki Sokuteiho, 3rd edition, Igaku Shoin, 1987, Antibodies A Laboratory Manual (Chapter 14), Goding J. W., Monoclonal Antibodies: Principles and Practice, Academic Press, 1996 (hereinafter abbreviated as Monoclonal Antibodies] or the like as described below.

The enzyme immunoassay can be performed as follows.

An antigen protein or cells with an antigen protein expressed are coated on a plate, and reacted with a serum collected from immunized animals as a first antibody. After the reaction of the first antibody, the plate is washed, and a second antibody is added thereto. After the reaction, a detection reaction corresponding to a substance labeled with the second antibody is carried out, and an antibody titer is measured.

The second antibody is an antibody capable of recognizing the first antibody, which is labeled with an enzyme such as peroxidase or biotin. Specifically, when a mouse is used as the immunized animal, an antibody capable of recognizing mouse immunoglobulin is used as the second antibody.

Non-human mammals in which the serum shows a sufficiently antibody titer are used as a supply source of antibody-producing cells.

After 3 to 7 days from the final administration of the antigen, lymphocytes are extracted from the immunized animals to fuse them with myeloma cells, according to the known method (Antibodies A Laboratory Manual).

The polyclonal antibody can be prepared by separating and purifying the serum. Whether the polyclonal antibody has the neutralizing activity to inhibit the activity of FGF-8 can be examined by cell growth inhibition assay described in 1. (4) below.

The monoclonal antibody can be prepared by fusing the antibody-producing cells with the myeloma cells derived from non-human mammals to produce hybridomas, culturing the hybridomas or administering the hybridomas to animals to from ascitic tumor of the cells and separating and purifying the culture solution or the ascitic fluid.

The antibody-producing cells can be extracted from spleen cells, lymph nodes, peripheral bloods and the like of the antigen-administered non-human mammals.

(3) Preparation of Myeloma Cells

As the myeloma cells, any of myeloma cells capable of growth in vitro, such as 8-azaguanine-resistant mouse (derived from BALB/c) myeloma cell lines P3-X63Ag8-U1 (Kohler G and Milstein C, Eur. J. Immunol., 6, 511-519, 1976), SP2/0-Ag14 (Shulman M. et al., Nature, 276, 269-270, 1978), P3-X63-Ag8653 (Kearney J. F. et al., J. Immunol., 123, 1548-1550, 1979) and P3-X63-Ag8 (Kohler G and Milstein C, Nature, 256, 495-497, 1975) which are established cell lines obtained from a mouse, can be used. With respect to the culturing and the subculturing of these cell lines, the number of cells up to at least $2 \times 10^7$ cells or more is secured until the cell fusion according to the known method (Antibodies A Laboratory Manual).

(4) Cell Fusion and Selection of a Monoclonal Antibody

The above-obtained antibody-producing cells and myeloma cells are washed, and a cell aggregating medium such as polyethylene glycol-1000 (PEG-1000) is added thereto to fuse the cells. The fused cells are suspended in a medium. The cells are washed using MEM medium, PBS (1.83 g/L $Na_2HPO_4$, 0.21 g/L $KH_2PO_4$, 7.65 g/L NaCl, pH 7.2) or the like. As the medium in which to suspend the fused cells, HAT medium [medium obtained by adding 100 μmol/L hypoxanthine, 15 μmol/L thymidine and 0.4 μmol/L aminopterin to a normal medium (RPMI 1640 medium containing 1.5 mol/L glutamine, 50 μmol/L 2-mercaptoethanol, 10 g/mL gentamicin and 10% FBS) is used to selectively obtain desired fused cells alone.

After the culturing, a part of the culture supernatant is sampled, and reacted with an antigen protein by the following enzyme immunoassay to select a sample that is not reacted with a non-antigen protein. Subsequently, cloning is performed by the limiting dilution method, and the cell in which a high antibody titer is stably measured by the enzyme immunoassay is selected as a monoclonal antibody-producing hybridoma cell line which specifically binds to FGF-8.

The enzyme immunoassay is performed as described in 1. (2) except that the hybridoma culture supernatant or a purified antibody obtained by a method to be described later is used as the first antibody.

The specific binding between the monoclonal antibody and FGF-8 can also be evaluated by the surface plasmon resonance (Karlsson R. et al., J. Immunol. Methods, 145, 229-240, 1991).

Specific examples of the anti-FGF-8 monoclonal antibody include monoclonal antibody KM1334 produced by hybridoma KM1334 (FERM BP-5451) belonging to mouse IgG1 subclass as described in Japanese published unexamined application No. 271391/97.

Whether the anti-FGF-8 monoclonal antibody produced by the above-selected hybridoma can inhibit the activity of FGF-8 is examined by growth inhibition assay using, as a target cell, mouse breast cancer cell line SC-3 (Nakamura N. et al., J. Steroid Biochem., 27, 459-464, 1987), mouse fibroblast NIH/3T3 (ATCC No. CRL-1658) or human prostatic cancer cell line LNCaP (ATCC No: CRL-1740). In the method, when the target cell is cultured in a medium containing FGF-8 (from 1 to 100 ng/mL) or testosterone, the culture supernatant or the anti-FGF-8 monoclonal antibody purified according to the method described in 2. (5) below is stepwise diluted to a final concentration of 0.001 to 100 g/mL, and added to the medium. After the culturing for 24 to 72 hours, the number of living cells is measured using an MTT [3-(4, 5-dimethyl-2-thiazol-2-yl)-2,5-diphenyl-2H-tetrazoli um bromide] solution, a cell counting kit, WST-1 Kit or the like. When the number of living cells is decreased dependently on the concentration of the anti-FGF-8 monoclonal antibody in comparison to the case of not adding the anti-FGF-8 monoclonal antibody, it can be confirmed that the anti-FGF-8 monoclonal antibody is an anti-FGF-8 neutralizing antibody that inhibits the activity of FGF-8.

The activity of inhibiting the binding of FGF-8 to the receptor on the cell surface by the anti-FGF-8 monoclonal antibody can be measured by the Bolton-Hunter method (Bolton A. E. and Hunter W. M., Biochem. J., 133, 529-539, 1973) or the like using a system of measuring the binding of $^{125}$I-labeled FGF-8 to the foregoing cell line.

The foregoing monoclonal antibody KM1334 is an anti-FGF-8 neutralizing antibody having the activity of inhibiting the FGF-8 activity, and it is preferable as the agent for preventing or treating arthritis.

(5) Preparation of a Monoclonal Antibody

Monoclonal antibody-producing hybridoma cells are intraperitoneally administered to 8- to 10-week-old mice or nude mice fed for 2 weeks by intraperitoneally administering 0.5 mL of a culture solution formed by culturing hybridoma cells or Pristane (2,6,10,14-tetramethylpentadecane) to cause ascitic canceration, and the monoclonal antibody can be prepared by being separated and purified from the resulting ascitic fluid.

As the method for separating and purifying the monoclonal antibody, centrifugation, salting-out with 40 to 50% saturated ammonium sulfate, method of caprylic acid precipitation, chromatographies using DEAE-Sepharose column, anion exchange column, protein A- or G-column and gel filtration column, and the like are used alone or in combination. The purified monoclonal antibody can be obtained by recovering the IgG or IgM fraction by this method.

The subclass of the purified monoclonal antibody can be determined using a monoclonal antibody typing kit or the like. The amount of the protein can be calculated by the Lowry method or absorbance at 280 nm.

The subclass of the antibody is an isotype of the class. Examples thereof include IgG1, IgG2a, IgG2b and IgG3 in mouse, and IgG1, IgG2, IgG3 and IgG4 in humans. Especially mouse IgG1 and IgG2a types and human IgG1 type have complement-dependent cytotoxic activity and antibody-dependent cytotoxic activity, and are useful in the therapeutic application.

2. Process for Producing an Anti-FGF-8 Neutralizing Humanized Antibody (1) Construction of a Vector for Expression of Humanized Antibody A vector for expression of humanized antibody necessary for producing a humanized antibody from an antibody of a non-human animal is constructed. The vector for expression of humanized antibody is a vector for expression in animal cells having inserted therein genes encoding CH and CL which are C regions of a human antibody, and can be constructed by inserting genes encoding CH and CL of a human antibody in a vector for expression in animal cells.

The C regions of the human antibody can be CH and CL of any human antibody. Examples thereof include CH of γ1 subclass, CH of γ4 subclass and CL of κ class of a human antibody, and the like. As DNAs encoding CH and CL of a human antibody, chromosomal DNAs comprising exons and introns can be used, and cDNAs are also available. As the vector for expression in animal cells, any of vectors can be used so long as genes encoding C regions of a human antibody can be inserted and expressed therein.

Examples thereof include pAGE107 (Japanese published unexamined application No. 22979/91; Miyaji H. et al., Cytotechnology, 3, 133-140, 1990), pAGE103 (Mizukami T. and Itoh S., J. Biochem., 101, 1307-1310, 1987), pHSG274 (Brady G. et al., Gene, 27, 223-232, 1984), PKCR(O'Hare K. et al., Proc. Natl. Acad. Sci. USA., 78, 1527-1531, 1981), pSG1βd2-4 (Miyaji H. et al., Cytotechnology, 4, 173-180, 1990) and the like. Examples of a promoter and an enhancer used in the vector for expression in animal cell include initial promoter and enhancer of SV40 (Mizukami T. and Itoh S., J. Biochem., 101, 1307-1310, 1987), LTR promoter and enhancer of Moloney mouse leukemia virus (Kuwana Y. et al., Biochem. Biophys. Res. Commun., 149, 960-968, 1987) and a promoter (Mason J. O. et al., Cell, 41, 479-487, 1985) and an enhancer (Gillies S. D. et al., Cell, 33, 717-728, 1983) of immunoglobulin H chain, and the like.

As the vector for expression of humanized antibody, a type in which antibody H chain and L chain are present in different vectors or a type in which they are present in one and the same vector (tandem-type) can both be used. A tandem-type vector for expression of humanized antibody is preferable in view of ease of construction of the humanized antibody expression vector, ease of introduction into animal cells and a balance of the amount of the expressed antibody H chain and L chain in animal cells (Shitara K. et al., J. Immunol. Methods, 167, 271-278, 1994). Examples of the tandem-type vector for expression of humanized antibody include pKANTEX93 (WO 97/10354), pEE18 (Bentley K. J. et al, Hybridoma, 17, 559-567, 1998) and the like.

The constructed vector for expression of humanized antibody can be used in the expression of a human chimeric antibody and a human CDR-grafted antibody in animal cells.

(2) Preparation of DNAs Encoding VH and VL of an Anti-FGF-8 Neutralizing Antibody of a Non-human Animal DNAs encoding VH and VL of an anti-FGF-8 neutralizing antibody of a non-human animal, for example, a mouse anti-FGF-8 neutralizing monoclonal antibody are obtained as follows.

mRNA are extracted from cells producing a mouse anti-FGF-8 neutralizing monoclonal antibody, for example, hybridomas producing a mouse FGF-8 neutralizing antibody, and cDNAs are synthesized. The synthesized cDNAs are inserted into vectors such as phages or plasmids to produce a cDNA library. From this library, a recombinant phage or a recombinant plasmid having a cDNA encoding VH and a recombinant phage or a recombinant plasmid having a cDNA encoding VL are isolated respectively using a C region moiety or a V region moiety of a mouse antibody as a probe.

The full length nucleotide sequences of VH and VL in the recombinant phage or the recombinant plasmid are determined, and the full length amino acid sequences of VH and VL are estimated from the nucleotide sequences.

As a non-human animal, any of animals capable of producing hybridomas, such as mice, rats, hamsters and rabbits, can be used. The process for preparing total RNAs from hybridomas includes the guanidine thiocyanate-cesium trifluoroacetate method (Okayama H. et al., Methods Enzymol., 154, 3-28, 1987), and the process for preparing mRNAs from total RNAs includes the oligo (dT) immobilization cellulose column method (Molecular Cloning 3rd edition) or the like. Examples of a kit for preparing mRNAs from hybridomas include FastTrack mRNA Isolation Kit (manufactured by Invitrogen), QuickPrep mRNA Purification Kit (manufactured by Amersham Biosciences) and the like.

Examples of a process for synthesizing cDNAs and producing a cDNA library include the usual process (Molecular Cloning 3rd edition; Current Protocols in Molecular Biology) and the process using commercially available kits such as SuperScript Choice System for cDNA Synthesis (manufactured by Invitrogen), ZAP-cDNA Synthesis Kit (manufactured by Stratagene) and TimeSaver cDNA Synthesis Kit (manufactured by Amersham Biosciences).

As a vector in which to incorporate a cDNA synthesized using an mRNA extracted from a hybridoma as a template in producing a cDNA library, any of vectors capable of subcloning the cDNA can be used. Examples thereof include phage and plasmid vectors such as ZAP Express (manufactured by Stratagene), pBluescript II SK(+) (manufactured by Stratagene), λZAPII (manufactured by Stratagene), λgt10 (manufactured by Stratagene), λgt11 (manufactured by Stratagene), Lambda BlueMid (manufactured by Clontech), λExCell (manufactured by Amersham Biosciences), pcD2 (Okayama H. and Berg P., Mol. Cell. Biol., 3, 280-289, 1983) and pUC18 (Yanisch-Perron C. et al., Gene 33, 103-119, 1985).

As *Escherichia coli* in which to introduce the cDNA library constructed by the phage or plasmid vector, any *Escherichia coli* capable of introducing, expressing and maintaining the cDNA library can be used. Examples thereof include XL1-Blue MRF' (manufactured by Stratagene), C600 (Appleyard R. K. Genetics, 39, 440-452, 1954), Y1088 (Young R. A. and Davis R., Science, 222, 778-782, 1983), Y1090 (Young R. A. and Davis R., Science, 222, 778-782, 1983), NM522 (Gough J. A. and Murray N. E., J. Mol. Biol., 166, 1-19, 1983), K802 (Wood W. B., J. Mol. Biol., 16, 118-133, 1966), JM105 (Yanisch-Perron C. et al., Gene, 33, 103-119, 1985) and the like.

The cDNA clones encoding VH and VL of the anti-FGF-8 neutralizing antibody of the non-human animal can be selected from the cDNA library by the colony hybridization method or the plaque hybridization method using an isotope or fluorescence-labeled probe (Molecular Cloning 3rd edition). Further, cDNAs encoding VH and VL can also be prepared through PCR using prepared primers and using cDNAs or a cDNA library synthesized from mRNAs as a template.

The nucleotide sequences of the cDNAs selected by the foregoing method can be determined by a reaction based on the di-deoxy method (Sanger F. et al., Proc. Natl. Acad. Sci. USA, 74, 5463-5467, 1977) using the cDNAs cloned in an appropriate vector and analysis using a DNA sequencer such as ABI377 (manufactured by Applied Biosystems) or the like.

(3) Analysis of Amino Acid Sequences of VH and VL of an Anti-FGF-8 Neutralizing Antibody of a Non-human Animal and Identification of Amino Acid Sequences of CDRs The full length amino acid sequences of VH and VL encoded by the cDNAs are estimated from the nucleotide sequences of the cDNAs obtained and determined in 2. (2), and it can be confirmed whether the resulting cDNAs encode the full length amino acid sequences of VH and VL of an antibody containing a secretory signal sequence in comparison to the full length amino acid sequences of VH and VL of the known antibody (Sequences of Proteins of Immunological Interest, US Dept. Health and Human Services, 1991, hereinafter referred to as "Sequences of Proteins of Immunological Interest"). With respect to the full length amino acid sequences of VH and VL of the antibody containing the secretory signal sequence, it is possible to estimate the length of the secretory signal sequence and the N-terminal amino acid sequence and know subgroups to which they belong in comparison to the full length amino acid sequences of VH and VL of the known antibody (Sequences of Proteins of Immunological Interest).

The novelty of the sequences can be examined by performing search for homology of the full length amino acid sequences of the resulting VH and VL using a homology search program such as BLAST (Altschul S. F. et al., J. Mol. Biol., 215, 403-410, 1990) or the like with respect to any database, for example, SWISS-PROT or PIR-Protein.

VH and VL that form antigen-binding sites of an antibody comprise four FRs with relatively conserved sequences and three CDRs (CDR1, CDR2, CDR3) with varied sequences linking them (Sequences of Proteins of Immunological Interest). The amino acid sequences of CDRs of VH and VL can be identified in comparison to amino acid sequences of V regions of the known antibody (Sequences of Proteins of Immunological Interest).

(4) Construction of an Anti-FGF-8 Neutralizing Chimeric Antibody Expression Vector The anti-FGF-8 neutralizing chimeric antibody expression vector can be constructed by inserting DNAs encoding VH and VL of the anti-FGF-8 neutralizing antibody of the non-human animal uptream of genes encoding CH and CL of the human antibody of the vector for expression of humanized antibody constructed in 2.(1). For example, VH and VL of the anti-FGF-8 neutralizing antibody of the non-human animal are amplified by the PCR method using a plasmid having DNAs encoding VH and VL of the antibody as a template and primers on the 5'-terminal side and the 3'-terminal side, the primers comprising recognition sequences of appropriate restriction endonucleases and nucleotide sequences encoding V regions. The respective amplified products are cloned into a plasmid such as pBluescript II SK(−) (manufactured by Stratagene) and the nucleotide sequences are determined by the method described in 2. (0.2) to obtain a plasmid having the DNA sequences encoding the amino acid sequences of VH and VL of the anti-FGF-8 neutralizing antibody. The DNAs encoding the amino acid sequences of VH and VL of the anti-FGF-8 neutralizing antibody are isolated from the resulting plasmid, cloned upstream of the genes encoding CH and CL of the human antibody of the vector for expression of humanized antibody described in 2.(1) such that these are expressed in an appropriate from. In this manner, the anti-FGF-8 neutralizing chimeric antibody expression vector can be constructed.

(5) Construction of DNAs Encoding V Regions of an Anti-FGF-8 Neutralizing CDR-grafted Antibody DNAs encoding VH and VL of the anti-FGF-8 neutralizing CDR-grafted antibody can be constructed as follows. First, amino acid sequences of FRs of VH and VL of a human antibody on which to graft amino acid sequences of CDRs of VH and VL of the anti-FGF-8 neutralizing antibody of the non-human animal are selected. As the amino acid sequences of FRs of VH and VL of the human antibody, any of amino acid sequences derived from the human antibody can be used. Examples thereof include amino acid sequences of VH and VL of the human antibody registered in data nucleotide such as Protein Data Bank and consensus amino acid sequences of subgroups of FRs of VH and VL of the human antibody (Sequences of Proteins of Immunological Interest). Among these, it is preferable to select amino acid sequences having as high a homology to the amino acid sequences of FRs of VH and VL of the anti-FGF-8 neutralizing antibody of the non-human animal as possible, preferably amino acid sequences having a homology thereto by 60% or more for producing the human CDR-grafted antibody having the sufficiently activity.

Subsequently, the desired amino acid sequences of CDRs of VH and VL of the anti-FGF-8 neutralizing antibody of the non-human animal are grafted on the selected amino acid sequences of FRs of VH and VL of the human antibody to design the amino acid sequences of VH and VL of the anti-FGF-8 neutralizing CDR-grafted antibody. The designed amino acid sequences are converted to nucleotide sequences in consideration of the codon frequency found in the nucleotide sequences of the genes of the antibody (Sequences of Proteins of Immunological Interest) to design the nucleotide sequences encoding the amino acid sequences of VH and VL of the anti-FGF-8 neutralizing CDR-grafted antibody. According to the designed nucleotide sequences, several synthetic DNAs having a length of 100 to 150 bases are synthesized, and PCR is carried out using them. In this case, it is preferable to design four synthetic DNAs of each of VH and VL in view of PCR reaction efficiency and length of DNAs that can be synthesized. Further, DNAs can easily be cloned in the vector for expression of humanized antibody constructed in 2. (1) by introducing recognition sequences of appropriate restriction endonucleases on the 5'-terminals of the synthetic DNAs located at the both ends. After the PCR reaction, the amplified products are cloned in a plasmid vector such as pBluescript SK(-) (manufactured by Stratagene), and the nucleotide sequences are determined by the method described in 2. (2) to obtain the plasmid having the nucleotide sequences encoding the amino acid sequences of VH and VL of the desired anti-FGF-8 neutralizing CDR-grafted antibody.

(6) Modification of Amino Acid Sequences of VH and VL of an Anti-FGF-8 Neutralizing CDR-grafted Antibody It is known that the antigen-binding activity of the desired human CDR-grafted antibody is decreased as compared to the original activity of the antibody of the non-human animal by grafting only CDRs of VH and VL of the antibody of the non-human animal on FRs of VH and VL of the human antibody (Tempest P. R. et al., Bio/technology, 9, 266-271, 1991). With respect to its cause, some amino acid residues of not only CDRs but also FRs are involved in the antigen-binding activity directly or indirectly in VH and VL of the original antibody of the non-human animal, and these amino acid residues are considered to be changed to another amino acid residues of FRs of VH and VL of the human antibody according to the grafting of CDRs. In order to solve this problem, in the human CDR-grafted antibody, the amino acid residues which are directly involved in the binding to the antigen or the amino acid residues which interact with the amino acid residues of CDRs or maintain the three-dimensional structure of the antigen and are indirectly involved in the binding to the antigen are identified in the amino acid sequences of FRs of VH and VL of the human antibody, and they are replaced with amino acid residues found in the original antibody of the non-human animal to increase the decreased antigen-binding activity (Tempest P. R. et al., Bio/technology, 9, 266-271, 1991). In the production of the human CDR-grafted antibody, the most important point is how efficiently the amino acid resides of FRs involved in the antigen-binding activity are identified. To this end, the construction and the analysis of the three-dimensional structure of the antibody are performed by X-ray crystallography (Bernstein F. C. et al., J. Mol. Biol., 112, 535-542, 1977), computer modeling (Tempest P. R. et al., Protein Engineering, 7, 1501-1507, 1994) or the like. The information of the three-dimensional structure of the antibody obtained by these methods has provided a lot of useful information in the production of the human CDR-grafted antibody. Meanwhile, a process for producing a human CDR-grafted antibody which can be applied to any antibodies has not yet been established. At present, various trial-and-error testings are required in which several types of variants are produced for the respective antibodies and the interrelation of the antigen-binding activities thereof are examined.

The modification of the amino acid residues of FRs of VH and VL of the human antibody can be achieved by performing PCR method using synthetic DNAs as primers for mutagenesis. With respect to the amplified products after PCR, the nucleotide sequences thereof are determined by the method described in 2. (2) to confirm that the desired modification has been carried out, whereby the vector comprising DNAs with the desired modification introduced (hereinafter referred to as an amino acid sequence-modified vector) is obtained.

The modification of the amino acid sequences in a narrow region is performed by the mutagenesis methods of PCR using mutagenesis primers comprising 20 to 35 bases. Specifically, a sense mutagenesis primer and an antisense mutagenesis primer comprising 20 to 35 bases and comprising DNA sequences encoding amino acid residues after the modification are synthesized, and two-step PCR is performed using a plasmid comprising DNAs encoding amino acid sequences of VH and VL to be modified as a template. After the final amplified fragment is subcloned into an appropriate vector, its nucleotide sequence is determined to obtain an amino acid sequence-modified vector comprising DNAs with the desired mutagenesis.

(7) Construction of an Anti-FGF-8 Neutralizing CDR-Grafted Antibody Expression Vector The anti-FGF-8 neutralizing CDR-grafted antibody expression vector can be constructed by inserting DNAs encoding VH and VL of the anti-FGF-8 neutralizing CDR-grafted antibody constructed in 2.(5) and (6) into upstream of DNAs encoding CH and CL of the human antibody of the vector for expression of humanized antibody described in 2.(1). For example, recognition sequences of appropriate restriction endonucleases are introduced into the 5'-terminals of the synthetic DNAs located at the both ends among the synthetic DNAs used to construct VH and VL of the anti-FGF-8 neutralizing CDR-grafted antibody in 2. (5) and (6), whereby the cloning can be performed such that these are expressed in an appropriate form upstream of DNAs encoding CH and CL of the human antibody of the vector for expression of humanized antibody described in 2.(1).

(8) Transient Expression of a Humanized Antibody and Evaluation of its Activity

In order to efficiently evaluate the antigen-binding activity of many types of the humanized antibodies produced, the transient expression of the humanized antibodies can be carried out using the anti-FGF-8 neutralizing chimeric antibody expression vector described in 2. (4), the anti-FGF-8 neutralizing CDR-grafted antibody expression vector described in 2. (7) or modified expression vectors thereof. As the host cell in which to introduce the expression vector, any of host cells capable of expressing the humanized antibody can be used. COS-7 cell (ATCC No: CRL-1651) is generally used owing to its large expression amount (Warr G. W. et al., Methods in Nucleic Acids Research, CRC Press, 283, 1990). Examples of the method for introducing the expression vector into COS-7 cell include the DEAE-dextran method (Warr G. W. et al., Methods in Nucleic Acids Research, CRC press, 283, 1990) and the lipofection method (Felgner P. L. et al., Proc. Natl. Acad. Sci. USA, 84, 7413-7417, 1987).

After the introduction of the expression vector, the expression amount of the humanized antibody in the culture supernatant and the antigen-binding activity thereof can be measured by the enzyme immunoassay, as described in 1. (2), using the culture supernatant as the first antibody and the labeled anti-human immunoglobulin antibody as the second antibody, or the like. Further, whether the neutralizing activity by which to inhibit the FGF-8 activity is retained or not can be confirmed by the cell growth inhibition assay described in 1. (4).

(9) Stable Expression of a Humanized Antibody and Evaluation of its Activity

A transformant that stably produces the humanized antibody can be obtained by introducing the anti-FGF-8 neutralizing chimeric antibody expression vector described in 2. (4) or the anti-FGF-8 neutralizing CDR-grafted antibody expression vector described in 2. (7) into an appropriate host cell.

The method for introducing the expression vector into the host cell includes the electroporation method (Japanese published unexamined application No. 257891/90; Miyaji H. et al., Cytotechnology, 3, 133-140, 1990).

As the host cell in which to introduce the anti-FGF-8 neutralizing chimeric antibody expression vector or the anti-FGF-8 neutralizing CDR-grafted antibody expression vector, any of host cells capable of expressing the humanized antibody can be used. Examples thereof include mouse SP2/0-Ag14 cell (ATCC No: CRL-1581), mouse P3X63-Ag8.653 cell (ATCC No: CRL-1580), CHO/DG44 cell (Urlaub G. and Chasin L. A., Proc. Natl. Acad. Sci. USA, 77, 4216-4220 1980) which is a CHO cell deficient in dihydrofolic acid reductase (hereinafter abbreviated as DHFR) gene, rat YB2/3HL.P2.G11.16Ag.20 cell (ATCC No: CRL-1662, hereinafter referred to as YB2/0 cell), and the like.

The transformant that stably produces the humanized antibody after the introduction of the expression vector can be selected by the culturing in an animal cell culture medium containing a compound such as G418 (G418 sulfate; manufactured by Sigma-Aldrich) (Shitara K. et al., J. Immunol. Methods, 167, 271-278, 1994). As the animal cell culture medium, RPMI 1640 medium (manufactured by Nissui Pharmaceutical), GIT medium (manufactured by Nippon Seiyaku), EX-CELL302 medium (manufactured by JRH Biosciences), IMDM medium (manufactured by Invitrogen), hybridoma-SFM medium (manufactured by Invitrogen), these mediums containing additives such as FBS, and the like can be used. The humanized antibody can be expressed and accumulated in the culture supernatant by culturing the resulting transformant in the medium. The expression amount of the humanized antibody in the culture supernatant and the antigen-binding activity thereof can be measured by ELISA described in 1. (4) or the like. The transformant can increase the amount of the humanized antibody produced using a DHFR gene amplification system or the like (Shitara K. et al., J. Immunol. Methods, 167, 271-278, 1994).

The humanized antibody can be purified from the culture supernatant of the transformant using protein A column (Antibodies A Laboratory Manual, chapter 8; Monoclonal Antibodies). Further, an ordinary purification method used in proteins is also available. For example, it can be purified by a combination of gel filtration, ion exchange chromatography, ultrafiltration and the like. The molecular weights of H chain, L chain and the whole antibody molecular weight of the purified humanized antibody are measured by the polyacrylamide gel electrophoresis (SDS-PAGE; laemmli U. K. Nature, 227,680-685, 1970), the Western blotting method (Antibodies A Laboratory Manual, chapter 12; Monoclonal Antibodies) or the like.

The antigen-binding activity of the purified humanized antibody can be measured by the enzyme immunoassay using the purified humanized antibody as the first antibody and the labeled anti-human immunoglobulin antibody as the second antibody as described in above 1, (2), the surface plasmon resonance (Karlsson R. et al., J. Immunol. Methods, 145, 229-240, 1991) or the like. Whether the neutralizing activity by which to inhibit the FGF-8 activity is retained or not can be confirmed by the cell growth inhibition assay described in 1. (4).

3. Preparation of an Antibody Fragment

The antibody fragment can be produced by the genetic engineering method or the protein chemical method using the anti-FGF-8 neutralizing monoclonal antibody and the anti-FGF-8 neutralizing humanized antibody described in 1. and 2. Examples of the antibody fragment include Fab, $F(ab')_2$, Fab', scFv, diabody, dsFv and CDR-containing peptide.

(1) Preparation of Fab

Fab can be prepared by treating the anti-FGF-8 neutralizing antibody with a protease, papain. After the treatment with papain, the fragment is passed through protein A column when the original antibody is an antibody of IgG subclass having the binding activity to protein A, whereby the fragment can be recovered as uniform Fab by being separated from IgG molecules or Fc fragments (Monoclonal Antibodies). In case of an antibody of IgG subclass having no binding activity for protein A, Fab can be recovered from a fraction eluted at a low salt concentration by ion exchange chromatography (Monoclonal Antibodies). Further, Fab can be prepared by the genetic engineering method using *Escherichia coli*. For example, a Fab expression vector can be constructed by cloning the DNAs encoding V regions of the antibodies described in 2. (2), (5) and (6) in a vector for expression of Fab. As the vector for expression of Fab, any of vectors capable of inserting and expressing DNAs for Fab can be used. Examples thereof include pIT106 (Better M. et al., Science, 240, 1041-1043, 1988) and the like. It is possible that the Fab expression vector is introduced into appropriate *Escherichia coli* and Fab is produced and accumulated in an inclusion body or a periplasmic space. Active Fab can be obtained from the inclusion body by the refolding method which is commonly used in proteins. When Fab is expressed in periplasmic space, active Fab is leaked in the culture supernatant. After the refolding or from the culture supernatant, uniform Fab can be purified using a column immobilized with an antigen (Borrebeck K., Antibody Engineering: A practical Guide, Oxford University Press, 1991).

(2) Preparation of $F(ab')_2$ $F(ab')_2$ can be prepared by treating the anti-FGF-8 neutralizing antibody with a protease, pepsin. After the treatment with pepsin, the fragment can be recovered as uniform $F(ab')_2$ by the same purification procedure as used in Fab (Monoclonal Antibodies). Further, it can also be prepared by a method in which Fab' described in 3. (3) is treated with a maleimide such as N,N'-o-phenylenedimaleimide or bismaleimidehexane to form thioether linkage or a method in which it is treated with 5,5'-dithiobis(2-nitrobenzoic acid) to form disulfide bond (McCafferty J. et al., Antibody Engineering: A Practical Approach, IRL Press, 1996).

(3) Preparation of Fab'

Fab' can be prepared by treating F(ab')$_2$ described in 3.(2) with a reducing agent such as dithiothreitol. Further, Fab' can also be prepared by the genetic engineering method using *Escherichia coli*. For example, a Fab' expression vector can be prepared by cloning the DNAs encoding V regions of the antibodies described in 2. (2), (5) and (6) in a vector for expression of Fab'. As the vector for expression of Fab', any of vectors capable of inserting and expressing the DNAs encoding V regions of the antibodies described in 2. (2), (5) and (6) can be used. Examples thereof include pAK19 (Carter P. et al., Bio/technology, 10, 163-167, 1992) and the like. It is possible that the Fab' expression vector is introduced into appropriate *Escherichia coli* and Fab' is produced and accumulated in an inclusion body or a periplasmic space. Active Fab' can be obtained from the inclusion body by the refolding method which is commonly used in proteins. When Fab' is expressed in the periplasmic space, cells can be disrupted by treatment such as partial digestion with lysozyme, osmotic shock or sonication and recovered extracellularly. After the refolding or from the disrupted cell solution, uniform Fab' can be purified using protein G column or the like (McCafferty J. et al., Antibody Engineering: A Practical Approach, IRL Press, 1996).

(4) Preparation of scFv scFv can be prepared by the genetic engineering method using phages or *Escherichia coli*. For example, the DNAs encoding VH and VL of the antibodies described in 2. (2), (5) and (6) are linked through a DNA encoding a polypeptide linker comprising an amino acid sequence of 12 residues or more to produce a DNA encoding scFv. It is important that the polypeptide linker is optimized such that its addition does not inhibit the binding of VH and VL to an antigen. For example, a linker indicated by Pantoliano et al. (Pantoliano M. W. et al., Biochemistry, 30, 10117-10125, 1991) or a variant thereof can be used.

An scFv expression vector can be prepared by cloning the produced DNA into a vector for expression of scFv. As the vector for expression of scFv, any of vectors capable of incorporating and expressing the DNA of scFv can be used. Examples thereof include pCANTAB5E (manufactured by Amersham Biosciences), Phfa (Lah M. et al., Hum. Antibodies Hybridomas, 5, 48-56, 1994) and the like. The scFv expression vector is introduced into appropriate *Escherichia coli*, and infected with a helper phage, whereby a phage can be obtained in which scFv is expressed on the surface of the phage by being fused with the phage surface protein. Further, scFv can be produced and accumulated in an inclusion body or a periplasmic space of *Escherichia coli* having introduced therein the scFv expression vector. From the inclusion body, active form of scFv can be formed by the refolding method which is commonly used in proteins. When it is expressed in the periplasmic space, cells can be disrupted by treatment such as partial digestion with lysozyme, osmotic shock or sonication and recovered extracellularly. After there folding or from the disrupted cell solution, uniform scFv can be purified using cation exchange chromatography or the like (McCafferty J. et al., Antibody Engineering: A Practical Approach, IRL Press, 1996).

(5) Preparation of Diabody

The diabody can be prepared such that the polypeptide linker in the preparation of scFv is produced of 3 to 10 residues. In case of using VH and VL of one type of the antibody, a divalent diabody can be produced. In case of using VHs and VLs of two types of the antibodies, a diabody having di-specificity can be produced (Le Gall F. et al., FEBS Lett., 453, 164-168, 1999, Courage C. et al., Int. J. Cancer, 77, 763-768, 1998).

(6) Preparation of dsFv dsFv can be prepared by the genetic engineering method using *Escherichia coli*. First, mutation is introduced into appropriate sites of the DNAs encoding VH and VL of the antibodies described in 2. (2), (5) and (6) to produce DNAs in which an amino acid residue encoded is replaced with cysteine. The modification of the amino acid residue with the cysteine residue can be performed by the method for mutagenesis using PCR as described in 2. (6). The respective DNAs produced are cloned into the vector for expression of dsFv to produce the expression vector of VH and VL. As the vector for expression of dsFv, any of vectors capable of inserting and expressing DNAs for dsFv can be used. Examples thereof include pUL19 (Reiter Y. et al., Protein Eng., 7, 697-704, 1994) and the like. The expression vector of VH and VL is introduced into appropriate *Escherichia coli*, and VH and VL can be formed and accumulated in an inclusion body or a periplasmic space. From the inclusion body or the periplasmic space, VH and VL are obtained, and mixed. Disulfide bonds are provided by the refolding method which is commonly used in proteins to form active dsFv. After the refolding, the fragment can further be purified by ion exchange chromatography, gel filtration or the like (Reiter Y. et al., Protein Eng., 7, 697-704, 1994).

(7) Preparation of a CDR-Containing Peptide

The CDR-containing peptide can be prepared by a chemical synthesis method such as the Fmoc method, the tBoc method or the like. A CDR-containing peptide expression vector can be prepared by producing a DNA encoding the CDR-containing peptide and cloning the resulting DNA into an appropriate vector for expression. As the vector for expression, any of vectors capable of inserting and expressing the DNA encoding the CDR-containing peptide can be used. Examples thereof include PLEX (manufactured by Invitrogen), pAX4a+ (manufactured by MoBiTec) and the like. The expression vector is introduced into appropriate *Escherichia coli*, and the CDR-containing peptide can be produced and accumulated in an inclusion body or a periplasmic space. From the inclusion body or the periplasmic space, the CDR-containing peptide can be obtained, and purified by ion exchange chromatography, gel filtration or the like (Reiter Y. et al., Protein Eng., 7, 697-704, 1994).

(8) Evaluation of Activity

The antigen-binding activity of the antibody fragment can be measured by the enzyme immunoassay using the antibody fragment as the first antibody as described in 1. (2), the surface plasmon resonance (Karlsson R. et al., J. Immunol. Methods, 145, 229-240, 1991) or the like. Further, whether the neutralizing activity by which to inhibit the FGF-8 activity is retained or not can be confirmed by the cell growth inhibition assay described in 1. (4).

4. Preventing or Treating Agent of the Present Invention

The anti-FGF-8 neutralizing antibody becomes a cartilage protecting agent because the antibody has such an ability that it is bound to FGF-8 in cells and tissues of a synovial membrane or a cartilage to inhibit the degradation of extracellular matrix of the cartilage induced by FGF-8 and the destruction of the cartilage. Since the antibody has an ability to inhibit the growth of synovial cells induced by FGF-8, it becomes an agent for inhibiting growth of synovial cells. Since the destruction of joints involves the destruction of the cartilage and the growth of synovial cells, the antibody becomes an agent for inhibiting joint destruction by inhibiting the growth of synovial cells and the destruction of the cartilage. Since the arthritis is a disease with the joint destruction, the antibody becomes an agent for treating and preventing arthritis by inhibiting the joint destruction. Examples of the arthritis include osteoarthritis, rheumatoid arthritis, systemic lupus erythematosus, ankylotic arthropathy, psoriatic arthritis, intervertebral disc disease, acute crystalline synovitis (gout, pseudogout) and the like.

Since the humanized antibody comprises a major part derived from the amino acid sequence of the human antibody in comparison to the monoclonal antibody of the non-human animal, it is expected that the high effect is shown within the human body, the immunogenicity is low and its effect is maintained over a long period of time. Thus, the humanized antibody is preferable as the preventing or treating agent.

The agent comprising the anti-FGF-8 neutralizing antibody may be administered as the treating agent alone. However, it is usually preferable to provide the agent as a pharmaceutical formulation produced by mixing the agent with one or more pharmaceutically acceptable carriers according to any method well known in the technical field of pharmaceutical.

As the administration route, it is advisable to use the most effective route in the treatment. Examples thereof can include oral administration and parenteral administrations such as intraoral, intratracheal, intrarectal, subcutaneous, intramuscular, intraarticular and intravenous administrations. In case of the antibody or peptide preparations, intraarticular and intravenous administrations are preferable.

Examples of the administration form include sprays, capsules, tablets, granules, syrups, emulsions, suppositories, injections, ointments, tapes and the like.

Examples of appropriate preparations for oral administration include emulsions, syrups, capsules, tablets, powders, granules and the like.

Liquid preparations such as emulsions and syrups can be produced by using, as additives, water, saccharides such as sucrose, sorbitol and fructose, glycols such as polyethylene glycol and propylene glycol, oils such as sesame oil, olive oil and soybean oil, antiseptics such as p-hydroxybenzoic acid esters, and flavors such as strawberry flavor and peppermint.

Capsules, tablets, powders, granules and the like can be produced by using, as additives, excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters, and plasticizers such as glycerin.

Examples of preparations appropriate for parenteral administration include injections, suppositories, sprays and the like.

Injections are prepared by using a carrier comprising a salt solution, a glucose solution or a mixture of both, and the like.

Suppositories are prepared using a carrier such as cacao butter, hydrogenated fat or carboxylic acid.

Sprays are prepared by using the antibody or the peptide as such or in combination with a carrier which facilitates dispersion and absorption of the antibody or the peptide in the form of fine particles without stimulating the mouth and the airway mucous membrane of a recipient.

Specific examples of the carrier include lactose, glycerin and the like. Preparations such as aerosol and dry powder can be formed depending on properties of the antibody or the peptide and the carrier used. These parenteral preparations may comprise the ingredients listed as additives in the oral preparations.

The dose or the number of administrations varies with the desired therapeutic effects, the administration method, the therapeutic period, the age, the body weight and the like. It is usually from 10 µg/kg to 20 mg/kg per day for an adult.

Whether the anti-FGF-8 neutralizing antibody inhibits the degradation of extracellular matrix of the cartilage and the growth of synovial cells can be confirmed using the in vitro assay system described in (1) and (2) below. Further, whether the anti-FGF-8 neutralizing antibody becomes the agent for treating or preventing arthritis can be evaluated by administering the antibody to arthritis morbid state model animals described in (3) below and examining whether it can reduce the arthritic syndromes thereof.

(1) Inhibitory Activity to Cartilage Destruction by FGF-8

The cartilage destruction can be evaluated by the assay indicating the degradation of extracellular matrix of the cartilage using chondrocytes or cartilaginous organs and the increase in production of destruction factors from chondrocytes and synovial cells, and the destruction of the subchondral bone according to the progression of the cartilage destruction can be evaluated by the assay indicating the bone resorption amount respectively.

(a) Degradation of Extracellular Matrix of the Cartilage

The function of the cartilage destruction can be evaluated by culturing rabbit articular chondrocytes subjected to primary culture in the presence of FGF-8 in case of adding the anti-FGF-8 neutralizing antibody and in case of not adding the same and measuring the amount of extracellular matrix remaining on the plate after the culturing. The amount of extracellular matrix is measured in terms of the amount of glycosaminoglycan liberated by the papain treatment. When the decrease in extracellular matrix induced by FGF-8 is inhibited by the addition of the anti-FGF-8 neutralizing antibody, the antibody is considered to have the inhibitory activity of cartilage destruction.

The function of the cartilage destruction can also be evaluated by culturing the cartilaginous organ of the bovine nasal septum subjected to primary culture according to the method of Price et al., (Price J. S. et al., Arthritis Rheum., 42, 137-147, 1999) in the presence of FGF-8 in case of adding the anti-FGF-8 neutralizing antibody and in case of not adding the same and measuring the amount of extracellular matrix in the cartilaginous organ after the culturing. When the decrease in extracellular matrix induced by FGF-8 is inhibited by the addition of the anti-FGF-8 neutralizing antibody, the antibody is considered to have the inhibitory activity of cartilage destruction. The amount of extracellular matrix is measured by treating the organ after the culturing with papain and measuring the amount of released glycosaminoglycan by the dimethylene blue method (Chandrasekhar S. et al., Anal. Biochem. 161 103-108, 1987) or measuring the amount of collagen in terms of a concentration of hydroxyproline according to Tokyo Eisei Nenpo, 36, 277, 1985.

(b) Production of Factors Involved in Cartilage Destruction

Examples of the factor involved in cartilage destruction can include prostaglandin $E_2$, matrix metalloproteinase-3 and nitric oxide. Rabbit joint chondrocytes or rabbit synovial cells are cultured in the presence of FGF-8 in case of adding the anti-FGF-8 neutralizing antibody and in case of not adding the same, and prostaglandin $E_2$, matrix metalloproteinase-3 or nitric oxide in the culture supernatant is measured as the amount of these factors produced from the cells. When the production of prostaglandin $E_2$, matrix metalloproteinase-3 or nitric oxide promoted by FGF-8 is inhibited by the addition of the anti-FGF-8 neutralizing antibody, the antibody is considered to have the inhibitory activity of cartilage destruction.

Prostaglandin $E_2$ can be measured by Prostaglandin $E_2$ EIA system (manufactured by Amersham Biosciences), matrix metalloproteinase-3 can be measured by Rabbit Matrix Metalloproteinase-3 ELISA system (manufactured by Amersham Biosciences) and nitric oxide can be measured by the method using Griess reagent (Green L. C. et al., Anal. Biochem. 126, 131-138 1982).

(c) Bone Resorption

The bone resorption can be evaluated by culturing the mouse calvariae in the presence of FGF-8 in case of adding the anti-FGF-8 neutralizing antibody and in case of not adding the same according to the method of Kusano et al. (Kusano K., et al., Endocrinology, 139, 1338-1345, 1998) and measuring the concentration of calcium or the concentration of hydroxyproline in the culture supernatant. When the bone resorption promoted with FGF-8 is inhibited by the addition of the anti-FGF-8 neutralizing antibody, the antibody is considered to have the inhibitory activity of cartilage destruction. The concentration of calcium in the culture supernatant can be measured by Calcium C-Test Wako (manufactured by Wako Pure Chemical Industries, Ltd.). The concentration of hydroxyproline in the culture supernatant can be measured according to Tokyo Eisei Nenpo, 36, 277, 1985.

(2) Synovial Cell Growth Inhibitory Activity

The growth of synovial cells can be evaluated by culturing synovial cells of human or rabbit in the presence of FGF-8 in case of adding the anti-FGF-8 neutralizing antibody and in case of not adding the same and measuring the amount of incorporation of [$^3$H]thymidine. When the amount of incorporation of [$^3$H]thymidine promoted by FGF-8 is inhibited by the addition of the anti-FGF-8 neutralizing antibody, the antibody is considered to have the synovial cell growth inhibitory activity.

(3) In Vivo Evaluation Using Arthritis Model in Animals

The effect of FGF-8 or the anti-FGF-8 neutralizing antibody on the joint destruction can be evaluated using the following arthritis model. The anti-FGF-8 neutralizing antibody is administered to the arthritis model. When the arthritis in the model animals is ameliorated the antibody is considered to be available as the agent for treating or preventing arthritis.

Examples of the model animals showing the symptoms similar to rheumatoid arthritis can include MRL-1pr/1pr mouse (Hang L. et al., J. Exp. Med., 155, 1690-1701, 1982, the mouse can be purchased from Japan Charles River) in which arthritis is spontaneously triggered mainly on the leg joint, rat adjuvant arthritis model (Pearson CM. et al., Arthritis Rheum., 5, 654-658, 1962, Taurog J. D. et al., Cell. Immunol., 75, 271-282, 1983, Bendele A. et al., J. Rheumatol., 26, 1225-1229, 1999) with arthritis induced by immunization with dead *tubercule bacillus*, mouse collagen-induced arthritis model (Stuart J. M. et al., Annu. Rev. Immunol., 2, 199-218, 1984, Kamada H. et al., Jpn. J. Pharmacol., 70, 169-175, 1996) with arthritis induced by immunization with type II collagen often found in joints along with an adjuvant, and the like. These model animals show the symptoms similar to rheumatoid arthritis, and are widely used in evaluation of the therapeutic drugs of arthritis.

When the rat adjuvant arthritis model is used, the volumes of the hind paw edema are measured with as time goes by on the adjuvant-treated foot (biphasic inflammation reaction including acute inflammation and subsequent chronic inflammation occurs) and the adjuvant-untreated foot (chronic inflammation occurs in approximately 1 week from sensitization). Both the hind paws are subjected to soft X-ray photography to evaluate the bone destruction and the deformation of joints. Further, the systemic cartilage destruction is evaluated by measuring the amount of glycosaminoglycan in urine, and the systemic bone destruction by in evaluated measuring the amount of deoxypyridinoline or the amount of hydroxyproline in urine respectively. The amount of glycosaminoglycan in urine can be measured by the dimethylmethylene blue method (Chandrasekhar S. et al., Anal. Biochem. 161 103-108, 1987), the amount of deoxypyridinoline in urine by using Osteolinks "DPD" (manufactured by Sumitomo Seiyaku K.K.), and the amount of hydroxyproline in urine by the method of Ikeda et al. (Ikeda Shingo et al., Tokyo Eiken Nenpo, 36 277-282, 1985) respectively. With respect to the index of the systemic responce of inflammation, the concentration of mucoprotein in serum is measured using Aspro-GP (manufactured by Otsuka Seiyaku), and the concentration of nitric oxide in serum by the method of Tracey et al. (Tracey W. R., et al., J. Pharmacol. Exp. Ther., 272, 1011-1015, 1995) respectively.

In case of using the mouse collagen-induced arthritis model, the change in body weight and the arthritic score of all limbs as time goes by and the anti-collagen antibody titer in serum are measured. Further, after dissection, the histopathological examination of the joint is performed. The arthritis is evaluated by scoring of 0 to 4 in one limb and 16 at the highest in all limbs. The scoring criteria are; 0: normal, 1: weak erythema is observed, 2: weak swelling and erythema are observed, 3: strong swelling and erythema are observed and warmth is felt by touch, and 4: clear swelling with deformation of fingers is observed.

As the osteoarthritis model, a model of a large animal such as a dog or a rabbit of which the joint is loosened by excising the meniscus of the knee or separating the ligament to cause chronic degeneration of the joint (hereinafter referred to as an experimental osteoarthritis model) has been often used (Ito Ryuta, Shinyaku Kaihatsu no tameno Dobutsu Moderu Riyo Shusei, Henkeisei Kansetsusho, R & D Planning, 1985, Guingamp C. et al., Arthritis Rheum., 40, 1670-1679, 1997, van der Kraan P. M. et al., Am. J. Pathol., 135, 1001-1014, 1989). Further, a monoiodoacetic acid-induced osteoarthritis rat model in which monoiodoacetic acid is injected into the knee joint of the rat to accelerate liberation of glycosaminoglycan as an extracellular matrix of the articular cartilage and induce the joint destruction is also listed as the osteoarthritis model.

The experimental osteoarthritis model obtained by partial excision of the rabbit knee joint meniscus can be produced by the method of Colombo et al. (Colombo C. et al., Arthritis Rheum., 26, 875-886, 1983) and the method of Kikuchi et al (Kikuchi Sumiyuki et al., Kansetsu Geka, 15, 92-98, 1966).

The monoiodoacetic acid-induced osteoarthritis rat model can be produced by injecting monoiodoacetic acid into the rat knee joint according to the method of Guingamp et al. (Guingamp C. et al., Arthritis Rheum., 40, 1670-1679, 1997).

In the osteoarthritis model animals, the knee joint patella is extracted after a certain period of time, and treated with papain, and the amount of glycosaminoglycan is measured by the dimethylmethylene blue method (Chandrasekhar S. et al., Anal. Biochem. 161, 103-108, 1987) to evaluate the joint destruction (degradation of extracellular matrix). Further, the histopathological examination of the knee joint is performed.

The dosage form and the administration route in administering the anti-FGF-8 neutralizing antibodies to the model animals can properly be selected depending on the qualities of the objective model animals and the severity. For example, these can be administered to the models animal orally or parenterally (intraperitoneal, intravenous, intraarticular, intramuscular or subcutaneous administration) either as such or in combination with other pharmatheutically acceptable additives such as carriers, excipients and diluents.

The mixing amount and the dose of the anti-FGF-8 neutralizing antibody are individually determined depending on the administration method, the dosage form and the use purpose of the preparations, the specific symptoms of the model animal, the body weight of the model animal and the like, and these are not particularly limited. The administration is possible with a dose of approximately 1 μg/kg to 100 mg/kg per day and once a day as an administration interval. The administration is also possible from two to four times a day, or more times a day. Further, the continuous administration through drip infusion or the like is also possible. When the antibody is administered to parts such as joints, it is administered to one position at a dose of from approximately 1 pg to 100 mg.

5. Diagnostic Agent of the Present Invention

FGF-8 induces the growth of synovial cells in joints and the destruction of extracellular matrix in cartilages. The foregoing anti-FGF-8 antibody can specifically bind to FGF-8 to detect and determine FGF-8. Thus, it can be used as a diagnostic agent of arthritis. Examples of the arthritis that can be diagnosed include the diseases described in 4. above. The detection and the determination of FGF-8 can be performed by the method described in 6. below.

As the anti-FGF-8 antibody used in the diagnostic agent of the present invention, any of antibodies which specifically bind to FGF-8 can be used. A monoclonal antibody and a polyclonal antibody are both available. A monoclonal antibody is preferably used.

Examples of the monoclonal antibody include an antibody produced by a hybridoma, a humanized antibody and an antibody fragment of these antibodies.

The anti-FGF-8 antibody used in the diagnostic agent of the present invention can be produced similarly by the method of producing the anti-FGF-8 neutralizing antibody. However, it is not required to inhibit activity of FGF-8. The anti-FGF-8 neutralizing antibody can also be used as the anti-FGF-8 antibody used in the diagnostic agent of the present invention. Specific examples of the anti-FGF-8 antibody used in the diagnostic agent of the present invention include monoclonal antibody KM1334 produced by hybridoma KM1334 (FERM BP-5451), human chimeric antibody KM3034 produced by transformant KM3034 (FERM BP-7836), human chimeric antibody KM3334 produced by transformant KM3334, human CDR-grafted antibody HV0LV6 produced by transformant KM8037 (FERM BP-8084), human CDR-grafted antibody HV0LV6/CHO produced by transformant KM8034, human CDR-grafted antibody HV0LV3-1/CHO produced by transformant KM8036 (FERM BP-8083) and human CDR-grafted HV0LV4-3/CHO produced by transformant KM8035 (FERM BP-8082).

The diagnostic agent comprising the anti-FGF-8 antibody may comprise a reagent for conducting an antigen-antibody reaction according to a diagnosing method indicated in 6. below and a detection reagent of the reaction. Examples of the reagent for performing the antigen-antibody reaction include buffer solutions, salts and the like. Examples of the detection reagent include reagents used in a usual immunological detection method, such as a labeled second antibody that recognizes the anti-FGF-8 antibody and a substrate corresponding to a label.

6. Method for Diagnosing Arthritis in the Present Invention

Examples of the arthritis which is diagnosed by the diagnosing method of the present invention include the diseases listed in 4. above. It is considered that in the joints of patients suffering from these diseases, the amount of FGF-8 having the activity of inducing the growth in synovial cells and the destruction of extracellular matrix in the cartilage is increased in comparison to healthy persons.

The method for diagnosing arthritis of the preset invention includes, for example, a method in which FGF-8 present in cells or tissues is immunologically detected and/or determined as described below using cells or tissue sections of the synovial membrane or the cartilage in the joint collected from subjects by the biopsy or the like and the cell extract or the synovial fluid produced from the cells or the tissues.

As the method for immunologically detecting and/or determining FGF-8 expressed in the joint using the anti-FGF-8 antibody, the fluorescent antibody method, the enzyme immunoassay (ELISA), the radio immunoassay (RIA), the immunotissue staining method, the immunocyte staining method, the Western blotting method, the immuno-precipitation method, the sandwich ELISA method (Tomiyama Sakuji & Ando Tamie, Tankuron Kotai Jikken Manual, Kodansha Scientific, 1987, Nihon Seikagaku Kai, Zoku Seikagaku Jikken Koza 5, Men-eki Seikagaku Kenkyuho, Tokyo Kagaku Dojin, 1986) and the like can be used.

The fluorescent antibody method can be performed by the method described in a document (Monoclonal Antibodies, Tomiyama Sakuji & Ando Tamie, Tankuron Kotai Jikken Manual, Kodansha Scientific, 1987) or the like. Specifically, a cell or a tissue of a joint isolated is reacted with the anti-FGF-8 antibody and further with an anti-immunoglobulin antibody labeled with a fluorescent substance such as fluorescein isothiocyanate (FITC) or phycoerythrin and the fluorescent dye is then measured with a flow cytometer.

The enzyme immunoassay (ELISA) is a method in which isolated cells, tissues, synovial fluids or the like from a joint are reacted with the anti-FGF-8 antibody and further reacted with an anti-immunoglobulin antibody labeled with an enzyme such as peroxidase or alkaline phosphatase, a substrate formed by an enzyme reaction is added for reaction, and the developed dye is measured by a spectrophotometer.

The radio immunoassay (RIA) is a method in which isolated cells, tissues, synovial fluids or the like from a joint are reacted with the anti-FGF-8 antibody and further reacted with an anti-immunoglobulin antibody labeled with an radioisotope, and the radioactivity is then measured with a scintillation counter or the like.

The immunocyte staining method and the immunotissue staining method are methods in which isolated cells, tissues, disrupted solutions thereof, synovial fluids or the like from a joint are reacted with the anti-FGF-8 antibody and further reacted with an anti-immunoglobulin antibody labeled with a fluorescent substance such as FITC, an enzyme such as peroxidase or alkaline phosphatase, or the like and a substrate developed by an enzyme reaction is added for reaction in case of labeling with an enzyme, after which observation with a microscope is performed. It can be performed by the method described in a document (Monoclonal Antibodies, Toyama Sakuji & Ando Tamie, Tan Kuron Kotai Jikken Manual, Kodansha Scientific, 1987).

The Western blotting is a method in which isolated cells, tissues, disrupted solutions thereof, synovial fluids or the like from a joint are dissolved in a sample buffer solution containing SDS to perform SDS-PAGE, the resulting sample is then transferred on a polyvinylidene fluoride (PVDF) film, and reacted with the anti-FGF-8 antibody and further reacted with an anti-immunoglobulin antibody labeled with an enzyme such as peroxidase or alkaline phosphatase, after which the reaction product is reacted with a substrate developed by an enzyme reaction or a substrate chemically illuminated and is detected as bands.

The immuno-precipitation method is a method in which disrupted cells, tissue solutions or a synovial fluid isolated from a joint are reactrd with the anti-FGF-8 antibody immobilized on beads or the like are reacted, the beads are isolated by centrifugation or the like and then treated with an SDS-comprising sample buffer, and dissolved FGF-8 is detected by the Western blotting or the like.

Sandwich ELISA is one of the enzyme immunoassays using two types of anti-FGF-8 antibodies different in epitope. It is a method in which one of the anti-FGF-8 antibodies is immobilized on a plate, and reacted with isolated cells, tissues, disrupted solutions thereof or synovial fluids from a joint, after which FGF-8 bound to the anti-FGF-8 antibody on the plate is further reacted with the other anti-FGF-8 antibody. The sample is reacted with an anti-immunoglobulin antibody labeled with an enzyme such as peroxidase or alkaline phosphatase and further with a substrate developed by an enzyme reaction, and the formed dye is measured with a spectrophotometer.

BEST MODE FOR CARRYING OUT THE INVENTION

Figure 1:
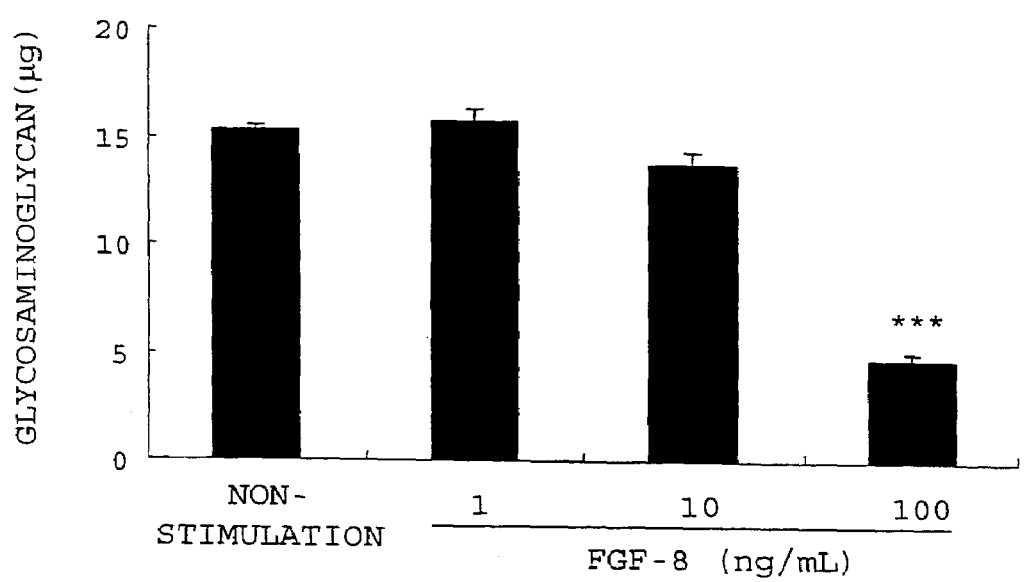
FIG. 1 is a graph showing a degradation activity of extracellular matrix of rabbit chondrocytes by FGF-8. The ordinate represents an amount of glycosaminoglycan remaining in extracellular matrix, and the abscissa represents the concentration (ng/mL) of FGF-8. The values represent the mean values±the standard error, and *** indicates P<0.001 (compared to a non-stimulated group, Dunnett test).

Examples and Reference Examples of the present invention are described below.

EXAMPLE 1

Degradation of Extracellular Matrix of Rabbit Chondrocytes with FGF-8 and Inhibition thereof by an Antibody Rabbit articular chondrocytes were isolated from both knees and shoulders of 3-week-old New Zealand white female rabbits and cultured according to the method of Tamura et al. (Tamura T. et al., Eur. J. Pharmacol., 419, 269-274, 2001). That is, the joints of both knees and the joints of both shoulders were isolated to collect the epiphyseal cartilages. These cartilages were washed with a phosphate-buffered saline solution, then sliced, and treated with 10 vol % FBS-comprising DMEM (FBS-comprising DMEM is hereinafter referred to as FBS/DMEM) comprising 0.4 w/v % actinase E at 37° C. for 1 hour and further with 10 vol % FBS/DMEM comprising 0.025 w/v % collagenase P at 37° C. for 5 to 6 hours to isolate and collect chondrocytes from the cartilaginous tissues. The collected chondrocytes were suspended in 10 vol % FBS/DMEM and adjusted to 100,000 cells/mL. The culture solution comprising the chondrocytes was inoculated in each well of a 24-well plate in an amount of 1 mL, and cultured in a gaseous phase of 5% $CO_2$-95% air at 37° C. After the chondrocytes became confluent, the culture medium was replaced with 0.5 vol % FBS/DMEM, followed by the culturing for 24 hours. The culture medium was removed, and 1 mL of 0.5 vol % FBS/DMEM (non-stimulated group) or 0.5 vol % FBS/DMEM comprising FGF-8 (1, 10 or 100 ng/mL; manufactured by Peprotech) was added, followed by the culturing for 48 hours. When the activity of the anti-FGF-8 neutralizing antibody was examined, 1 mL of 0.5 vol % FBS/DMEM comprising FGF-8 (100 ng/mL)(0 group) or 0.5 vol % FBS/DMEM comprising FGF-8 (100 ng/mL) and anti-FGF-8 neutralizing antibody KM1334 (1, 3 or 10 μg/mL) was added, and cultured for 48 hours. The culture solution was removed, and the amount of glycosaminoglycan in extracellular matrix remaining on the plate was measured by the dimethymethylene blue (DMMB) method (Chandrasekhar S. et al., Anal. Biochem. 161 103-108, 1987). That is, papain (manufactured by Sigma-Aldrich) was added to a storagebuffer of papain (0.1 mol/L sodium acetate, 50 mmol/L EDTA, pH 5.8) activated by adding 5 mmol/L-cysteine hydrochloride monohydrate to a final concentration of 20 μg/ml. Each well of the plate on which the chondrocytes had been cultured was added 1 mL of this solution, and digested overnight at 60° C. To 75 μL of this digested solution were added 25 μL of a guanidine hydrochloride buffer (2.88 mol/L guanidine hydrochloride, 50 mmol/L sodium acetate, pH 6.8) and 200 μL of a DMMB solution, and the absorbance was measured at 530/590 nm. The concentration of glycosaminoglycan of each sample was calculated from the absorbance of chondroitin sulfate (derived from whale cartilages, manufactured by Seikagaku Kogyo) used as a standard. Three experiments were performed for each condition and the mean values and the standard error were calculated.

Figure 2:
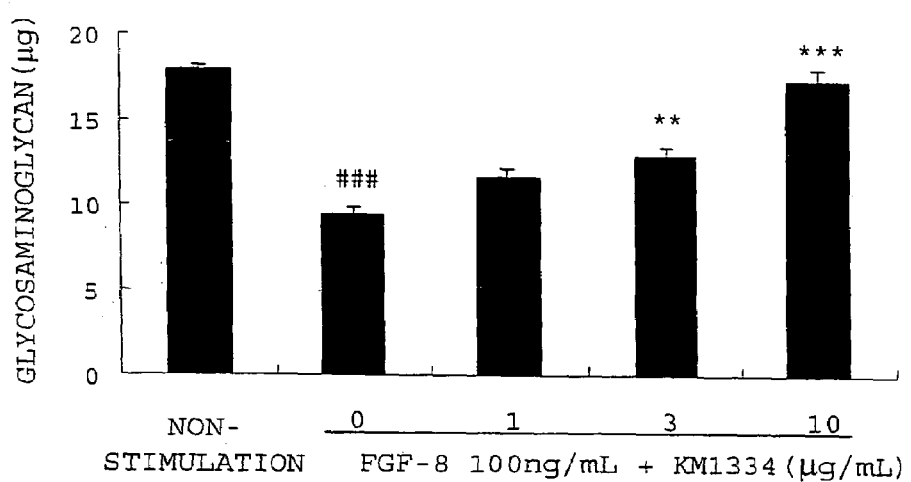
FIG. 2 is a graph showing inhibitory activity of anti-FGF-8 neutralizing antibody KM1334 to degradation of extracellular matrix of rabbit chondrocytes with FGF-8. The ordinate represents an amount of glycosaminoglycan remaining in extracellular matrix, and the abscissa represents the concentration (μg/mL) of KM1334. The values represent the mean values±the standarderror, and ### indicates P<0.001 (compared to a non-stimulated group, Student's t-test),  indicates P<0.01 and * indicatesP<0.001 (compared to a 0 group, Dunnett test).

The results are shown in FIGS. 1 and 2. FGF-8 significantly decreased the residual amount of glycosaminoglycan in extracellular matrix at the concentration of 100 ng/mL (FIG. 1).

This shows that FGF-8 has activity of promoting degradation of extracellular matrix of the cartilage. Further, anti-FGF-8 neutralizing antibody KM1334 significantly inhibited the promotion of degradation of extracellular matrix of the cartilage with FGF-8 at the antibody concentration of 3 μg/mL or more (FIG. 2). Accordingly, the degradation of extracellular matrix in arthritis can be suppressed by the administration of the anti-FGF-8 neutralizing antibody.

EXAMPLE 2

Promotion of Production of Matrix Metalloproteinase-3 from Rabbit Chondrocytes with FGF-8 and Inhibition thereof by an Antibody Rabbit articular chondrocytes were isolated and cultured by the method described in Example 1. After the chondrocytes became confluent, the culture solution was replaced with 0.5 vol % FBS/DMEM, followed by the culturing for 24 hours. The culture solution was removed, and 1 mL of 0.5 vol % FBS/DMEM (non-stimulated group), 0.5 vol % FBS/DMEM comprising FGF-8 (100 ng/mL)(0 group) or 0.5 vol % FBS/DMEM comprising FGF-8 (100 ng/mL) and anti-FGF-8 neutralizing antibody KM1334 (1, 3 or 10 μg/mL) was added, followed by the culturing for 48 hours. After 48 hours, the culture medium was recovered, the matrix metalloproteinase-3 concentration in the culture medium was measured using rabbit matrix metalloproteinase-3 ELISA system (manufactured by Amersham Biosciences). Three experiments were performed for each condition, and the mean values and the standard error were calculated.

Figure 3:
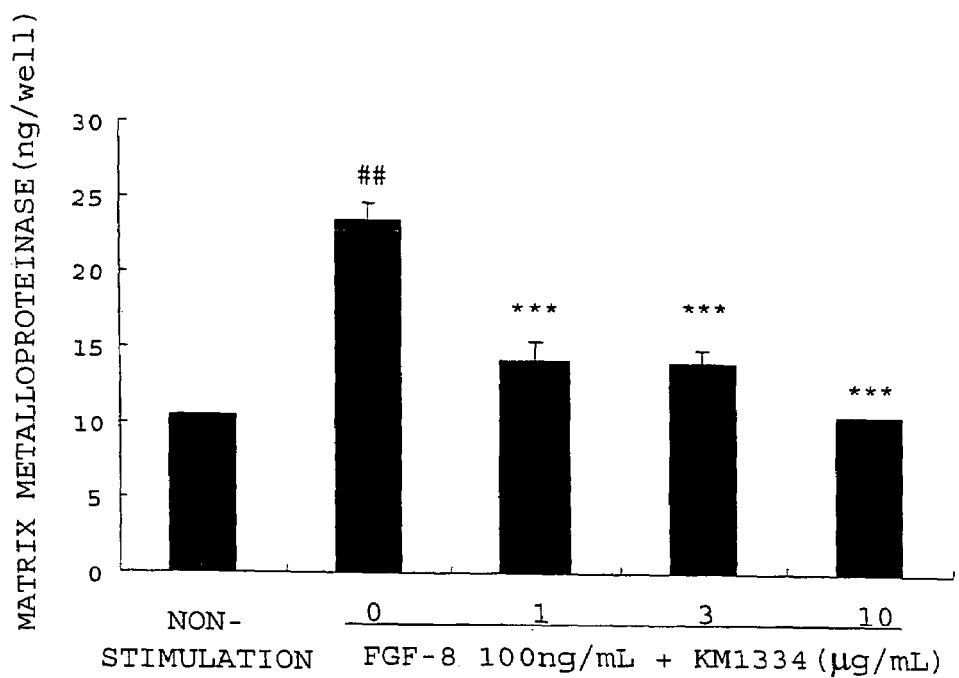
FIG. 3 is a graph showing promotion of production of matrix metalloproteinase-3 in rabbit chondrocytes with FGF-8 and inhibitory activity of anti-FGF-8 neutralizing antibody KM1334. The ordinate represents an amount (ng/well) of matrix metalloproteinase-3 in a culture solution, and the abscissa represents a concentration (μg/mL) of KM1334. The values represent the mean values±the standard error, and ## indicates P<0.01 (compared to a non-stimulated group, Aspin-Welch test) and *** indicates P<0.001 (compared to a 0 group, Dunnett test).

The results are shown in FIG. 3. FGF-8 significantly increased the production of matrix metalloproteinase-3 from the chondrocytes at a concentration of 100 ng/mL (non-stimulated group to 0 group, P=0.0079). This shows that FGF-8 has activity of promoting degradation of extracellular matrix through the productive induction of matrix metalloproteinase-3 from the chondrocytes. Further, anti-FGF-8 neutralizing antibody KM1334 significantly inhibited the production of matrix metalloproteinase-3 from the chondrocytes with FGF-8 at the antibody concentration of 1 μg/mL or more. The percent inhibition with 1, 3 or 10 μg/mL of anti-FGF-8 neutralizing antibody KM1334 was 72, 74 or 100% respectively. Accordingly, the administration of the anti-FGF-8 neutralizing antibody can inhibit the production of matrix metalloproteinase-3 from the chondrocytes and the degradation of extracellular matrix in arthritis.

EXAMPLE 3

Promotion of Growth of Rabbit Synovial Cells with FGF-8 and Inhibition thereof by an Antibody Rabbit synovial cells were collected by the method of Hamilton et al. (Hamilton J. A. and Slywka J., J. Immunol. 126, 851-855, 1981). The isolated synovial cells were suspended in RPMI 1640 medium comprising 10 vol % FBS (FBS-comprising RPMI 1640 medium is hereinafter referred to as FBS/RPMI 1640), and 10,000 cells was inoculated at each well of a 96-well culture plate. After 24 hours of the culturing, the culture medium of each well was removed, and 200 μL of 0.2 vol % FBS/RPMI 1640 (non-stimulated group) or 0.2 vol % FBS/RPMI 1640 comprising FGF-8 (1, 10 or 100 ng/mL) was added. When the activity of the anti-FGF-8 neutralizing antibody was examined, 200 μL of 0.2 vol % FBS/RPMI 1640 comprising FGF-8 (100 ng/mL) (0 group) or 0.2 vol % FBS/RPMI 1640 comprising FGF-8 (100 ng/mL) and anti-FGF-8 neutralizing antibody KM1334 (0.1, 0.3, 1, 3 or 10 μg/ml) was added to each well. After 48 hours of the culturing, 9.25 kBq per well of [$^3$H]thymidine was added. The culturing was further performed for 24 hours, and the radioactivity of [$^3$H]thymidine incorporated in the cells was measured using a liquid scintillation counter (1205 Beta Plate, manufactured by Perkin Elmer Life Science Japan). Six experiments were performed for each condition, and the mean values and the standard error were calculated.

Figure 4:
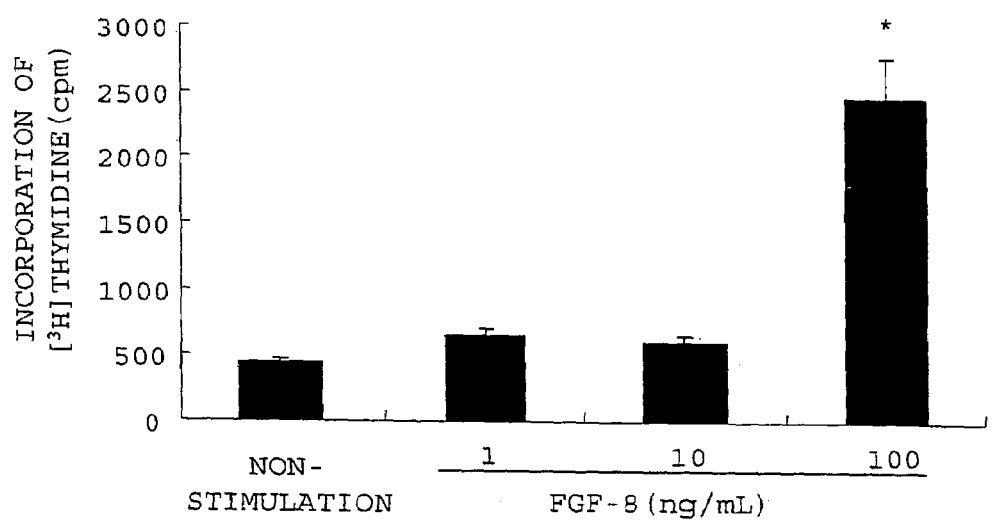
FIG. 4 is a graph showing activity of promoting growth of rabbit synovial cells with FGF-8. The ordinate represents radioactivity of [$^3$H]thymidine incorporated into rabbit synovial cells, and the abscissa represents a concentration (ng/mL) of FGF-8. The values represent the mean values±the standard error, and * indicates P<0.05 (compared to a non-stimulated group, Steel test).
Figure 5:
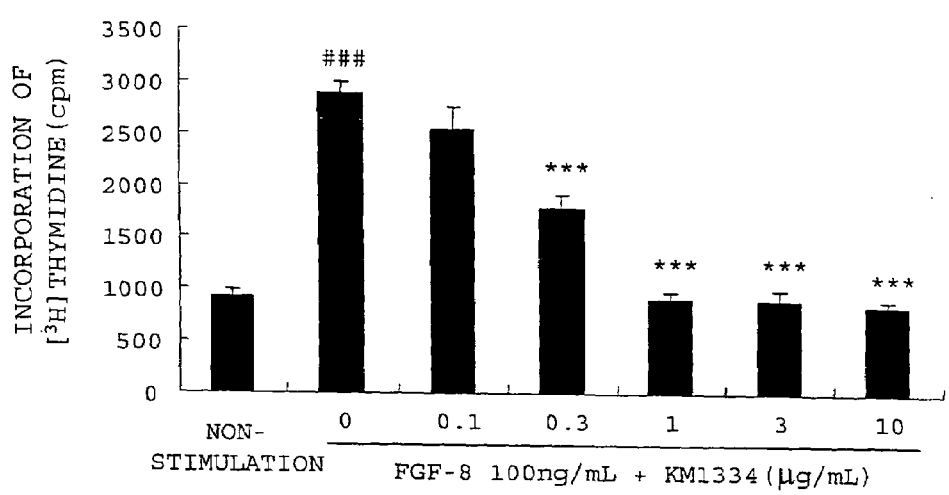
FIG. 5 is a graph showing inhibitory activity of anti-FGF-8 neutralizing antibody KM1334 to promotion of growth of rabbit synovial cells with FGF-8. The ordinate represents radioactivity of [$^3$H]thymidine incorporated into rabbit synovial cells, and the abscissa represents a concentration (μg/mL) of KM1334. The values represent the mean values±the standard error, and ### indicates P<0.001 (compared to a non-stimulated group, Student's t-test) and *** indicates P<0.001 (compared to a 0 group, Dunnett test).

The results are shown in FIGS. 4 and 5. FGF-8 significantly promoted the incorporation of [$^3$H]thymidine into the rabbit synovial cells at the concentration of 100 ng/mL (FIG. 4). This shows that FGF-8 has activity of promoting the growth of the rabbit synovial cells. Further, anti-FGF-8 neutralizing antibody KM1334 significantly inhibited the promotion of the FGF-8-dependent incorporation of [$^3$H]thymidine from the antibody concentration at 0.3 μg/mL (FIG. 5). Accordingly, the administration of the anti-FGF-8 neutralizing antibody can inhibit the growth of the synovial membrane in arthritis.

EXAMPLE 4

Promotion of Growth of Human Synovial Cells with FGF-8 and Inhibition thereof by an Antibody The same experiment as in Example 3 was performed using human synovial cells derived from the rheumatoid arthritis patient (procured from Toyobo). The concentration of FGF-8 was used at 10, 100 or 500 ng/mL, and the concentration of FGF-8 coexisting along with anti-FGF-8 neutralizing antibody KM1334 was used at 500 ng/mL. Six experiments were performed for each condition, and the mean values and the standard error were calculated.

Figure 6:
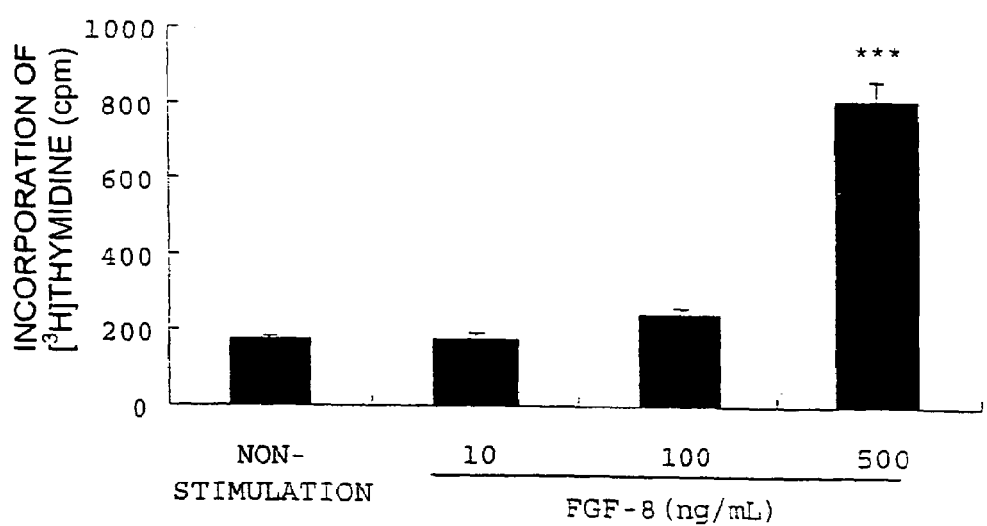
FIG. 6 is a graph showing activity of promoting growth of human synovial cells with FGF-8. The ordinate represents radioactivity of [$^3$H]thymidine incorporated into human synovial cells, and the abscissa represents a concentration (ng/mL) of FGF-8. The values represent the mean values±the standard error, and *** indicates P<0.001 (compared to a non-stimulated group, Dunnett test).
Figure 7:
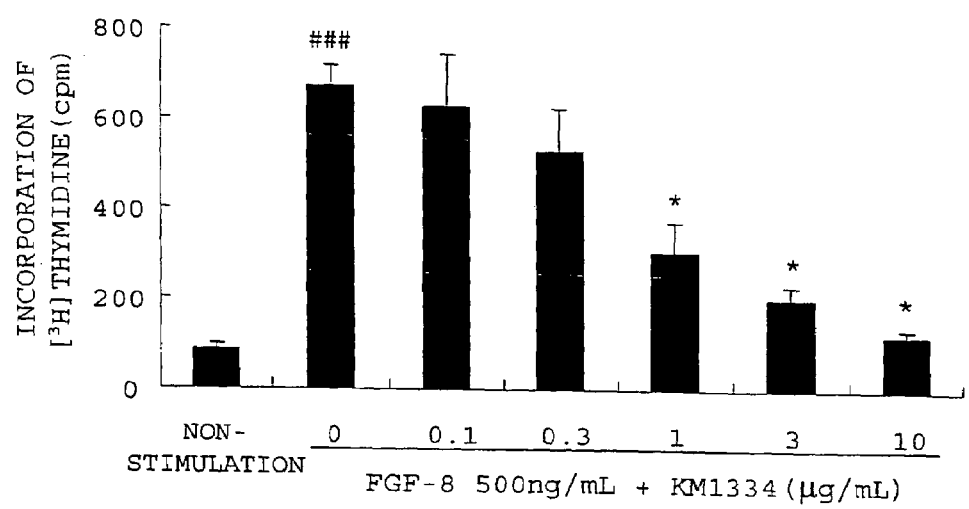
FIG. 7 is a graph showing inhibitory activity of the anti-FGF-8 neutralizing antibody KM1334 to promotion of growth of human synovial cells with FGF-8. The ordinate represents radio activity of [$^3$H]thymidine incorporated into human synovial cells, and the abscissa represents a concentration (μg/mL) of KM1334. The values represent the mean values±the standard error, and ### indicates P<0.001 (compared to a non-stimulated group, Aspin-Welch test) and * indicates P<0.05 (compared to a 0 group, Steel test).

The results are shown in FIGS. 6 and 7. FGF-8 significantly promoted the incorporation of [$^3$H]thymidine into the human synovial cells at the concentration of 500 ng/mL (FIG. 6). This shows that FGF-8 has activity of promoting the growth of the human synovial cells. Further, anti-FGF-8 neutralizing antibody KM1334 significantly inhibited the promotion of the FGF-8-dependent incorporation of [$^3$H]thymidine from the antibody concentration at 1 μg/mL (FIG. 7). Accordingly, the administration of the anti-FGF-8 neutralizing antibody can inhibit the growth of the synovial membrane in arthritis.

EXAMPLE 5

Staining of a Synovial Membrane Using an Anti-FGF-8 Antibody

Paraffin sections were prepared from a synovial membrane extracted from the human rheumatoid arthritis patient by the method of a document (Tanaka A. et al., Cancer Res. 58, 2053-2056, 1998), and the tissue immunostaining was performed using anti-FGF-8 antibody KM1334. As a result, the synovial cells of the three of four human rheumatoid arthritis synovial membranes were positive for FGF-8. Thus, FGF-8 was confirmed to be present in the human synovial membrane. Further, it was indicated that the human rheumatoid arthritis can be diagnosed by detecting the synovial cells of the human rheumatoid arthritis using the anti-FGF-8 antibody.

EXAMPLE 6

Induction of Arthritis by Intraarticular Injection of FGF-8

Arthritis-like phenotypes were induced in Sprague-Dawley rats (male, 7 weeks old, Japan Charles River) using FGF-8 in the following manner. Fifty μL of FGF-8 solution prepared with saline(manufactured by Otsuka Seiyaku Kojo) to a final concentration of 1 mg/mL was injected into the each knee joint of rats. Further, a group that injected 50 μL of saline into the knee joint was also prepared. One group consisted of 3 rats. After 3 days from the injection of FGF-8 or saline, the inside of the knee articular capsule was washed with 30 μL of saline comprising 0.38 w/v % sodium citrate to collect the lavage fluid, according to the method of Yamada et al (Yamada A. et al., Inflamm. Res., 49, 144-146, 2000). This procedure was repeated ten times to recover 300 μL of the joint lavage fluid. The amount of glycosaminoglycan in the joint lavage fluid was measured by the DMMB method described in Example 1. The patella of the knee joint was isolated, and the cartilaginous portion was digested with papain by the method described in Example 1 to measure the weight of the bone.

Figure 8:
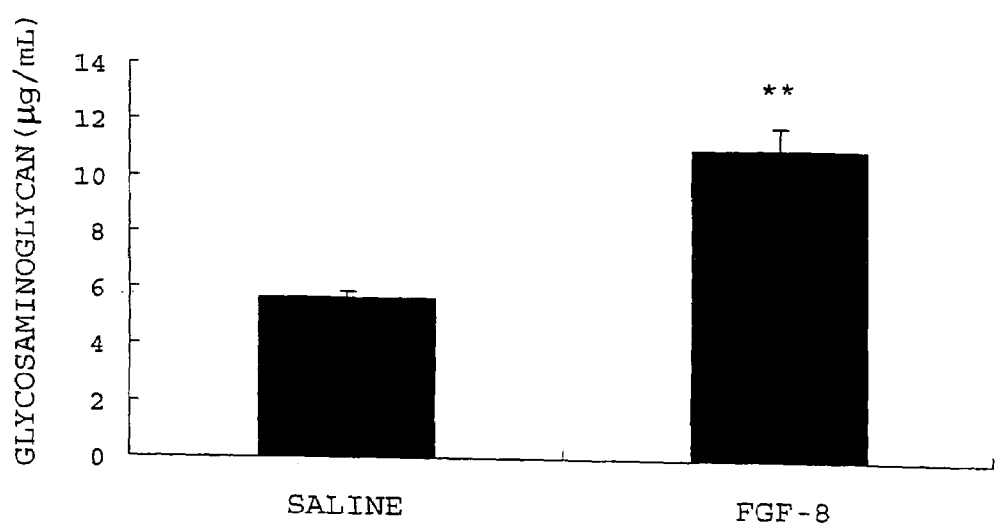
FIG. 8 is a graph showing degradation of extracellular matrix of the joint by injection of FGF-8. The ordinate represents a concentration (μg/mL) of glycosaminoglycan in a joint washing liquid. The values represent the mean values±the standard error, and ** indicates P<0.01 (compared to a saline injected group, Student's t-test).
Figure 9:
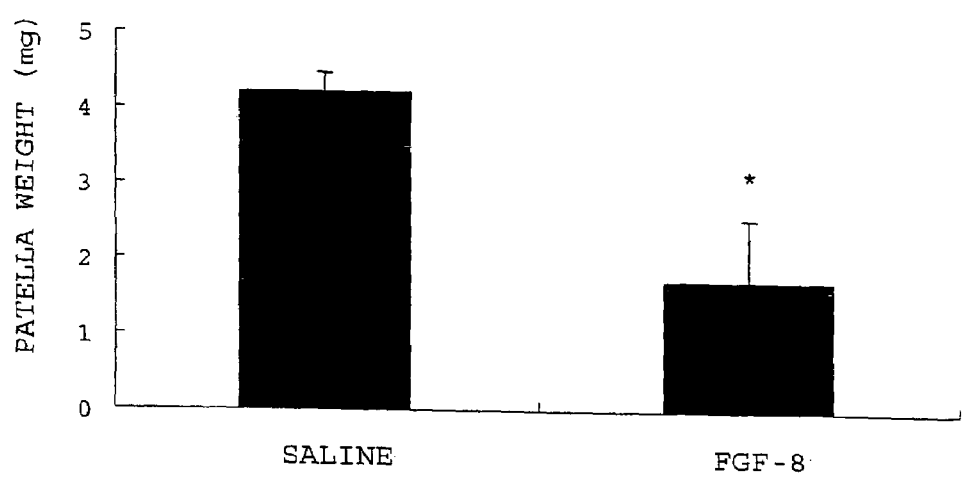
FIG. 9 is a graph showing destruction of the patella of the joint by the injection of FGF-8. The ordinate represents a weight (mg) of the patella. The values represent the mean values±the standard error, and * indicates P<0.05 (compared to a saline injected group, Student's t-test).

The results are shown in FIGS. 8 and 9. FIG. 8 shows the concentration of glycosaminoglycan in the joint lavage fluid. The injection of FGF-8 increased the concentration of glycosaminoglycan in the joint lavage fluid to 1.9 times of the saline injected group (P=0.0034). This indicates that the injection of FGF-8 progresses degradation of extracellular matrix of the articular cartilage. FIG. 9 shows the weight of the patella after the papain digestion. The injection of FGF-8 decreased the weight of the patella to 40% of the saline injected group (P=0.0454). This shows that the injection of FGF-8 promotes the destruction of the patella. Accordingly, it was shown that FGF-8 induces the destruction of the joint in vivo and causes the arthritis-like phenotypes.

EXAMPLE 7

Evaluation in a Mouse Collagen-induced Arthritis Model

The mouse collagen-induced arthritis model was prepared in the following manner according to the method of Kamada et al., (Kamada H. et al., Jpn. J. Pharmacol., 70, 169-175, 1996) using DBA/1J mice (male, 7 weeks old, Japan Charles River).

A bovine cartilage-derived type II collagen solution (manufactured by Collagen Gijutsu Kenshu) was mixed with a Freund's complete adjuvant (manufactured by Iatron) under ice cooling to form an emulsion which was adjusted such that the final concentration of the type II collagen became 1.5 mg/mL. The emulsion was intradermally injected in amount of 100 μL at the base of the tail of the mouse for sensitization. Twenty-one days later, the additional immunization was performed in the same manner. One group consisted of 10 mice. Anti-FGF-8 neutralizing antibody KM1334 was dissolved in a saline (manufactured by Otsuka Seiyaku Kojo) to a final concentration of 2 mg/mL, and the solution was intraperitoneally administered to a KM1334 administrated group at a dose of 200 μL for each mouse once a day on days 21, 25, 28, 32, 35 and 39 from the initial sensitization of the mouse collagen-induced arthritis model. Saline alone was intraperitoneally administered to a saline administrated group instead of the solution of anti-FGF-8 neutralizing antibody KM1334. Further, sodium diclofenac (manufactured by Sigma-Aldrich), a non-steroidal antiinflammatory drug, was dissolved in a 0.5 w/v % methyl cellulose solution to a final concentration of 0.3 mg/mL. The solution was orally administered to a sodium diclofenac administrated group as a positive control at a dose of 1 mL per 100 g of the body weight once a day on days 21 to 25, 28 to 32 and 35 to 39 from the initial sensitization of the mouse collagen-induced arthritis model. As a vehicle administrated group, only a 0.5 w/v % methyl cellulose solution was likewise orally administered. Further, an untreated group was set, and it was not subjected to collagen sensitization and administration of an agent. The change with time of edemas of all limbs in collagen-induced arthritis was evaluated by the scoring from 0 to 4 in each limb to a total of 16 at the maximum score in all limbs. The scoring criteria was as follows. 0: normal, 1: weak erythema is observed, 2: weak swelling and erythema are observed, 3: strong swelling and erythema are observed and warmth is felt by touch, and 4: clear swelling with deformation of fingers is observed.

Figure 10:
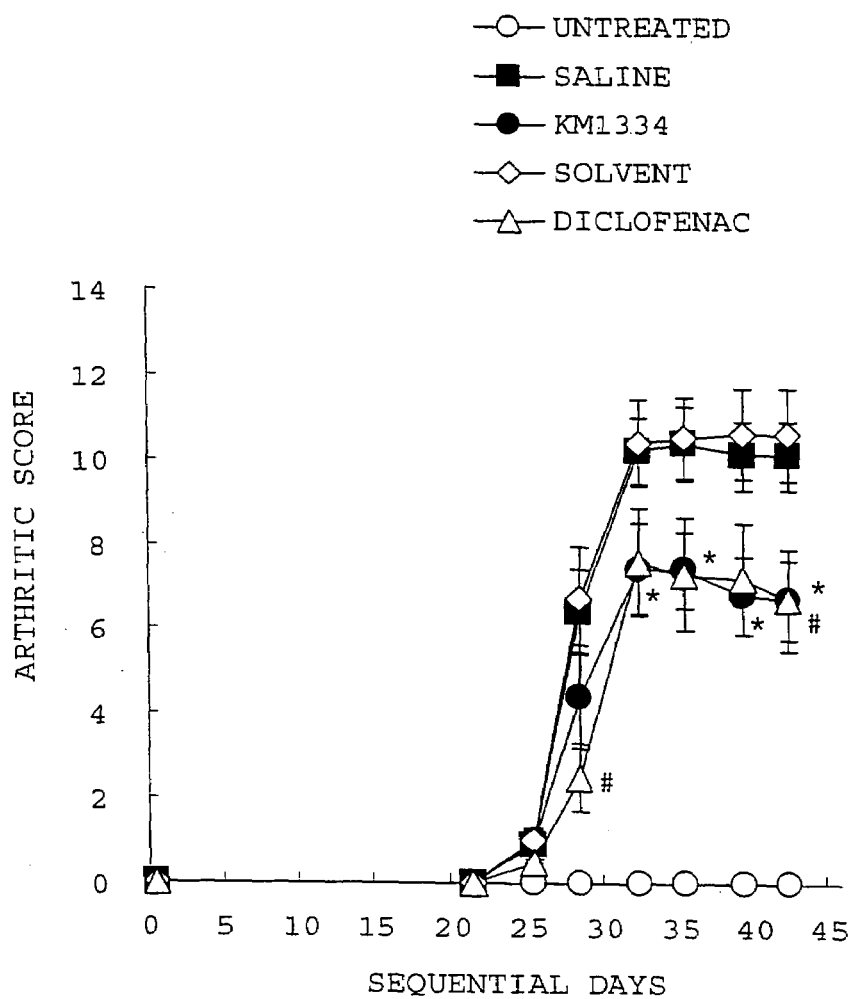
FIG. 10 is a graph showing inhibitory activity of anti-FGF-8 neutralizing antibody KM1334 to change with time of the arthritic score in mouse collagen induced arthritis. The ordinate represents the arthritic score, and the abscissa represents the sequential days from the first day of collagen sensitization. The values represent the mean values±the standard error, and * indicates P<0.05 (compared to a saline administrated group, Wilcoxon rank sum test) and # indicates P<0.05 (compared to a solvent administrated group, Wilcoxon rank sum test).

The results are shown in FIG. 10. In the anti-FGF-8 neutralizing antibody KM1334 administrated group, the significant inhibition of the 34% (P=0.0204) arthritic score was observed on day 42, and the degree of the inhibition was the same as the degree of the inhibition in the sodium diclofenac administrated group as the positive control (FIG. 10). This shows that the administration of the anti-FGF-8 neutralizing antibody can inhibit arthritis.

EXAMPLE 8

Evaluation in a Rat Adjuvant Arthritis Model

The rat adjuvant arthritis model was performed in the following manner according to the method of Pearson et al. (Pearson CM. et al., Arthritis Rheum., 5, 654-658, 1962) using Lewis rats (female, 8 weeks old, Japan Charles River).

*Mycobacterium butyricum* (manufactured by Difco) was suspended in a liquid paraffin (manufactured by Wako Pure Chemical Industries, Ltd.) to a final concentration of 6 mg/mL, and sterilized with a autoclave. The resulting solution was intradermally injected into the rat right hind pad in an amount of 100 μL for sensitization. One group consisted of 8 to 10 rats. Anti-FGF-8 neutralizing antibody KM1334 was dissolved in saline to a final concentration of 2 mg/mL. The solution was intraperitoneally administered to a KM1334 administrated group once a day at a dose of 0.5 mL per 100 g of the body weight for each rat on the sensitization day of the rat adjuvant arthritis model and on days 3, 7, 10, 14 and 17 from the sensitization. To saline administrated group, only saline was intraperitoneally administered instead of the anti-FGF-8 neutralizing antibody KM1334 solution. Further, sodium diclofenac, an antiinflammatory agent, was dissolved in a 0.5 w/v % methyl cellulose solution to a final concentration of 0.3 mg/mL, and the solution was orally administered to a sodium diclofenac administrated group as a positive control once a day at a dose of 1 mL per 100 g of the body weight on days 4, 7 to 11 and 14 to 18 from the adjuvant sensitization day. 50 mg of methotrexate® for injection (manufactured by Wyeth Japan) as a metabolic antagonist was dissolved in a 0.5 w/v % methyl cellulose solution to a final concentration of 0.01 mg/mL, and the solution was administered to a methotrexate administrated group in the same manner as in the sodium diclofenac administrated group. Prednisolone (manufactured by Sigma-Aldrich), a steroidal agent, was suspended in a 0.5 w/v % methyl cellulose solution to a final concentration of 0.3 mg/mL, and the suspension was administered to a prednisolone administrated group in the same manner as in the sodium diclofenac administrated group. Further, a 0.5 w/v % methyl cellulose solution alone was orally administered to a solvent administrated group in the same manner. An untreated group was used, and it was not subjected to sensitization with *Mycobacterium butyricum* and administration of an agent. The volumes of the adjuvant-treated paw and the adjuvant-untreated paw were measured as time goes by using a device for measuring edemas of rat hind paw (TK-101, manufactured by Unicom).

Figure 11:
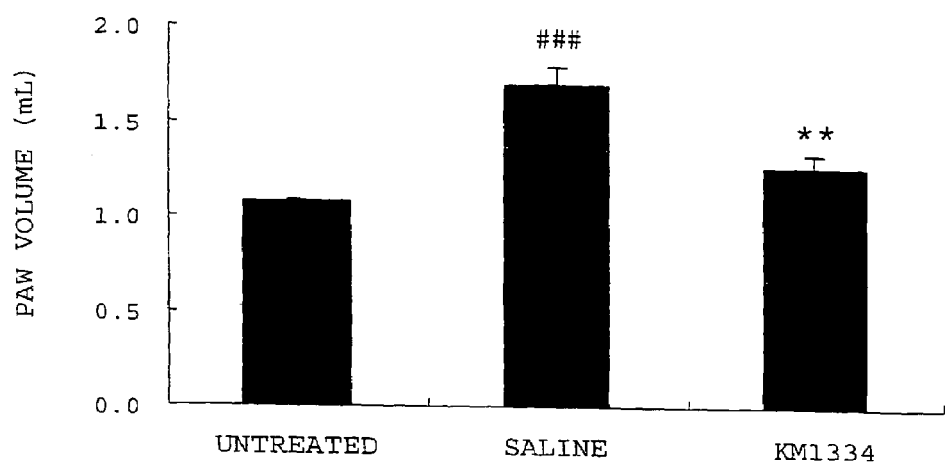
FIG. 11 is a graph showing inhibitory activity of anti-FGF-8 neutralizing antibody KM1334 to the increase in volume of a adjuvant-untreated foot pad in rat adjuvant arthritis. The ordinate represents the foot pad volume (mL). The values represent the mean values±the standard error, and ### indicates P<0.001 (compared to an untreated group, Aspin-Welch test) and ** indicates P<0.01 (compared to a saline administrated group, student's t-test).
Figure 12:
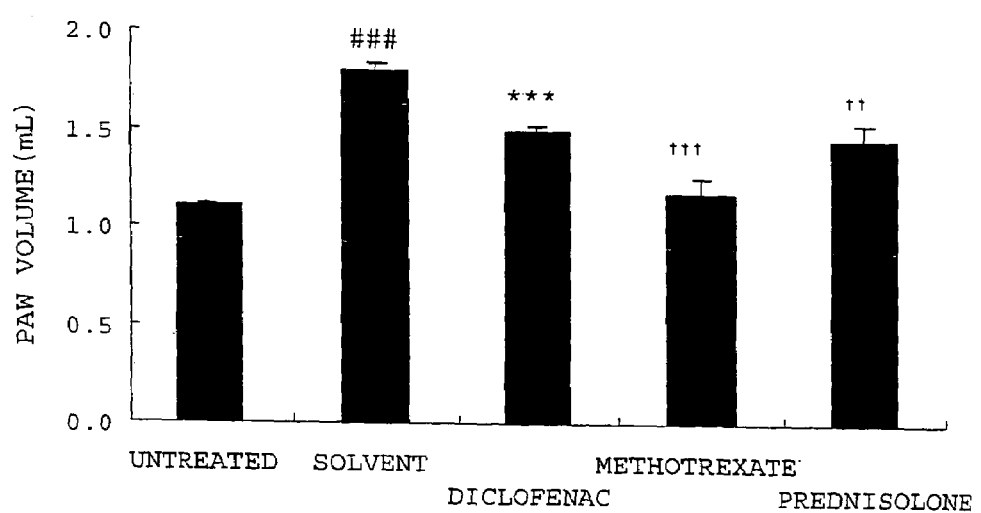
FIG. 12 is a graph showing inhibitory activity of sodium diclofenac, methotrexate and prednisolone to the increase in the volume of the adjuvant-untreated foot pad in rat adjuvant arthritis. The ordinate represents the foot pad volume (mL). The values represent the mean values±the standard error, and ### indicates P<0.001 (compared to an untreated group, Aspin-Welch test), *** indicates P<0.001 (compared to a solvent administrated group, Student's t-test), † †indicates P<0.01 and † † †indicates P<0.001 (compared to a solvent administrated group, Aspin-Welch test).

The results of measurement on day 21 from the sensitization day are shown in FIGS. 11 and 12. In the anti-FGF-8 neutralizing antibody KM1334 administrated group, the 69% (P=0.0010) significant inhibition of the increase in paw volume was observed in the adjuvant-untreated paw (FIG. 11). The 45% (P<0.0001) significant inhibition was observed in the sodium diclofenac administrated group, the 90% (P<0.0001) significant inhibition in the methotrexate administrated group and the 51% (P=0.0029) significant inhibition in the prednisolone administrated group, respectively (FIG. 12). That is, anti-FGF-8 neutralizing antibody KM1334 exhibited the inhibitory activity of edema superior to those of sodium diclofenac and prednisolone.

Using urine collected for 24 hours at day 20 and day 21 after the sensitization, the amounts of glycosaminoglycan, deoxypyridinoline, hydroxyproline and creatinine in urine were measured. The amount of glycosaminoglycan in urine was measured by the DMMB method described in Example 1. The amount of hydroxyproline in urine was measured by the method of Ikeda et al. (Ikeda Shingo et al., Tokyo Eiken Nenpo, 36 277-282, 1985). That is, 0.8 mL of hydrochloric acid for amino acid analysis (manufactured by Kanto Kagaku) was added to 0.8 mL of urine to hydrolyze at 110° C. for 15 hours. To 0.5 mL of the hydrolyzed sample was added 2 mL of a 1.2 mol/L sodium hydroxide solution for neutralization. 1 mL of isopropanol was added to 0.5 mL of the neutralized sample, and 1 ml of an oxidant solution was added. The mixture was stirred well, and allowed to stand at room temperature for 5 minutes. The oxidant solution is prepared by dissolving 5.7 g of sodium acetate trihydrate, 3.75 g of trisodium citrate dihydrate and 0.602 g of citric acid monohydrate into about 50 mL of distilled water, adding 38.5 mL of isopropanol, further adding distilled water to adjust the volume to 100 mL and fully mixing the resulting acetate-citric acid buffer solution with a 7 w/v % chloramine T solution (sodium p-toluenesulfone chloroamide trihydrate, manufactured by Wako Pure Chemical Industries Ltd.) prepared by using distilled water at a ratio of 4:1 in use. Thereafter, 1 mL of an Ehrlich reagent was added, and the mixture was stirred well, and heated at 60° C. for 20 minutes in an incubator. The Ehrlich reagent is a reagent obtained by dissolving 17.6 g of p-dimethylaminobenzaldehyde (manufactured by Wako Pure Chemical Industries, Ltd.) in 20.9 mL of perchloric acid (manufactured by Kanto Kagaku) and adding isopropanol to adjust the volume to 100 mL. After the heating, the product was cooled with running water, and the absorbance was measured at 562 nm. The concentration of hydroxyproline in each sample was calculated using a calibration curve made from an absorbance of L-hydroxyproline (manufactured by Wako Pure Chemical Industries, Ltd.). The amount of deoxypyridinoline in urine was measured using Osteolinks "DPD" (manufactured by Sumitomo Seiyaku). The amount of creatinine in urine was measured using Creatinine-Test Wako (manufactured by Wako Pure Chemical Industries, Ltd.). For correcting the difference in urine concentration between individuals, a glycosaminoglycan concentration/creatinine concentration ratio, a deoxypyridinoline concentration/creatinine concentration ratio or a hydroxyproline concentration/creatinine concentration ratio was calculated for each individual, and used as each index.

Figure 13:
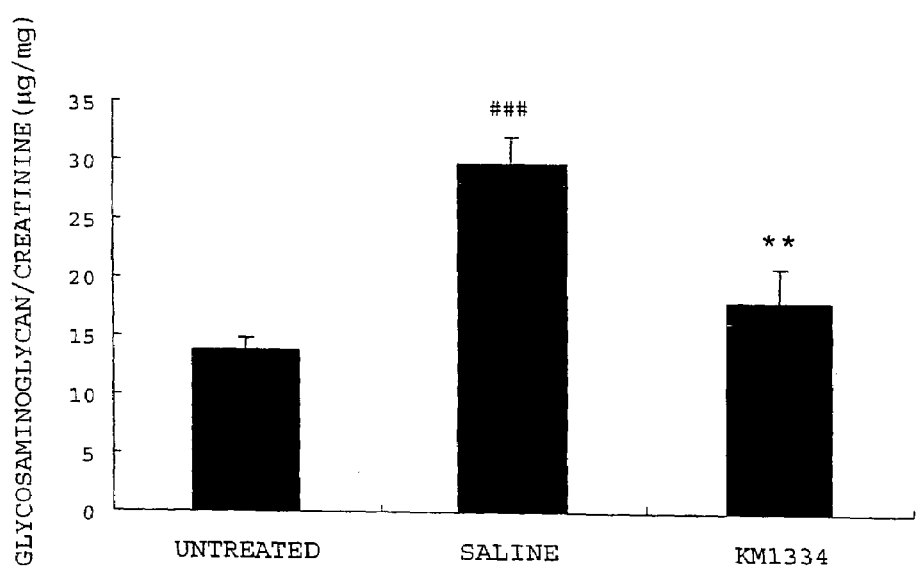
FIG. 13 is a graph showing inhibitory activity of anti-FGF-8 neutralizing antibody KM1334 to the increase in amount of glycosaminoglycan in urine of rat adjuvant arthritis. The ordinate represents a ratio of glycosaminoglycan concentration/creatinine concentration (μg/mg). The values represent the mean values±the standard error, and ### indicates P<0.001 (compared to an untreated group, Aspin-Welch test) and ** indicates P<0.01 (compared to a saline administrated group, Student's t-test).
Figure 14:
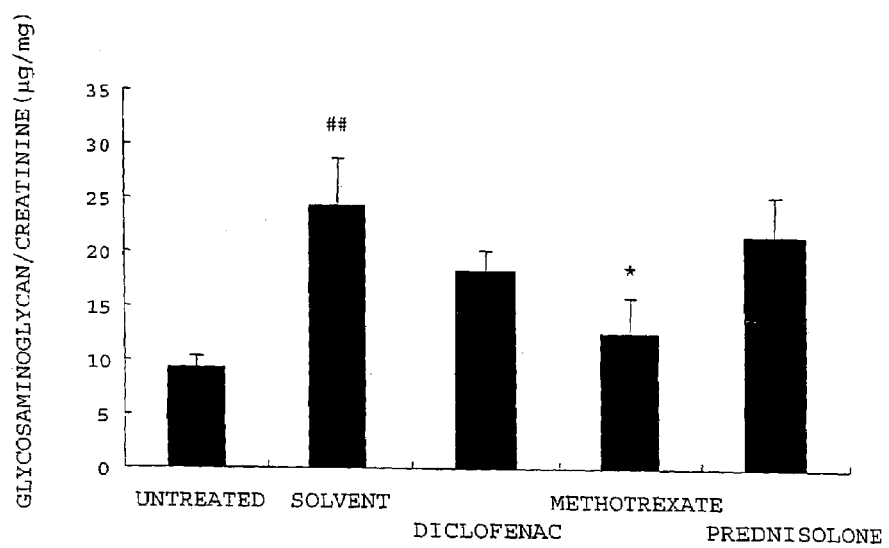
FIG. 14 is a graph showing inhibitory activity of sodium diclofenac, methotrexate and prednisolone to the increase in amount of glycosaminoglycan in urine of rat adjuvant arthritis. The ordinate represents a glycosaminoglycan concentration/creatinine concentration ratio (μg/mg). The values represent the mean values±the standard error, and ## indicates P<0.01 (compared to an untreated group, Aspin-Welch test) and * indicates P<0.05 (compared to a solvent administrated group, Student's t-test).

The results are shown in FIGS. 13 to 17. The amount of glycosaminoglycan in urine was increased in the saline administrated group to 2.2 times of the untreated group (P<0.0001) (FIG. 13). This shows that the cartilage destruction progresses according to the arthritis proceeds. In the anti-FGF-8 neutralizing antibody KM1334 administrated group, the 73% (P=0.0064) significant inhibition was observed to the increase in amount of glycosaminoglycan in urine (FIG. 13). In the methotrexate administrated group, the 79% (P=0.0465) significant inhibition of the increase in amount of glycosaminoglycan in urine was observed. The 40% decrease in amount of glycosaminoglycan in urine was observed in the sodium diclofenac administrated group, and the 18% decrease in amount of glycosaminoglycan in urine was observed in the prednisolone administrated group, though not significant (FIG. 14). That is, anti-FGF-8 neutralizing antibody KM1334 exhibited the same cartilage destruction inhibitory activity as methotrexate.

Figure 15:
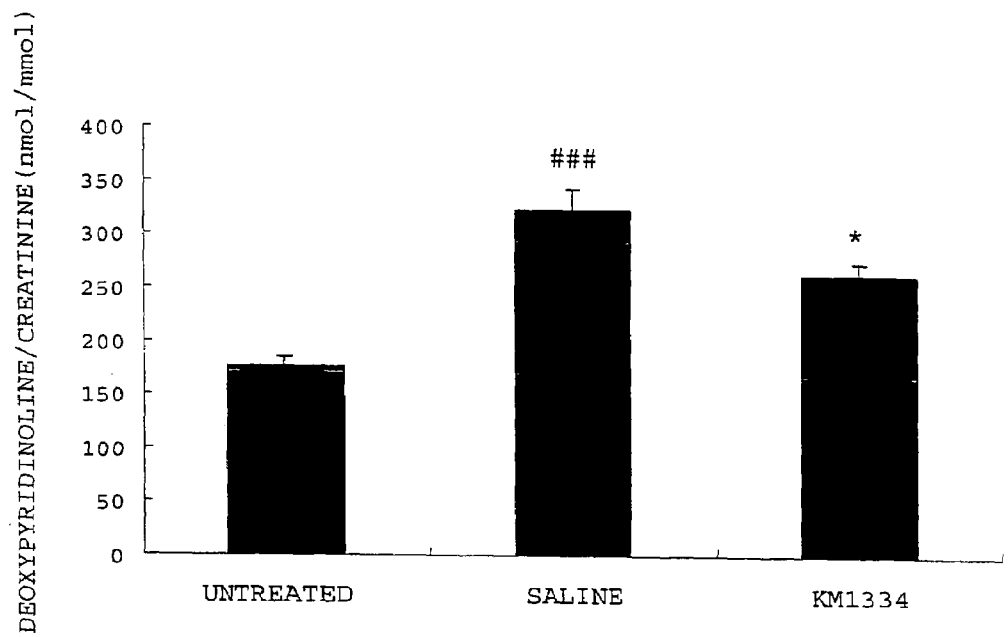
FIG. 15 is a graph showing inhibitory activity of anti-FGF-8 neutralizing antibody KM1334 to the increase in amount of deoxypyridinoline in urine of rat adjuvant arthritis. The ordinate represents a deoxypyridinoline concentration/creatinine concentration ratio (nmol/mmol). The values represent the mean values±the standard error, and ### indicates P<0.001 (compared to an untreated group, Aspin-Welch test) and * indicates P<0.05 (compared to a saline administrated group, Student's t-test).
Figure 16:
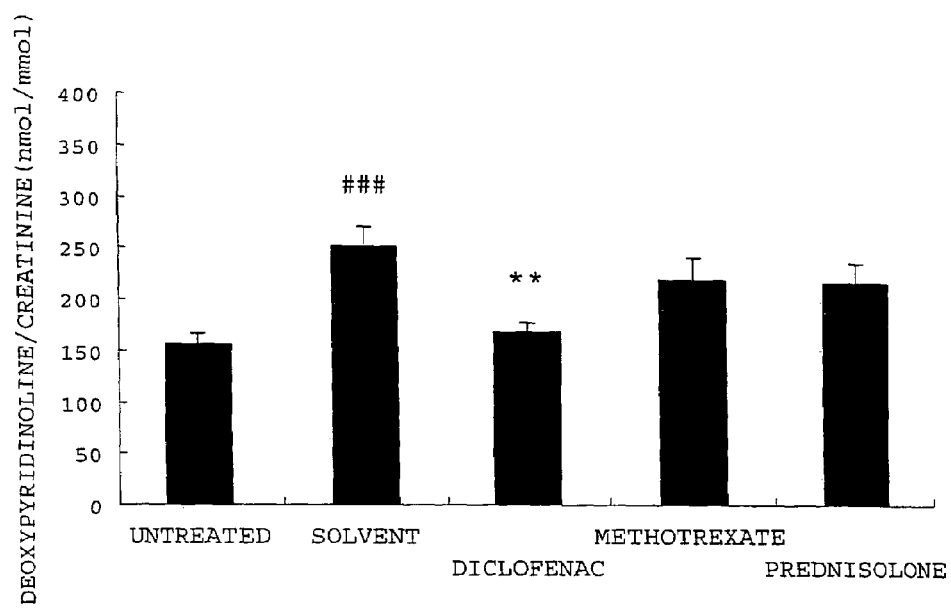
FIG. 16 is a graph showing inhibitory activity of sodium diclofenac, methotrexate and prednisolone to the increase in the amount of deoxypyridinoline in urine of rat adjuvant arthritis. The ordinate represents a deoxypyridinoline concentration/creatinine concentration ratio (nmol/mmol). The values represent the mean values±the standard error, and ### indicates P<0.001 (compared to an untreated group, Student's t-test) and ** indicates P<0.01 (compared to a solvent administrated group, Student's t-test).

The amount of deoxypyridinoline in urine was increased to 1.8 times of the untreated group (P<0.0001) in the saline administrated group (FIG. 15). This shows that the bone destruction progresses as the arthritis proceeds. In the anti-FGF-8 neutralizing antibody KM1334 administrated group, the 41% (P=0.0185) significant inhibition was observed to the increase in amount of deoxypyridinoline in urine. In the sodium diclofenac administrated group, the 88% (P=0.0016) significant inhibition was observed to the increase in amount of deoxypyridinoline in urine. The 34% decrease in amount of deoxypyridinoline in urine was observed in the methotrexate administrated group, and the 38% decrease in amount of deoxypyridinoline in urine was observed in the prednisolone administrated group, though not significant (FIG. 16). That is, anti-FGF-8 neutralizing antibody KM1334 exhibited the inhibitory activity of the bone destruction over methotrexate and prednisolone.

Figure 17:
FIG. 17 is a graph showing inhibitory activity of anti-FGF-8 neutralizing antibody KM1334 to the increase in amount of hydroxyproline in urine of rat adjuvant arthritis. The ordinate represents a hydroxyproline concentration/creatinine concentration ratio (μg/mg). The values represent the mean values±the standard error, and ### indicates P<0.001 (compared to an untreated group, Student's t-test).

The amount of hydroxyproline in urine was increased to 1.8 times of the untreated group (P=0.0002) in the saline administrated group (FIG. 17). This shows that the bone destruction progresses as the arthritis proceeds. In the anti-FGF-8 neutralizing antibody KM1334 administrated group, the 48% decrease was observed to the increase in amount of hydroxyproline in urine, though not significant.

On day 21 from sensitization, the adjuvant-untreated paw was sampled by being cut in the tibial shaft, and fixed with a 10 vol % phosphate-buffered formalin solution. Subsequently, it was photographed with soft X-rays under conditions of 29 kV, 4 mA and 2 minutes using a soft X-ray generator SOFRON SR0-M50 (manufactured by Sofron). The photograph was observed using a stereoscopic microscope and the bone destruction was scored. The scoring was performed by observing the presence or the absence of the bone erosion of the calcaneus (a total of five sites with one side defined as one site). When the erosion was observed, it was defined as 1; when the erosion was not observed, it was defined as 0; and the maximum score was 5 in one paw.

The results are shown in Tables 1 and 2. The values mean the represent values±the standard error, and * indicates $P<0.05$,  indicates $P<0.01$ and * indicates $P<0.001$ (compared to a solvent administrated group, Wilcoxon rank sum test).

TABLE 1

| Administrated group | Bone destruction score | (% inhibition) |
|---|---|---|
| Untreated | 0.0 ± 0.0 | — |
| Saline | 4.4 ± 0.3 | — |
| KM1334 | 3.2 ± 0.5 | 27% |

TABLE 2

| Administrated group | Bone destruction score | (% inhibition) |
|---|---|---|
| Untreated | 0.0 ± 0.0 | — |
| Solvent | 4.6 ± 0.3 | — |
| Diclofenac | 3.1 ± 0.6* | 33% |
| Methotrexate | 0.9 ± 0.4*** | 80% |
| Prednisone | 1.8 ± 0.7** | 61% |

The 27% decrease in bone destruction score was observed in the anti-FGF-8 neutralizing antibody KM1334 administrated group, though not significant (Table 1). With respect to the bone destruction score, the 33% (P=0.0362) decrease was observed in the sodium diclofenac administrated group, the 80% (P=0.0006) decrease in the methotrexate administrated group, and the 61% (P=0.0032) decrease in the prednisolone administrated group (Table 2). That is, anti-FGF-8 neutralizing antibody KM1334 showed the same decrease in bone destruction score as that of sodium diclofenac.

The paraffin sections of the adjuvant-untreated paw fixed with formalin were prepared. The sections were subjected to hematoxylin/eosin staining, and the bone, the joint and the region around the joint from the tibia to the metatarsal bone were histopathologically evaluated. The plasma leakage to the tissue around the joint or to the articular cavity was evaluated by the scoring from 0 to 4 in one paw. The scoring criteria were as follows. 0: no change, 1: very slight change is observed, 2: slight change is observed, 3: medium change is observed, and 4: heavy change is observed.

The results are shown in Table 3. The values represent the mean values±the standard error, and * indicates P<0.05, and ** P<0.01 (compared to saline administrated group, Wilcoxon rank sum test).

TABLE 3

| | Pathological score | | | |
|---|---|---|---|---|
| Administrated group | Blood leak around joint | (Percent inhibition) | Blood cell plasma leak to articular cavity | (Percent inhibition) |
| Untreated | 0.0 ± 0.0 | — | 0.0 ± 0.0 | — |
| Saline | 3.4 ± 0.2 | — | 2.7 ± 0.2 | — |
| KM1334 | 2.0 ± 0.4** | 41% | 1.6 ± 0.3* | 41% |

In the anti-FGF-8 neutralizing antibody KM1334 administrated group, the 41% decrease (P=0.0022) of the plasma leak to the tissue around the joint and the 41% decrease (P=0.0156) of the blood cell and plasma leak to the articular cavity were observed (Table 3). Accordingly, the administration of the anti-FGF-8 neutralizing antibody can inhibit edema formation in arthritis and the destruction of cartilages and bones.

EXAMPLE 9

Evaluation in a Rat Monoiodoacetic Acid-induced Osteoarthritis Model

The rat monoiodoacetic acid-induced osteoarthritis model was produced in the following manner by the method of Guingamp et al. (Guingamp C. et al., Arthritis Rheum., 40, 1670-1679, 1997) using Sprague-Dawley rats (male, 7 weeks old, Japan Charles River).

Monoiodoacetic acid (manufactured by Sigma-Aldrich) prepared with saline to a final concentration of 10 mg/mL was injected into the right knee joint of the rat in an amount of 25 µL. One group consisted of 10 rats. Anti-FGF-8 neutralizing antibody KM1334 was dissolved in saline (manufactured by Otsuka Seiyaku Kojo) to a final concentration of 4 mg/mL, and the antibody solution at a dose of 0.5 mL per 100 g of the body weight was intraperitoneally administered to a KM1334 administrated group once at the injection of monoiodoacetic acid. To saline group, the saline alone was intraperitoneally administered instead of the antibody solution. Further, a sham operated group was arranged, and the saline was injected in the knee joint thereof without the administration of the agent. After 3 days from the injection of monoiodoacetic acid, the joint washing liquid was recovered by the method described in Example 6. The amount of glycosaminoglycan in the joint lavage fluid was measured by the DMMB method described in Example 1.

The results are shown in FIG. 17. The injection of monoiodoacetic acid increased the concentration of glycosaminoglycan in the joint washing liquid to 1.6 times of the sham operated group (P=0.0014). This shows that the degradation of extracellular matrix of the articular cartilage progresses by the injection of monoiodoacetic acid. In the anti-FGF-8 neutralizing antibody KM1334 administrated group, the 42% (P=0.0188) significant inhibition was observed to the increase in concentration of glycosaminoglycan in the joint lavage fluid at the injection of monoiodoacetic acid. Accordingly, the administration of the anti-FGF-8 neutralizing antibody can inhibit the destruction of the articular cartilage in arthritis.

REFERENCE EXAMPLE 1

Production of an Anti-FGF-8 Neutralizing Chimeric Antibody

1. Isolation and Analysis of cDNAs Encoding V Regions of a Mouse Anti-FGF-8 Neutralizing Antibody (1) Preparation of mRNAs from Mouse Anti-FGF-8 Neutralizing Antibody-Producing Hybridoma Cells Approximately 8 μg of mRNAs was prepared from $1 \times 10^7$ cells of hybridoma KM1334 (FERM BP-5451, Japanese published unexamined application No. 271391/97) which produces a mouse anti-FGF-8 neutralizing antibody using Fast-Track Isolation mRNA Kit (manufactured by Invitrogen), a preparation kit of mRNA according to the attached manual.

(2) Prepration of H Chain and L Chain cDNA Libraries of an Anti-FGF-8 Neutralizing Mouse Antibody cDNAs having EcoRI-NotI adapters at both ends were synthesized from 5 μg of mRNAs of KM1334 obtained in (1) above using TimeSaver cDNA Synthesis Kit (manufactured by Amersham Biosciences) according to the attached manual. Subsequently, cDNA libraries were produced using λZAPII Cloning Kit (manufactured by Stratagene). First, the total amount of cDNAs was dissolved in 20 μL of sterile water, and the solution was fractionated by agarose gel electrophoresis to recover approximately 0.1 μg of a cDNA fragment of approximately 1.5 kb corresponding to H chain of an IgG class antibody and a cDNA fragment of approximately 1.0 kb corresponding to L chain of κ class. Then, 0.1 μg of the cDNA fragment of approximately 1.5 kb and 0.1 μg of the cDNA fragment of approximately 1.0 kb were ligated with 1 μg of λZAPII vector whose end was dephosphorylated with calf intestine alkaline phosphatase after digestion with restriction endonuclease EcoRI according to the attached manual.

4 μl of each of the reaction solutions after the ligation was packaged in λ phages using Gigapack II Packaging Extracts Gold (manufactured by Stratagene) according to the attached manual and *Escherichia coli* XL1-Blue strain (manufactured by Stratagene) was infected with an appropriate amount thereof to obtain approximately $8.1 \times 10^4$ phage clones and approximately $5.5 \times 10^4$ phage clones as an H chain cDNA library and an L chain cDNA library of KM1334. Subsequently, these phages were immobilized on nylon membranes respectively by a usual method (Molecular Cloning 3rd edition).

(3) Cloning of H Chain and L Chain cDNAs of an Anti-FGF-8 Neutralizing Mouse Antibody The nylon membranes of the H chain cDNA library and the L chain cDNA library of KM1334 produced in (2) above were detected using ECL Direct Nucleic Acid Labelling and Detection Systems (manufactured by Amersham Biosciences) according to the attached manual upon employing cDNAs of a C region of a mouse antibody [a DNA fragment comprising mouse Cγ1 cDNA (French D. L. et al., J. Immunol., 146, 2010-2016, 1991) as H chain and a DNA fragment comprising mouse Cκ cDNA (Hieter P. A. et al., Cell, 22, 197-207, 1980) as L chain] as probes to obtain 10 phage clones strongly bound to the probe for each of H chain and L chain. The respective phage clones were then converted to plasmids by in vivo excision according to the manual of λZAPII Cloning Kit (manufactured by Stratagene). The nucleotide sequence of the cDNA comprised in each of the thus-obtained plasmids was determined using Big Dye Terminator Kit Ver. 2 (manufactured by Applied Biosystems) and a DNA sequencer. As a result, plasmid pKM1334H7-1 comprising the full length functional H chain cDNA and plasmid pKM1334L7-1 comprising the full length functional L chain cDNA in which ATG sequence deduced as initiation codon was present in the 5'-terminal of the cDNA were obtained.

(4) Analysis of Amino Acid Sequences of V Regions of an Anti-FGF-8 Neutralizing Mouse Antibody The full length nucleotide sequence of VH comprised in the plasmid pKM1334H7-1 is described in SEQ ID NO. 1, the deduced full length amino acid sequence in SEQ ID NO. 2, the full length nucleotide sequence of VL comprised in the plasmid pKM1334L7-1 in SEQ ID NO. 3, and the deduced full length amino acid sequence in SEQ ID NO. 4 respectively. In comparison to the sequence data of the known mouse antibody (Sequences of Proteins of Immunological Interest) and in comparison to the results of analyzing the N-terminal amino acid sequences of H chain and L chain of the purified anti-FGF-8 neutralizing mouse antibody KM1334 through automatic Edman degradation using Protein Sequencer PPSQ-10 (manufactured by Shimadzu Corporation), each of the isolated cDNAs is the full length cDNAs encoding the anti-FGF-8 neutralizing mouse antibody KM1334 comprising a secretory signal sequence. Regarding H chain, the 1st to 19th sequence of the amino acid sequence described in SEQ ID NO. 2 and regarding L chain, the 1st to 19th sequence of the amino acid sequence described in SEQ ID NO. 4 were found to be the secretory signal sequences. The amino acid sequences of VH and VL except for the secretory signal sequences were described in SEQ ID NO. 5 and SEQ ID NO. 6 respectively.

Next, the novelty of the amino acid sequences of VH and VL of the anti-FGF-8 neutralizing mouse antibody KM1334 was examined. The existing protein amino acid sequence database [PIR-Protein (Release 56.0)] was searched by BLAST (Altschul S. F. et al., J. Mol. Biol., 215, 403-410, 1990) using GCG Package (Version 9. 1, manufactured by Genetics Computer Group) as a sequence analysis system. As a result, completely identical sequences were not found regarding both of H chain and L chain, and VH and VL of the anti-FGF-8 neutralizing mouse antibody KM1334 were confirmed to be the novel amino acid sequences.

CDRs of VH and VL of the anti-FGF-8 neutralizing mouse antibody KM1334 were identified in comparison to the amino acid sequence of the known antibody. The amino acid sequences of CDR1, CDR2 and CDR3 of VH of the anti-FGF-8-neutralizing mouse antibody KM1334 were described in SEQ ID NOS. 7, 8 and 9, and the amino acid sequences of CDR1, CDR2 and CDR3 of VL of the anti-FGF-8-neutralizing mouse antibody KM1334 were described in SEQ ID NOS. 10, 11 and 12 respectively.

2. Stable Expression of Anti-FGF-8-Neutralizing Chimeric Antibody Using Animal Cells (1) Construction of Plasmid pKM1334CH-H5 Comprising a DNA Encoding VH of Anti-FGF-8-Neutralizing Chimeric Antibody Using 50 ng of the plasmid pKM1334H7-1 obtained in 1. (3) of Reference Example 1 as a template, synthetic DNAs (manufactured by GENSET) having nucleotide sequences described in SEQ ID NOS. 13 and 14 respectively were added as primers to give a final concentration of 0.3 μmol/Lol/L, and PCR was carried out by firstly heating 50 μl in total volume of the mixture at 94° C. for 2 minutes and subsequently 30 cycles of reactions at 94° C. for 15 seconds, 57° C. for 30 seconds and 68° C. for 1 minute as one cycle according to the manufacture's instructions attached to KOD plus polymerase (manufactured by TOYOBO). The reaction solution was purified, then dissolved in sterile water, and reacted at 37° C. for 1 hour using 10 units of restriction endonuclease EcoRI (manufactured by Takara Shuzo). The reaction solution was fractionated by agarose gel electrophoresis to recover approximately 0.3 μg of an EcoRI fragment (the 5'-terminal side is EcoRI, and the 3'-terminal side is a blunt end) of approximately 0.48 kb.

Then, 3 μg of plasmid pBluescript SK(−) was reacted with 10 units of restriction endonuclease EcoRI and 10 units of restriction endonuclease EcoRV (manufactured by Takara Shuzo) at 37° C. for 1 hour. The reaction solution was fractionated by agarose gel electrophoresis to recover approximately 2 μg of an EcoRI-EcoRV fragment of approximately 2.95 kb.

Figure 18:
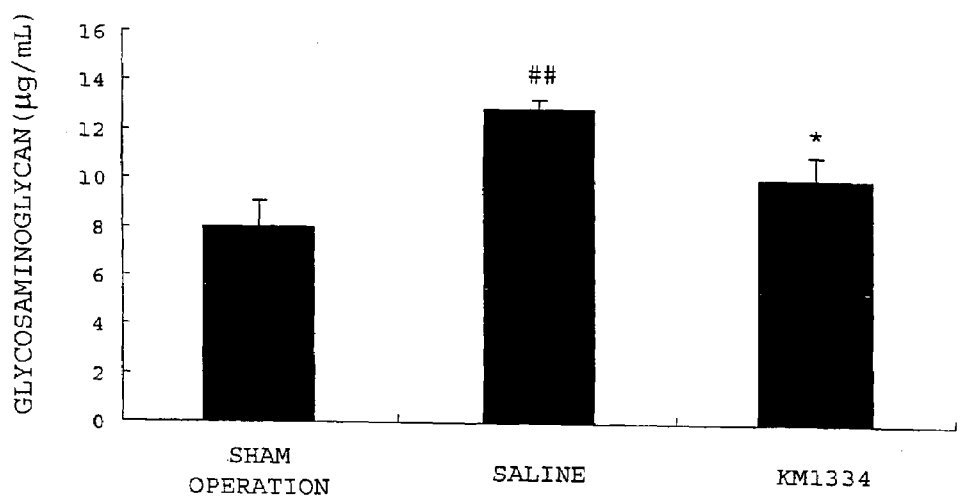
FIG. 18 is a graph showing inhibitory activity of anti-FGF-8 neutralizing antibody KM1334 to destruction of the articular cartilage in monoiodoacetic acid-induced osteoarthritis model rats. The ordinate represents a concentration (μg/mL) of glycosaminoglycan in a joint washing liquid. The values represent the mean values±the standard error, and ## indicates P<0.01 (compared to a sham operated group, Aspin-Welch test) and * indicates P<0.05 (compared to a saline administrated group, Aspin-Welch test).

Next, 0.1 μg of the EcoRI fragment of the DNA encoding VH and 0.1 μg of the EcoRI-EcoRV fragment derived from the plasmid pBluescript SK(−) as obtained above were added to sterile water in a total amount of 10 μl, and ligated using Ligation High (manufactured by Toyobo). *Escherichia coli* XL1-Blue strain was transformed using the thus-obtained recombinant plasmid DNA solution to obtain plasmid pKM1334CH-H5 comprising the DNA encoding VH of the anti-FGF-8 neutralizing chimeric antibody as shown in FIG. 18.

(2) Construction of a Plasmid Comprising a DNA Encoding VL of an Anti-FGF-8 Neutralizing Chimeric Antibody Using 50 ng of the plasmid pKM1334H7-1 obtained in 1. (3) of Reference Example 1 as a template, synthetic DNAs (manufactured by GENSET) having nucleotide sequences described in SEQ ID NOS. 15 and 16 respectively were added as primers to give a final concentration of 0.3 μmol/L, and PCR reaction was carried out by firstly heating 50 μl in total volume of the mixture at 94° C. for 2 minutes and subsequently 30 cycles of reactions at 94° C. for 15 seconds, 57° C. for 30 seconds and 68° C. for 1 minute as one cycle according to the manufacture's instructions attached to KOD plus polymerase. The reaction solution was purified, then dissolved in sterile water, and reacted at 37° C. for 1 hour using 10 units of restriction endonuclease EcoRI. The reaction solution was fractionated by agarose gel electrophoresis to recover approximately 0.3 μg of an EcoRI fragment (the 5'-terminal side is EcoRI, and the 3'-terminal side is a blunt end) of approximately 0.45 kb.

Figure 19:
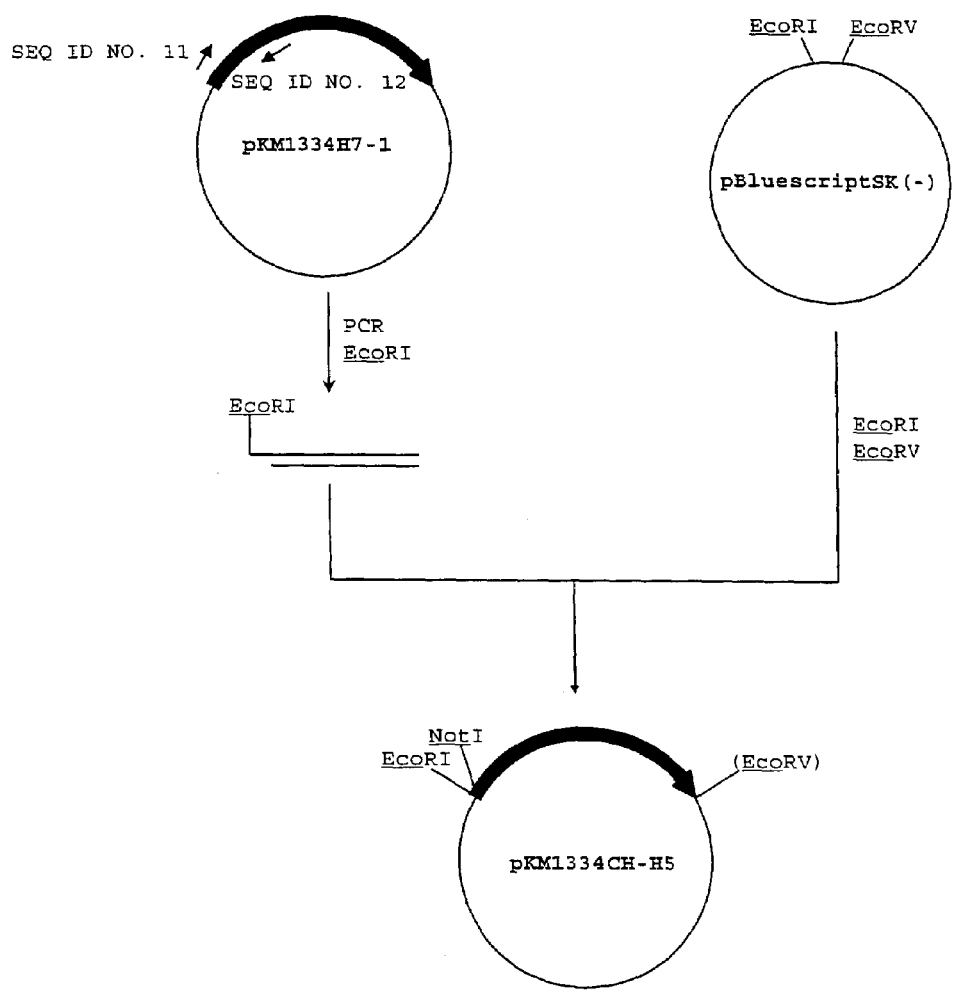
FIG. 19 is a flow chart showing construction of plasmid pKM1334CH-H5.

Next, 0.1 μg of the EcoRI fragment of the DNA encoding VL and 0.1 μg of the EcoRI-EcoRV fragment derived from the plasmid pBluescript SK (−) as obtained above were added to sterile water in a total amount of 10 μl, and ligated using Ligation High. *Escherichia coli* XL1-Blue strain was transformed using the thus-obtained recombinant plasmid DNA solution to obtain the plasmid pKM1334CH-L4 comprising the DNA encoding VL of the anti-FGF-8 neutralizing chimeric antibody as shown in FIG. 19.

(3) Construction of Anti-FGF-8 Neutralizing Chimeric Antibody Expression Vector pKANTEX1334

Anti-FGF-8 neutralizing chimeric antibody expression vector pKANTEX1334 was constructed in the following manner using the vector pKANTEX93 for humanized antibody expression described in WO 97/10354 and the plasmids pKM1334CH-H5 and pKM1334CH-L4 obtained in 2. (1) and (2) of Reference Example 1.

First, 10 units of restriction endonuclease NotI (manufactured by New England Biolabs) and 10 units of restriction endonuclease ApaI (manufactured by Takara Shuzo) were added to 3 μg of the plasmid pKM1334CH-H5 obtained in 2. (1) of Reference Example 1, and a reaction was performed at 37° C. for 1 hour. The reaction solution was fractionated by agarose gel electrophoresis to recover approximately 0.2 μg of a NotI-ApaI fragment of approximately 0.48 kb.

Then, 3 μg of the vector pKANTEX93 for humanized antibody expression was added with 10 units of restriction endonuclease ApaI (manufactured by Takara Shuzo) and 10 units of restriction endonuclease NotI and a reaction was performed at 37° C. for 1 hour. The reaction solution was fractionated by agarose gel electrophoresis to recover approximately 2 μg of an ApaI-NotI fragment of approximately 12.8 kb.

Figure 20:
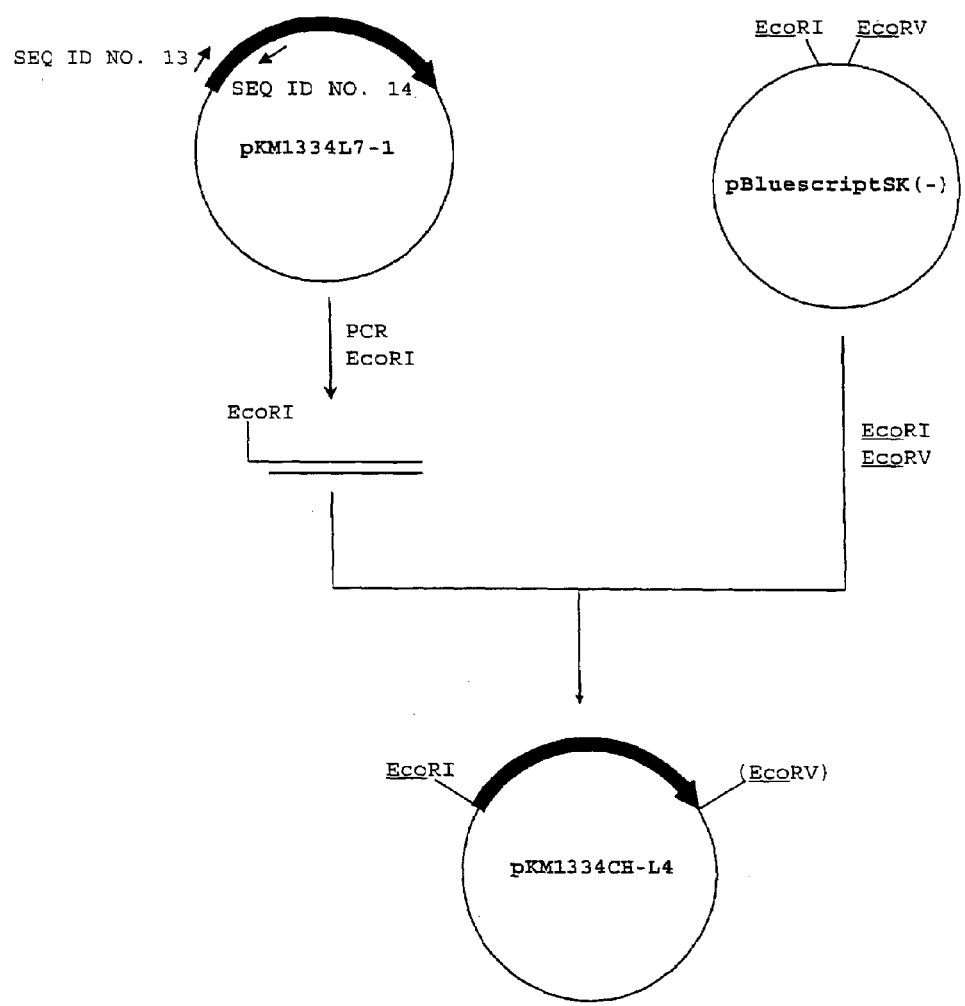
FIG. 20 is a flow chart showing construction of plasmid pKM1334CH-L4.

Next, 0.1 μg of the NotI-ApaI fragment derived from the plasmid pKM1334CH-H5 and 0.1 μg of the NotI-ApaI fragment derived from the plasmid pKANTEX93 as obtained above were added to sterile water in a total amount of 10 μL, and ligated using Ligation High. *Escherichia coli* XL1-Blue strain was transformed using the thus-obtained recombinant plasmid DNA solution to obtain plasmid pKANTEX1334H shown in FIG. 20.

Then, 10 units of restriction endonuclease EcoRI and 10 units of restriction endonuclease BsiWI (manufactured by New England BioLabs) were added to 3 μg of the plasmid pKM1334CH-L4 obtained in 2. (2) of Reference Example 1, and a reaction was performed at 37° C. for 1 hour. The reaction solution was fractionated by agarose gel electrophoresis to recover approximately 0.2 μg of an EcoI-BsiWI fragment of approximately 0.45 kb.

Then, 3 μg of the above-obtained plasmid pKANTEX1334H was reacted with 10 units of restriction endonuclease EcoRI and 10 units of restriction endonuclease BsiWI at 37° C. for 1 hour. The reaction solution was fractionated by agarose gel electrophoresis to recover approximately 2 μg of an EcoRI-BsiWI fragment of approximately 13.30 kb.

Then, 0.1 μg of the EcoRI-BsiWI fragment derived from the plasmid pKM1334CH-L4 and 0.1 μg of the EcoRI-BsiWI fragment derived from the plasmid pKANTEX1334H as obtained above were added to sterile water in a total amount of 10 μL, and ligated using Ligation High. *Escherichia coli* XL1-Blue strain was transformed using the thus-obtained recombinant plasmid DNA solution to obtain plasmid pKANTEX1334 shown in FIG. 20.

Using 400 ng of the resulting plasmid pKANTEX1334, analysis of the nucleotide sequence was performed using Big Dye Terminator Kit Ver. 2 and a DNA sequencer. As a result, it was confirmed that the plasmid with the desired DNA cloned was obtained.

(4) Stable Expression of an Anti-FGF-8 Neutralizing Chimeric Antibody Using CHO/DG44 Cells The expression of the anti-FGF-8 neutralizing chimeric antibody using CHO/DG44 cells (Urlaub G. and Chasin L. A., Proc. Natl. Acad. Sci. USA, 77, 4216-4220, 1980) being DHFR gene-deficient CHO cells as a host was performed with the anti-FGF-8 neutralizing chimeric antibody expression vector pKANTEX1334 obtained in 2. (3) of Reference Example 1 in the following manner.

10 μg of the plasmid pKANTEX1334 was introduced into $1.6 \times 10^6$ CHO/DG44 cells by the electroporation method (Miyaji H. et al., Cytotechnology 3, 133-140, 1990), and resulting cells were then suspended in 10 to 30 mLIMDM-1×HT Supplement-dFBS(10) [IMDM medium (manufactured by Invitrogen) containing 10% of Dialysis FBS (hereinafter abbreviated as DFBS) and 1×HT Supplement (manufactured by Invitrogen)]. The suspension was dispensed at a 96-well microtiter plate (manufactured Asahi Techno Glass) in an amount of 100 μl/well. After the culturing in a 5% $CO_2$ incubator at 37° C. for 24 hours, the culture solution was replaced with IMDM-dFBS(10) medium (IMDM medium not containing HT Supplement but containing 10% DFBS), and the culturing was further performed for 1 to 2 weeks. The culture supernatant was recovered from the wells in which resistant colonies appeared and became confluent, and the antigen-binding activity of the anti-FGF-8 neutralizing chimeric antibody in the supernatant was measured by ELISA shown in 2. (6) of Reference Example 1 below.

The tranformants of the well in which the expression of the anti-FGF-8 neutralizing chimeric antibody was observed in the culture supernatant was inoculated on a 24-well plate, and cultured in IMDM-DFBS (10) containing 50 nmol/L of methotrexate (manufactured by Sigma-Aldrich, hereinafter abbreviated as MTX) as an inhibitor of dhfr for increasing the antibody expression amount with a dhfr gene amplification system for 2 weeks. Further, the MTX concentration was increased to 200 nmol/L and 500 nmol/L, and the culturing was performed for 2 weeks at each stage to induce a tranformants showing the 500 nmol/L MTX resistance. When the tranformants became confluent in the well, the antigen-binding activity of the anti-FGF-8 neutralizing chimeric antibody in the culture supernatant was measured by ELISA described in 2. (6) of Reference Example 1. The tranformants capable of growth in IMDM-dFBS(10) medium containing 500 nmol/L of MTX and highly expressing the anti-FGF-8 neutralizing chimeric antibody was finally obtained. The resulting tranformants was made into single cell (subjected to cloning) by the limiting dilution method, and the tranformants clone showing the highest expression of the anti-FGF-8 neutralizing chimeric antibody was designated KM3034. KM3034 was deposited as FERM BP-7836 in International Patent Organism Depositary, National Institute of Advanced Industrial Science and Technology (AIST Tsukuba Central 6, 1-1-1 Higashi, Tsukubashi Ibaraki, 305-8566, Japan) on Dec. 26, 2001.

(5) Stable Expression of an Anti-FGF-8 Neutralizing Chimeric Antibody Using YB2/0 Cells The expression of the anti-FGF-8 neutralizing chimeric antibody in rat hybridoma YB2/0 cells (ATCC No. CRL-1662) was performed in the following manner using the anti-FGF-8 neutralizing chimeric antibody expression vector pKANTEX1334 obtained in 2. (3) of Reference Example 1 above.

10 μg of the plasmid pKANTEX1334 was introduced into $4\times10^6$ YB2/0 cells by the electroporation method, and the resulting cells were then suspended in 40 mL of hybridoma-SFM-FBS(5) [hybridoma-SFM medium (manufactured by Invitrogen) containing of 5% FBS (manufactured by PAA Laboratories). The suspension was dispensed on a 96-well culture plate (manufactured Sumitomo Bakelite) in an amount of 200 μl/well. After the culturing in a 5% $CO_2$ incubator at 37° C. for 24 hours, G418 was added to a concentration of 1 mg/mL, and the culturing was performed for 1 to 2 weeks. The culture supernatant was recovered from the wells in which colonies of the tranformants showing G418 resistance appeared and the growth was observed, and the antigen-binding activity of the anti-FGF-8 neutralizing chimeric antibody in the supernatant was measured by ELISA described in 2. (6) of Reference Example 1.

The tranformants of the well in which the expression of the anti-FGF-8 neutralizing chimeric antibody was observed in the culture supernatant was suspended in hybridoma-SFM-FBS (5) medium containing 1 mg/mL G418 and 50 nmol/L MTX to a concentration of 1 to $2\times10^5$ cells/mL for increasing the antibody expression amount with a dhfr gene amplification system, and the suspension was dispensed on a 24 well plate (manufactured by Greiner) in an amount of 1 mL/well. The culturing was performed in a 5% $CO_2$ incubator at 37° C. for 1 to 2 weeks to induce a transformed line having 50 nmol/L MTX resistance. The antigen-binding activity of the anti-FGF-8 neutralizing chimeric antibody in the culture supernatant of the well in which the growth of the tranformants was observed was measured by ELISA described in 2. (6) of Reference Example 1.

With respect to the transformed line of the well in which the expression of the anti-FGF-8 neutralizing chimeric antibody was observed in the culture supernatant, the MTX concentration was increased by the foregoing method to obtain transformed line 5-D capable of growth in hybridoma-SFM-FBS (5) medium containing G418 at a final concentration of 1 mg/mL and MTX at a final concentration of 200 nmol/L and highly expressing the anti-FGF-8 neutralizing chimeric antibody. The resulting tranformants was subjected to cloning by the limiting dilution method to obtain the tranformants line showing the highest expression of the anti-FGF-8 neutralizing chimeric antibody. The thus-obtained tranformants line was designated KM3334.

(6) Measurement of Binding Activity of an Antibody for an FGF-8 Partial Peptide by ELISA A peptide comprising an amino acid sequence represented by SEQ ID NO. 17 which is the same as that of an antigen peptide of anti-FGF-8 neutralizing mouse antibody KM1334 (Japanese published unexamined application No. 271391/97) was synthesized as a partial peptide of human FGF-8 capable of reacting with the anti-FGF-8 antibody. SEQ ID NO. 17 is a sequence in which a cysteine residue for preparation of a conjugate is added to the C-terminal of the 23rd to 46th sequence in the amino acid sequence of human FGF-8. This peptide is hereinafter referred to as compound 1. A conjugate with bovine serum albumin (manufactured by Nacalai Tesque, hereinafter abbreviated as BSA) (hereinafter referred to as BSA-compound 1) was produced by the following method for use in ELISA. That is, 100 μl of 25 mg/ml SMCC [4-(N-maleimidomethyl)cyclohexane-1-carboxylic acid N-hydroxysuccinimide ester] (manufactured by Sigma-Aldrich)-DMSO solution was added dropwise under stirring to 900 μl of PBS solution comprising 10 mg of BSA, followed by slowly stirring for 30 minutes. 1 mL of the reaction solution was put on a gel filtration column (NAP-10 column) equilibrated with 25 mL of PBS, and eluted with 1.5 mL of PBS. The resulting elute was designated a BSA-SMCC solution. The BSA concentration of each fraction was measured in terms of absorbance at 280 nm. Subsequently, 200 μL DMSO was added to 1.0 mg of compound 1, and 800 μL PBS was then added to completely dissolve them. The foregoing BSA-SMCC solution (2.5 mg as calculated in terms of BSA) was added while being stirred, and the mixture was gently stirred at room temperature for 3 hours. The reaction solution was dialyzed against PBS overnight at 4° C., and sodium azide was added such that the final concentration became 0.05%. Thereafter, the mixture was filtrated through a filter having a pore diameter of 0.22 μm, and the resulting solution was designated a BSA-compound 1 solution.

The above-prepared BSA-compound 1 solution was dispensed at a 96-well ELISA plate (manufactured by Greiner) at a concentration of from 0.5 to 1.0 μg/mL in an amount of 50 μL/well, and allowed to stand overnight at 4° C. for adsorption. After washing with PBS, 1% BSA-containing PBS (hereinafter referred to as BSA-PBS) was added in an amount of 100 μL/well and reacted at room temperature for 1 hour to block a remaining active group. After washing each well with 0.05% Tween-containing PBS (hereinafter referred to as Tween-PBS), the culture supernatant or the purified antibody of the tranformants was added in an amount of 50 μL/well, and the reaction was conducted at room temperature for 1 hour. After the reaction, each well was washed with Tween- PBS, a peroxidase-labeled goat anti-human IgG (H & L) antibody solution (manufactured by American Qualex) diluted 3,000 to 6,000 times with BSA-PBS was added as a second antibody solution in an amount of 50 μL/well. The reaction was performed at room temperature for 1 hour. After the reaction, each well was washed with Tween-PBS, an ABTS substrate solution [solution obtained by dissolving 0.55 g of ammonium 2,2'-azino-bis(3-ethylbenzothiazolin-6-sulfonate) in 1 L of 0.1 M citrate buffer solution (pH 4.2) and adding a 30% hydrogen peroxide solution at a ratio of 1 μL/mL immediately before use] was added in an amount of 50 μL/well to allow a color development reaction. 5 minutes later, a 5% SDS solution was added in an amount of 50 μL/well to stop the reaction. Then, absorbance was measured at 415 nm.

3. Purification of an Anti-FGF-8 Neutralizing Chimeric Antibody (1) Culturing of Expression Cells Derived from CHO/DG44 Cells and Purification of an Antibody The tranformants line KM3034 expressing the anti-FGF-8 neutralizing chimeric antibody obtained in 2. (4) of Reference Example 1 was suspended in IMDM-DFBS (10) medium containing 500 nmol/L MTX to a concentration of 1 to $2\times10^5$ cells/mL, and the suspension was dispensed at a 175 cm² flask (manufactured by Greiner) in an amount of 40 mL. The culturing was performed in a 5% $CO_2$ incubator at 37° C. for from 5 to 7 days. When the cells became confluent, the culture supernatant was removed, and the cells were washed with 20 mL of PBS. PBS was removed, and 40 mL of EX-CELL 301 medium (manufactured by JRH Biosciences) was added. The culturing was performed in a 5% $CO_2$ incubator at 37° C. for 7 to 14 days, and the culture supernatant was then recovered. The anti-FGF-8 neutralizing chimeric antibody was purified from the culture supernatant using Prosep-A (manufactured by Millipore) column according to the attached manual. The resulting anti-FGF-8 neutralizing chimeric antibody was designated KM3034.

(2) Culturing of Expression Cells Derived from YB2/0 Cells and Purification of an Antibody The tranformants line KM3334 expressing the anti-FGF-8 neutralizing chimeric antibody as obtained in 2. (5) of Reference Example 1 was cultured with a 175 cm² flask in a 5% $CO_2$ incubator at 37° C. using hybridoma-SFM medium containing 200 nmol/L MTX and 5% Daigo's GF21 (manufactured by Wako Pure Chemical Industries, Ltd.). The culturing was performed for 8 to 10 days, and the culture supernatant was recovered. From the culture supernatant, the anti-FGF-8 neutralizing chimeric antibody was purified using Prosep-A column according to the attached manual. The thus-obtained anti-FGF-8 neutralizing chimeric antibody was designated KM3334.

4. Analysis of Purified Anti-FGF-8 Neutralizing Chimeric Antibodies

4 μg of each of two anti-FGF-8 neutralizing chimeric antibodies KM3034 and KM3334 expressed in various animal cells and purified as obtained in 3. of Reference Example 1 was subjected to SDS-electrophoresis according to the known method (Nature, 227, 680, 1970) to analyze the molecular weight and the purity. In each of the purified anti-FGf-8 neutralizing chimeric antibodies, a single band with a molecular weight of approximately 150 Kd was observed under a non-reductive condition and two bands with molecular weights of approximately 50 Kd and approximately 25 Kd under a reducing. These molecular weights were nearly consistent with molecular weights (H chain: approximately 49 Kd, L chain: approximately 23 Kd, total molecular weight: approximately 144 Kd) estimated from nucleotide sequences of cDNAs of H chain and L chain of the antibody. Moreover, the IgG-type antibody was consistent with the report that the molecular weight is approximately 150 Kd under a non-reducing condition and the S—S bond in the molecule is cut whereby the molecule is degraded into H chain having a molecular weight of approximately 50 Kd and L chain having a molecular weight of approximately 25 Kd under a reducing condition (Antibodies: A Laboratory Manual, Cold Spring Harbor Laboratory, Chapter 14, 1988; Monoclonal Antibodies: Principles and Practice, Academic Press Limited, 1996). Consequently, it was confirmed that the anti-FGF-8 neutralizing chimeric antibody was expressed and purified as an antibody molecule of a correct structure.

Figure 21:
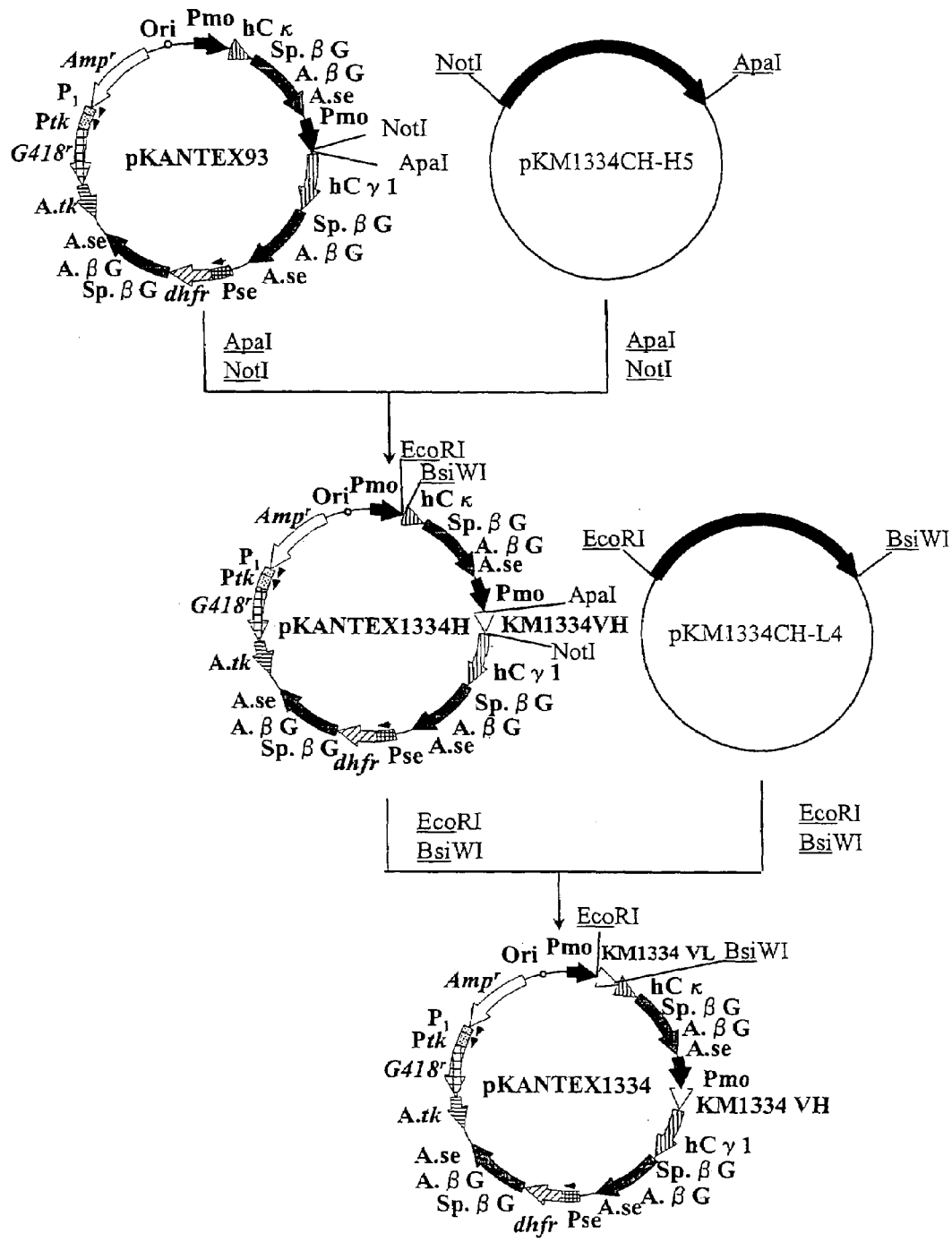
FIG. 21 is a flow chart showing construction of plasmid pKANTEX1334.

5. Evaluation of Neutralizing Activity of a Purified Anti-FGF-8 Neutralizing Chimeric Antibody The FGF-8 neutralizing activity of the purified anti-FGF-8 neutralizing chimeric antibody was evaluated by measured the following FGF-8-dependent growth inhibitory effect of mouse breast cancer cell line SC-3 (Tanaka A. et al., Proc. Natl. Acad. Sci. USA, 89, 8928-8932, 1992) described below. That is, SC-3 cells were suspended at a concentration of $3.0\times10^4$ cells/mL in DMEM:Ham's F12 (1:1) medium [a mixed medium of DMEM medium and Ham's F12 medium (manufactured by Invitrogen) at a ratio of 1:1] containing activated charcoal-treated FBS at a concentration of 2%. The suspension was inoculated on a 96-well plate in an amount of 150 μL ($4.5\times10^3$ cells)/well. After the culturing in a 5% $CO_2$ incubator at 37° C. for 18 hours, the medium was replaced with 100 μL/well of a test medium. The test medium was produced by dissolving 50 ng/mL of FGF-8 (manufactured by R & D) and the anti-FGF-8 neutralizing chimeric antibody at each dilute concentration in DMEM:Ham's F12 (1:1) medium containing 0.1% BSA. The chimeric antibody KM2760 to human chemokine CCR4 described in WO 01/64754 was used as an antibody of a negative control. After the culturing in a 5% $CO_2$ incubator at 37° C. for 48 hours, the medium was replaced with a freshly prepared test medium, and the culturing was further performed for 48 hours. WST-1 Reagent (manufactured by Roche) was added in an amount of 10 μL/well, and the mixture was culturing in a 5% $CO_2$ incubator at 37° C. for 1 hour while being gently stirred. Then, absorbance ($OD_{450,650}$) was measured. In FIG. 21, the abscissa represents a concentration of an antibody added, and the ordinate represents relative growth (%) to growth when adding 50 ng/mL of FGF-8 alone. The relative growth (%) to growth when adding 50 ng/mL of FGF-8 alone was calculated by the following formula.

Relative growth (%) to growth when adding *FGF*-8=
{(Absorbance when adding *FGF*-8 and antibody−Absorbance when not adding *FGF*-8 and antibody)/(Absorbance when adding *FGF*-8 alone−Absorbance when not adding *FGF*-8 and antibody)}×100

As shown in FIG. 21, all of the anti-FGF-8 neutralizing mouse antibody KM1334 and anti-FGF-8 neutralizing chimeric antibodies KM3034 and KM3334 exhibited the similar SC-3 cell growth inhibitory activity without observing the decrease in neutralizing activity by the change to the chimeric antibody.

REFERENCE EXAMPLE 2

Preparation of an Anti-FGF-8 Neutralizing CDR-grafted Antibody

1. Construction of DNAs Encoding VH and VL of an Anti-FGF-8 Neutralizing CDR-Grafted Antibody (1) Designing of Amino Acid Sequences of VH and VL of an Anti-FGF-8 Neutralizing CDR-grafted Antibody First, the amino acid sequence of VH of the anti-FGF-8 neutralizing CDR-grafted antibody was designed as follows. The amino acid sequence of FR of VH of the human antibody for grafting the amino acid sequence of CDR of VH of the anti-FGF-8 neutralizing mouse antibody KM1334 identified in 1. (4) of Reference Example 1 was selected. Kabat et al. have classified VHs of various known human antibodies into three subgroups (HSG I to III) according to the homology of their amino acid sequences, and have further reported common sequences in the respective subgroups (Sequences of Proteins of Immunological Interest). Since it is considered in these common sequences that the immunogenicity might be more decreased in humans, the amino acid sequence of VH of the anti-FGF-8 neutralizing CDR-grafted antibody was decided to be designed on the basis of these common sequences. For preparing the anti-FGF-8 neutralizing CDR-grafted antibody having the higher activity, the amino acid sequence of FR having the highest homology to the amino acid sequence of FR of VH of KM1334 was selected in the designing among the amino acid sequences of FRs of the common sequences of the three subgroups of VH of the human antibody. Table 4 showed the results of homology search. As shown in Table 4, the amino acid sequence of FR of the VH region of KM1334 had the highest homology to subgroup I.

TABLE 4

Homology between the amino acid sequence of FR in consensus sequence of each subgroup of human antibody VH and the amino acid sequence of FR in VH of KM1334

| HGS I | HSG II | HSG III |
|---|---|---|
| 79.3% | 51.7% | 59.8% |

From the foregoing results, the amino acid sequence of CDR in VH of the anti-FGF-8 neutralizing mouse antibody KM1334 was grafted on an appropriate position of the amino acid sequence of FR in consensus sequence of subgroup I of human antibody VH to design amino acid sequence HV.0 of VH of the anti-FGF-8 neutralizing CDR-grafted antibody described in SEQ ID NO. 18.

Subsequently, the amino acid sequence of VL of the anti-FGF-8 neutralizing CDR-grafted antibody was designed as follows. The amino acid sequence of FR in VL of the human antibody for grafting the amino acid sequence of CDR in VL of the anti-FGF-8 neutralizing mouse antibody KM1334 identified in 1. (4) of Reference Example 1 was selected. Kabat et al. have classified VLs of various known human antibodies into four subgroups (HSG I to IV) according to the homology of their amino acid sequences, and have further reported consensus sequences in the respective subgroups (Sequences of Proteins of Immunological Interest). Therefore, in the same manner as in the case of VH, the amino acid sequence of FR having the highest homology to the amino acid sequence of FR of VL of KM1334 was selected from among the amino acid sequences of FRs of the common sequences of the four subgroups of VL of the human antibody.

Table 5 showed the results of homology search. As shown in Table 5, the amino acid sequence of FR of VL of KM1334 had the highest homology to subgroup II.

TABLE 5

Homology between the amino acid sequence of FR in consensus sequence of each subgroup of human antibody VL and the amino acid sequence of FR in VL of KM1334

| HSG I | HSG II | HSG III | HSG IV |
|---|---|---|---|
| 66.3% | 83.8% | 66.2% | 73.8% |

From the foregoing results, the amino acid sequence of CDR of VL of the anti-FGf-8 neutralizing mouse antibody KM1334 was grafted on an appropriate position of the amino acid sequence of FR of the consensus sequence of subgroup II of VL of the human antibody to design amino acid sequence LV.0 of VL of the anti-FGF-8 neutralizing CDR-grafted antibody described in SEQ ID NO. 19.

Amino acid sequence HV.0 of VH and amino acid sequence LV.0 of VL of the anti-FGF-8 neutralizing CDR-grafted antibody as designed above are sequences in which only the amino acid sequence of CDR of the anti-FGF-8 neutralizing mouse antibody KM1334 is grafted on the selected amino acid sequence of FR in the human antibody. In the human CDR-grafted antibody, the binding activity is decreased, in many cases, by the mere grafting of the amino acid sequence of CDR of the mouse antibody. In order to avoid this, upon comparing the FR amino acid sequences of the human antibody and the mouse antibody, the amino acid residue considered to influence the binding activity among the different amino acid residues of FR has been grafted along with the amino acid sequence of CDR. In this Reference Example as well, the identification of the amino acid residue of FR which considered to influence the binding activity was examined.

First, the three-dimensional structure of the antibody V region (HV0LV0) comprising amino acid sequence HV.0 of VH and amino acid sequence LV.0 of VL of the anti-FGF-8 neutralizing CDR-grafted antibody as designed above was constructed by the computer modeling method. The three-dimensional structure coordinates were prepared using Software AbM (manufactured by Oxford Molecular), and the display of the three-dimensional structure was performed using Software Pro-Explore (manufactured by Oxford Molecular) or RasMol (manufactured by Glaxo) according to the attached manual. The computer model of the three-dimensional structure of the V region of the anti-FGF-8 neutralizing mouse antibody KM1334 was constructed in the same manner. Furthermore, with respect to the amino acid sequences of FRs of VH and VL of HV0LV0, a V region three-dimensional structure model of a variant comprising an amino acid sequence in which amino acid residues different from those of the anti-FGF-8 neutralizing mouse antibody KM1334 were replaced in order with the amino acid residues found in corresponding positions of the anti-FGF-8 neutralizing mouse antibody KM1334 was constructed in the same manner. The three-dimensional structures of the V regions of the anti-FGF-8 neutralizing mouse antibody KM1334, HV0LV0 and the variant were compared. Consequently, as the residues considered to change the three-dimensional structure of the antigen-binding site and influence the activity of the antibody among the amino acid residues of FR of HV0LV0, Lys at position 12, Lys at position 13, Ala at position 40, Pro at position 41, Met at position 48, Val at position 68, Ile at position 70, Thr at position 74, Thr at position 76, Glu at position 82, Arg at position 87 and Tyr at position 95 were selected in HV.0 and Ile at position 2, Val at position 3, Thr at position 14, Pro at position 15, Gin at position 50, Leu at position 51 and Tyr at position 92 in LV.0 respectively, and the amino acids were replaced. At least one or more of these selected amino acid residues was replaced with the amino acid residue found in the mouse antibody KM1334, and VH and VL of the human CDR-grafted antibody with various replacements were designed as follows.

Specifically, amino acid sequence HV.6 described in SEQ ID NO. 20 in which 6 residues, Lys at position 12, Lys at position 13, Ala at position 40, Pro at position 41, Met at position 48 and Tyr at position 95 were replaced with Ala, Arg, Arg, Ser, Ile and Phe as the amino acid residues found in mouse antibody KM1334 respectively was designed as VH. Amino acid sequence LV.6 described in SEQ ID NO. 21 in which 6 residues, Ile at position 2, Thr at position 14, Pro at position 15, Gln at position 50, Leu at position 51 and Tyr at position 92 were replaced with Val, Ser, Leu, Lys, Val and Phe as the amino acid residues found in the mouse antibody KM1334 respectively was designed as VL.

(2) Construction of a DNA Encoding VH of an Anti-FGF-8 Neutralizing CDR-Grafted Antibody A DNA encoding amino acid sequence HV.0 of VH of the anti-FGF-8 neutralizing CDR-grafted antibody designed in 1. (1) of Reference Example 2 was constructed by PCR as follows.

First, the secretory signal sequence (1st to 19th amino acid sequence of SEQ ID NO. 2) of H chain of the anti-FGF-8 neutralizing mouse antibody KM1334 was connected to the designed amino acid sequence. The resulting amino acid sequence was then converted to genetic codon. When two or more genetic codons are present for one aminoacid residue, the corresponding genetic codon was determined in consideration of the use frequency found in the nucleotide sequence of the gene of the antibody (Sequences of Proteins of Immunological Interest). The determined genetic codons were linked to design the nucleotide sequence of the DNA encoding the full antibody V region amino acid sequence. Sequences comprising restriction endonuclease recognition sequences for cloning to a vector for expression of humanized antibody were added to the 5'-terminal and the 3'-terminal of this nucleotide sequence, and sequences complementary to the sequence of M13 primer RV (manufactured by Takara Shuzo) and the sequence of M13 primer M4 (manufactured by Takara Shuzo) were further added to the 5'-terminal and the 3'-terminal respectively. The thus-designed nucleotide sequence (SEQ ID NO. 22) was divided into four sequences by 141 bases from the 5'-terminal side such that 20 bases in the end overlapped to chemically synthesize four DNAs comprising sequences represented by SEQ ID NOS. 23 to 26 which correspond to a sense chain, an anti-sense chain, a sense chain and an anti-sense chain of each sequence (manufactured by GENSET).

According to the manual attached to KOD Polymerase, a PCR reaction solution in a total amount of 50 µL was prepared using 0.1 µmol/L of each synthetic DNA, 0.5 µmol/L of M13 primer RV, 0.5 µmol/L of M13 primer M4 and 2.5 units of KOD Polymerase (manufactured by Toyobo) to perform PCR. Regarding the reaction conditions, the reaction solution was carried out by heating at 94° C. for 5 minutes, subsequent 25 cycles of the reactions at 94° C. for 30 seconds, 50° C. for 30 seconds 74° C. for 60 seconds as one cycle, and further heating at 74° C. for 5 minutes. The reaction solution was precipitated with ethanol, and dissolved in sterile water. The reaction was conducted at 37° C. for 1 hour using 10 units of restriction endonuclease EcoRI and 10 units of restriction endonuclease SpeI (manufactured by Takara Shuzo). The reaction solution was fractionated by agarose gel electrophoresis to recover approximately 0.3 µg of an EcoRI-SpeI fragment of approximately 0.47 kb.

Subsequently, 3 µg of plasmid pBluescript II SK(−) (manufactured by Stratagene) was reacted with 10 units of restriction endonuclease EcoRI and 10 units of restriction endonuclease SpeI at 37° C. for 1 hour. The reaction solution was fractionated by agarose gel electrophoresis to recover approximately 2.9 µg of an EcoRI-SpeI fragment of approximately 2.95 kb.

Figure 22:
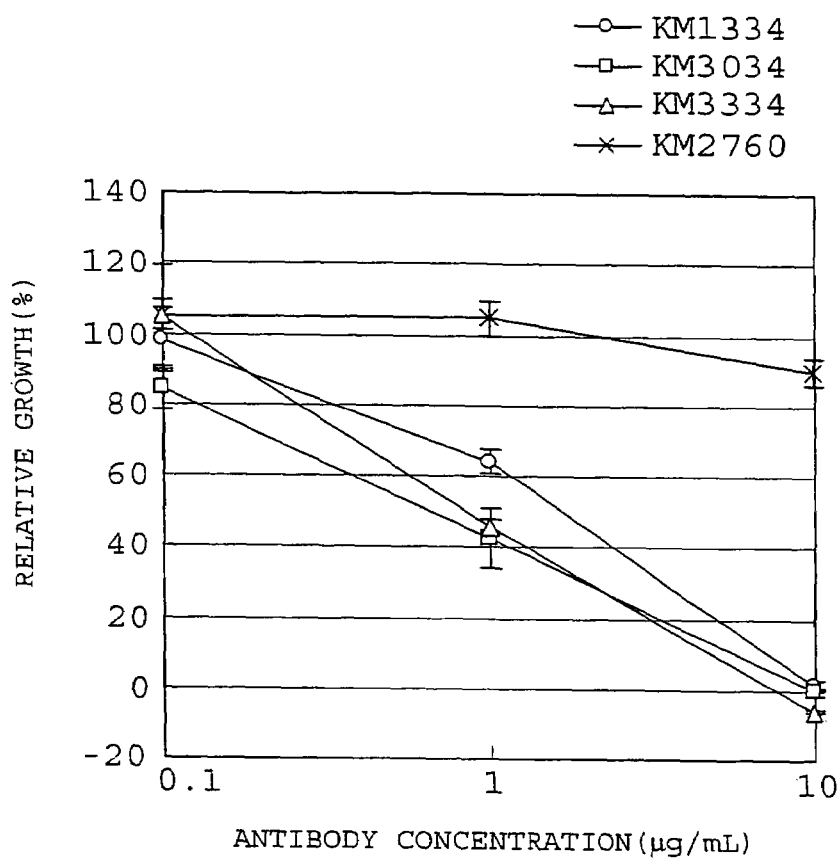
FIG. 22 is a graph showing neutralizing activity of anti-FGF-8 neutralizing mouse antibody KM1334 and anti-FGF-8 neutralizing chimeric antibodies KM3034 and KM3334 to the FGF-8 dependent growth of mouse breast cancer cell line SC-3. The abscissa represents an antibody concentration (μg/mL), and the ordinate represents the relative growth (%) when the growth in the addition of FGF-8 alone is defined as 100%. ○ indicates activity of KM1334, □ activity of KM3034; Δ activity of KM3334 and × activity of KM2760 as a negative control respectively.

Then, 0.1 µg of the EcoRI-SpeI fragment as the PCR product encoding VH of the anti-FGF-8 neutralizing CDR-grafted antibody and 0.1 µg of the EcoRI-SpeI fragment of the plasmid pBluescript II SK(−) as obtained above were added to sterile water in a total amount of 10 µL, and ligated using Ligation High. *Escherichia coli* DH5α strain (manufactured by Toyobo) was transformed using the thus-obtained recombinant plasmid DNA solution, and plasmid DNAs were prepared from 10 clones of the transformant. The analysis of the nucleotide sequence was performed using Big Dye Terminator Kit Ver.2 and a DNA sequencer. As a result of analyzing the nucleotide sequence, the plasmid pKM1334HV0 having the desired nucleotide sequence as shown in FIG. 22 was obtained.

A DNA encoding amino acid sequence HV.6 of VH of the anti-FGF-8 neutralizing CDR-grafted antibody designed in 1. (1) of Reference Example 2 was designed in the same manner to the DNA encoding HV.0 (SEQ ID NO. 27), and constructed by PCR in the foregoing manner using four synthetic DNAs (manufactured by GENSET) comprising sequences described in SEQ ID NOS. 28 to 31. The same procedure as in pKM1334HV0 was repeated to obtain plasmid pKM1334HV6 comprising the DNA encoding HV.6.

(3) Construction of a DNA Encoding VL of an Anti-FGF-8 Neutralizing CDR-Grafted Antibody A DNA encoding amino acid sequence LV.0 of VL of the anti-FGF-8 neutralizing CDR-grafted antibody designed in 1. (1) of Reference Example 2 was designed in the same manner to the DNA encoding HV.0 (SEQ ID NO. 32). However, in the designing of the synthetic DNA, the secretory signal sequence (1st to 19th amino acid sequence of SEQ ID NO. 4) of L chain of the anti-FGF-8 neutralizing mouse antibody KM1334 was used as a secretory signal sequence. The DNA encoding LV.0 was constructed by PCR using the four synthetic DNAs (manufactured by GENSET) comprising sequences of SEQ ID NOS. 33 to 36 in the same manner to the DNA encoding HV.0. The same procedure as in pKM1334HV0 was repeated to obtain the plasmid pKM1334LV0 comprising the DNA encoding LV.0.

A DNA encoding amino acid sequence LV.6 of VL of the anti-FGF-8 neutralizing CDR-grafted antibody as designed in 1. (1) of Reference Example 2 was designed in the same manner to the DNA encoding LV.0 (SEQ ID NO. 37), and constructed by PCR using the four synthetic DNAs (manufactured by GENSET) comprising sequences of SEQ ID NOS. 38 to 41 in the foregoing manner. The same procedure as in pKM1334HV0 was repeated to obtain the plasmid pKM1334LV6 comprising the DNA encoding LV.6.

2. Construction of an anti-FGF-8 Neutralizing CDR-Grafted Antibody Expression Vector Anti-FGF-8 neutralizing CDR-grafted antibody expression vector pKANTEX1334HV0LV0 was constructed in the following manner using the vector pKANTEX93 for humanized antibody expression described in WO 97/10354 and the plasmids pKM1334HV0 and pKM1334LV0 obtained in 1. (2) and (3) of Reference Example 2.

3 μg of the plasmid pKM1334HV0 obtained in 1. (2) of Reference Example 2 was reacted with 10 units of restriction endonuclease ApaI and 10 units of restriction endonuclease NotI (manufactured by Takara Shuzo) at 37° C. for 1 hour. The reaction solution was fractionated by agarose gel electrophoresis to recover approximately 0.3 μg of an ApaI-NotI fragment of approximately 0.47 kb.

Then, 3 μg of the vector pKANTEX93 for humanized antibody expression was reacted with 10 units of restriction endonuclease ApaI and 10 units of restriction endonuclease NotI at 37° C. for 1 hour. The reaction solution was fractionated by agarose gel electrophoresis to recover approximately 2 μg of an ApaI-NotI fragment of approximately 12.8 kb.

Figure 23:
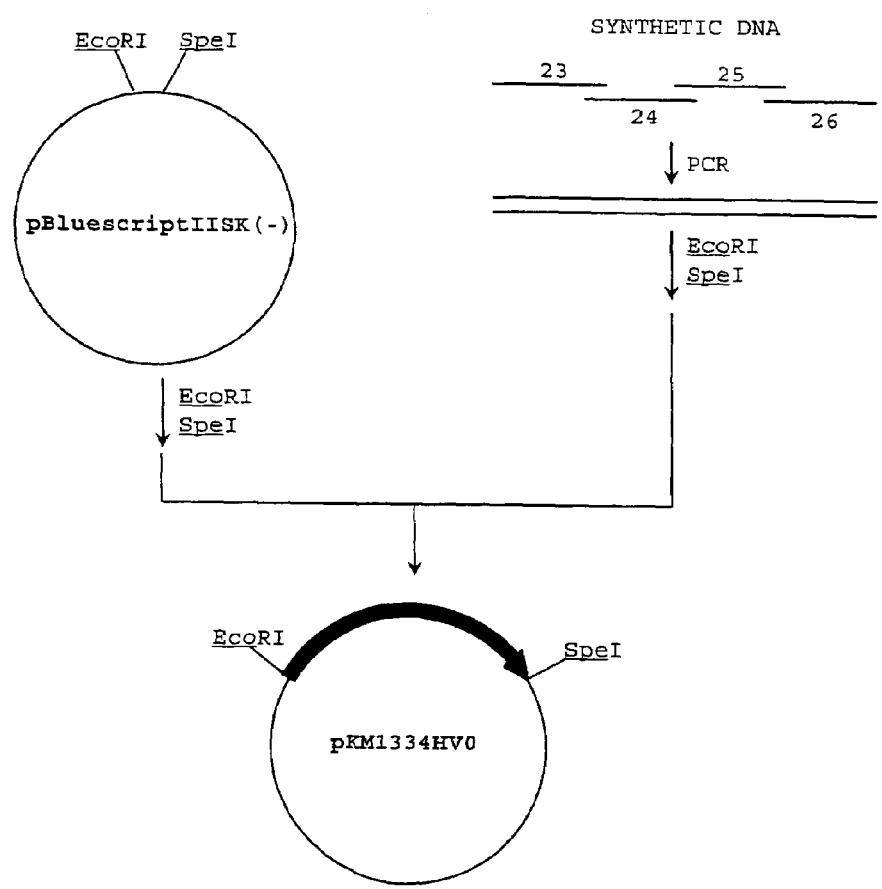
FIG. 23 is a flow chart showing construction of plasmid pKM1334HV0.

Then, 0.1 μg of the pKM1334HVO-derived NotI-ApaI fragment and 0.1 μg of the plasmid pKANTEX93-derived NotI-ApaI fragment as obtained above were added to sterile water in a total amount of 10 μL, and ligated using Ligation High. *Escherichia coli* DH5α strain was transformed using the thus-obtained recombinant plasmid DNA solution to obtain the plasmid pKANTEX1334HV0 shown in FIG. 23.

Subsequently, 3 μg of the plasmid pKM1334LV0 obtained in 1. (3) of Reference Example 2 was reacted with 10 units of restriction endonuclease EcoRI and 10 units of restriction endonuclease BsiWI at 37° C. for 1 hour. The reaction solution was fractionated by agarose gel electrophoresis to recover approximately 0.3 μg of an EcoRI-BsiWI fragment of approximately 0.45 kb.

Then, 3 μg of the above-obtained plasmid pKANTEX1334HV0 was reacted with 10 units of restriction endonuclease EcoRI and 10 units of restriction endonuclease BsiWI at 37° C. for 1 hour. The reaction solution was fractionated by agarose gel electrophoresis to recover approximately 2 μg of an EcoRI-BsiWI fragment of approximately 13.30 kb.

Then, 0.1 μg of the pKM1334LV0-derived EcoI-BsiWI fragment and 0.1 μg of the plasmid pKANTEX1334HV0-derived EcoI-BsiWI fragment as obtained above were added to sterile water in a total amount of 10 μL, and ligated using Ligation High. *Escherichia coli* DH5α strain was transformed using the thus-obtained recombinant plasmid DNA solution to obtain the expression vector pKANTEX1334HV0LV0 shown in FIG. 23.

Using 400 ng of the resulting plasmid, the nucleotide sequence was analyzed by Big Dye Terminator Kit Ver. 2 and a DNA sequencer. As a result, it was confirmed that the plasmid with the desired DNA cloned was obtained.

Expression vector pKANTEX1334HV0LV6 was constructed in the foregoing manner using the plasmid pKM1334HV0 obtained in 1. (2) of Reference Example 2 and the plasmid pKM1334LV6 obtained in 1. (3) of Reference Example 2.

Expression vector pKANTEX1334HV6LV6 was constructed in the foregoing manner using the plasmid pKM1334HV6 obtained in 1. (2) of Reference Example 2 and the plasmid pKM1334LV6 obtained in 1. (3) of Reference Example 2.

3. Stable Expression of Anti-FGF-8 Neutralizing CDR-Grafted Antibodies Using YB2/0 Cells The stable expression of various FGF-8 neutralizing CDR-grafted antibodies in YB2/0 cells was performed by the method described in 2. (5) of Reference Example 1 using the anti-FGF-8 neutralizing CDR-grafted antibody expression vectors, pKANTEX1334HV0LV0, pKANTEX1334HV0LV6 and pKANTEX1334HV6LV6 obtained in 2. of Reference Example 2.

4. Purification of Anti-FGF-8 Neutralizing CDR-Grafted Antibodies

The culturing of the YB2/0 cell-derived transformant expressing the various anti-FGF-8 neutralizing CDR-grafted antibodies obtained in 3. of Reference Example 2 and the purification of the anti-FGF-8 neutralizing CDR-grafted antibodies from the supernatant were performed by the method described in 3. (2) of Reference Example 1. The antibody derived from the transformant with pKANTEX1334HV0LV0 introduced was designated HV0LV0, the antibody-derived from the transformant with pKANTEX1334HV0LV6 introduced was designated HV0LV6, and the antibody derived from the transformant with pKANTEX1334HV6LV6 introduced was designated HV6LV6 respectively.

5. Analysis of Purified Anti-FGF-8 Neutralizing CDR-Grafted Antibodies

SDS-PAGE of the various anti-FGF-8 neutralizing CDR-grafted antibodies obtained in 4. of Reference Example 2 was performed by the method described in 4. of Reference Example 1. Consequently, it was confirmed that all of the antibodies were expressed as antibody molecules of the correct structures and purified.

Figure 24:
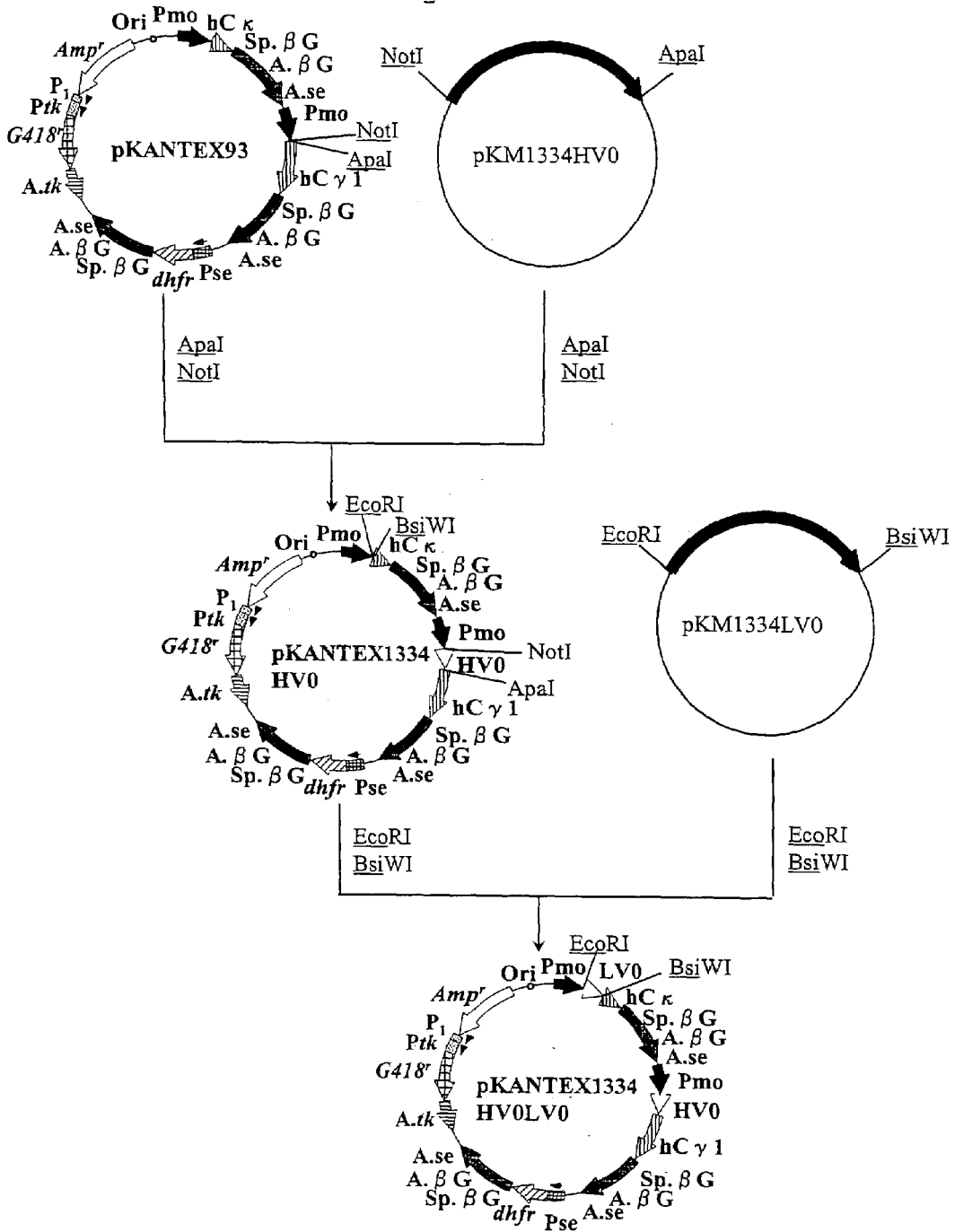
FIG. 24 is a flow chart showing construction of plasmid pKANTEX1334HV0LV0.

6. Measurement of FGF-8 Binding Activity of Anti-FGF-8 Neutralizing CDR-Grafted Antibodies by ELISA The FGF-8 binding activity of the various anti-FGF-8 neutralizing CDR-grafted antibodies obtained in 4. of Reference Example 2 was measured by ELISA described in 2. (6) of Reference Example 1. The YB2/0 cell-derived anti-FGF-8 neutralizing chimeric antibody KM3334 obtained in 3. (2) of Reference Example 1 was used as a positive control. The results were shown in FIG. 24. As shown in FIG. 24, each of the anti-FGF-8 CDR-grafted antibodies showed an FGF-8 binding activity similar to that of KM3334, so that significant reduction of the binding activity caused by the CDR grafting was not observed.

7. Measurement of FGF-8 Binding Activity of Anti-FGF-8 Neutralizing CDR-Grafted Antibodies In order to examine the FGF-8 binding activity of the various anti-FGF-8 neutralizing CDR-grafted antibodies obtained in 4. of Reference Example 2 in more detail, the FGF-8 binding activity of the various anti-FGF-8 neutralizing CDR-grafted antibodies was measured and compared in the following manner using BIAcore2000 (manufactured by BIACORE). The YB2/0 cell-derived anti-FGF-8 neutralizing chimeric antibody KM3334 obtained in 3.(2) of Reference Example 1 was used as a positive control.

HBS-EP (manufactured by BIACORE) was used hereinafter as a sample diluent and a buffer during measurement. First, Sensor Chip CM5 (manufactured by BIACORE) was installed, and FGF-8 (manufactured by R & D) dissolved in 31.25 μg/mL of 10 mmol/L acetate buffer solution (pH 4.0) was immobilized on the surface of the sensor chip by the amine coupling method. The immobilization amount measured by using a resonance signal (RU) as an index was 4498 RU.

Figure 25:
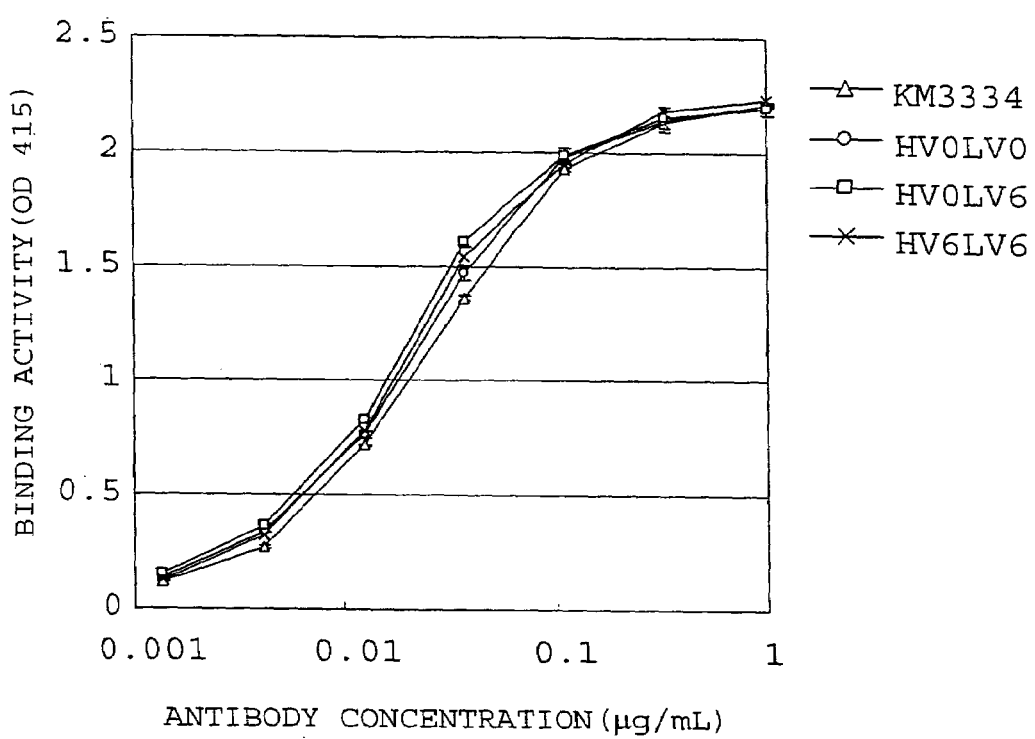
FIG. 25 is a graph showing the results of measuring FGF-8 binding activity of anti-FGF-8 neutralizing chimeric antibody KM3334 and anti-FGF-8 neutralizing CDR-grafted antibodies HV0LV0, HV0LV6 and HV6LV6 by ELISA. The abscissa represents an antibody concentration (μg/mL), and the ordinate represents the binding activity ($OD_{415}$). Δ indicates activity of KM3334, ○ activity of HV0LV0, Δ activity of HV0LV6, and × activity of HV6LV6.

60 μL of each of the antibody solutions was added to an FGF-8 immobilized flow cell at a flow rate of 20 μL/min, and the dissociation reaction was then monitored for 3 minutes. After the dissociation reaction, 20 μL of a 10 mmol/L glycine-hydrochloride solution (pH 1.5) was added to the flow cell twice continuously to regenerate the surface of the chip. This cycle was performed with the antibody solution at various concentrations (from 50 to 0.068 μg/mL) to obtain sensor grams at various concentrations. The sensor grams of the respective antibodies were converted to sensor grams of specific reactions by deducing a sensor gram obtained using chimeric antibody KM871 (Shitara K. et al., Cancer Immunol. Immunother., 36, 373-380, 1993) to GD3 as a negative control. The sensor grams of the various antibodies at a concentration of 50 μg/mL were shown in FIG. 25. As is apparent from the sensor grams, almost no dissociation was observed in any of the antibodies at the time of the dissociation reaction, and an exact dissociation rate constant was hardly obtained. Accordingly, the binding activity of the various antibodies was compared in terms of the binding [resonance signal (RU)] in the binding reaction. Consequently, as shown in FIG. 25, the chimeric antibody KM3334 showed the highest binding reaction, and the CDR-grafted antibody HV0LV6 showed the same high binding reaction as KM3334. Meanwhile, the CDR-grafted antibodies HV0LV0 and HV6LV6 showed the binding reaction which was slightly low in comparison to KM3334 and HV0LV6. These results reveal that the comparison in binding activity between the antibodies which was impossible by ELISA is possible by using BIAcore 2000 and the binding activity of the CDR-grafted antibodies is restored to the same level as that of the chimeric antibody by the replacement of the 6 amino acid residues of FR of VL. The effect of restoring the binding activity was not observed in the 6 amino acid residues of FR of VH.

The YB2/0 cell-derived CDR-grafted antibody HV0LV6 which showed the same high binding reaction as the chimeric antibody KM3334 was designated KM8037, and the YB2/0 cell-derived transformed cell line highly expressing KM8037 was also designated KM8037. The transformant KM8037 was deposited as FERM BP-8084 in International Patent Organism Depositary, National Institute of Advanced Industrial Science and Technology (AIST Tsukuba Central 6, 1-1-1 Higashi, Tsukubashi Ibaraki, 305-8566, Japan) on Jun. 20, 2002.

REFERENCE EXAMPLE 3

Production of Anti-FGF-8 Neutralizing CDR-grafted Antibodies Having Lower Immunogenicity The results of Reference Example 2 revealed that the anti-FGF-8 neutralizing CDR-grafted antibody HV0LV6 in which FR of VL underwent the modification of 6 amino acid residues derived from the mouse antibody KM1334 exhibited the same binding activity as the chimeric antibody. Therefore, upon studying the effect of 6 residues on the recovery of the activity, the production of anti-FGF-8 neutralizing CDR-grafted antibodies having satisfactory activity, comprising less amino acid residues derived from the mouse antibody and expected to more decrease the antigenicity was carried out in the following manner.

1. Designing of Amino Acid Sequences of VLs

With respect to the above 6 amino acid residues, the amino acid sequences of six types of VL having the following modifications were designed. All of them showed modifications from the amino acid residues of LV.0.

In LV.4-1, 4 residues of Ile at position 2, Gln at position 50, Leu at position 51 and Tyr at position 92 were changed to Val, Lys, Val and Phe, respectively, which are amino acid residues found in the mouse antibody KM1334.

In LV.4-2, 4 residues of Ile at position 2, Thr at position 14, Pro at position 15 and Tyr at position 92 were changed to Val, Ser, Leu and Phe, respectively, which are amino acid residues found in the mouse antibody KM1334.

In LV.3-1, 3 residues of Ile at position 2, Leu at position 51 and Tyr at position 92 were changed to Val, Val and Phe, respectively, which are amino acid residues found in the mouse antibody KM1334.

In LV.3-2, 3 residues of Thr at position 14, Pro at position 15 and Tyr at position 92 were changed to Ser, Leu and Phe, respectively, which are amino acid residues found in the mouse antibody KM1334.

In LV.2-1, 2 residues of Leu at position 51 and Tyr at position 92 were changed to Val and Phe, respectively, which are amino acid residues found in the mouse antibody KM1334.

In LV.2-2, 2 residues of Ile at position 2 and Tyr at position 92 were respectively changed to Val and Phe, respectively, which are amino acid residues found in the mouse antibody KM1334.

The amino acid sequences of LV.4-1, LV.4-2, LV.3-1, LV.3-2, LV.2-1 and LV.2-2 were described in SEQ ID NOS. 42 to 47 respectively.

2. Construction of DNAs Encoding VLs

DNAs encoding the amino acid sequences of various VLs of the anti-FGF-8 neutralizing CDR-grafted antibodies as designed in 1. of Reference Example 3 were constructed as follows.

(1) Construction of a DNA Encoding LV.4-1

The DNA encoding LV.4-1 was constructed by the method described in 1. (3) of Reference Example 2 using four synthetic DNAs (manufactured by GENSET) comprising SEQ ID NOS. 38, 34, 40 and 41 respectively. Consequently, the plasmid pKM1334LV4-1 comprising the DNA encoding LV.4-1 was obtained.

(2) Construction of a DNA Encoding LV.3-1

Using 50 ng of the plasmid pKM1334LV6 obtained in 1. (3) of Reference Example 2 was used as a template, M13 primer RV and the synthetic DNA having the nucleotide sequence describe in SEQ ID NO:48 (manufactured by GENSET) were added as primers to give a final concentration of 0.3 μmol/Lol/L, and PCR was carried out in a total volume of 50 μL by first heating at 94° C. for 2 minutes and subsequent 35 cycles of reactions at 94° C. for 15 seconds, 50° C. for 30 seconds and 68° C. for 1 minute as one cycle according to the manual attached to KOD Polymerase. The reaction solution was purified, and then dissolved in sterile water. The reaction was performed at 37° C. for 1 hour using 10 units of restriction endonuclease KpnI (manufactured by Takara Shuzo) and 10 units of restriction endonuclease SpeI. The reaction solution was fractionated by agarose gel electrophoresis to recover approximately 0.3 μg of a KpnI-SpeI fragment of approximately 0.22 kb.

Subsequently, 3 μg of the plasmid pKM1334LV4-1 obtained in 2. (1) of Reference Example 3 was reacted with 10 units of restriction endonuclease KpnI at 37° C. for 1 hour. The reaction solution was fractionated by agarose gel electrophoresis to recover approximately 0.2 μg of a KpnI fragment of approximately 0.21 kb.

Further, 3 μg of the plasmid pBluescript II SK(−) was reacted with 10 units of restriction endonuclease KpnI and 10 units of restriction endonuclease SpeI at 37° C. for 1 hour. The reaction solution was fractionated by agarose gel electrophoresis to recover approximately 2 μg of a KpnI-SpeI fragment of approximately 2.95 kb.

Figure 26:
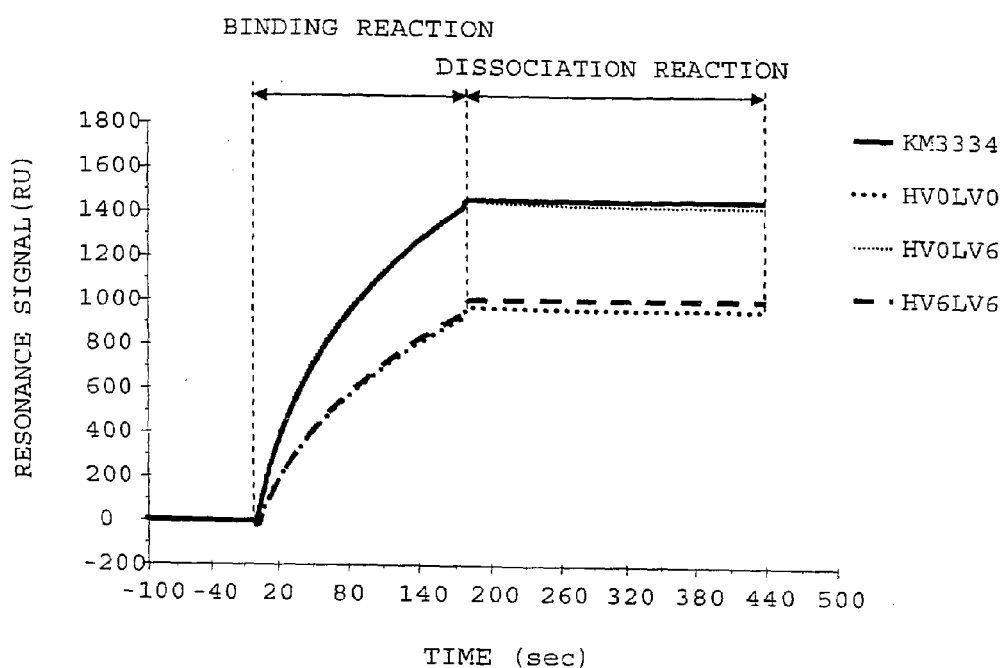
FIG. 26 is a graph showing the results of measuring FGF-8 binding activity of anti-FGF-8 neutralizing chimeric antibody KM3334 and anti-FGF-8 neutralizing CDR-grafted antibodies HV0LV0, HV0LV6 and HV6LV6 by BIAcore 2000. The abscissa represents time (sec), and the ordinate represents a resonance signal (RU).

0.1 μg of the KpnI-SpeI fragment of VL DNA, 0.1 μg of the KpnI fragment derived from the plasmid pKM1334LV4-1 and 0.1 μg of the KpnI-SpeI fragment derived from the plasmid pBluescript II SK(−) as obtained above were added to sterile water in a total amount of 10 μL, and ligated using Ligation High. *Escherichia coli* DH5α strain was transformed using the thus-obtained recombinant plasmid DNA solution to obtain plasmid pKM1334LV3-1 comprising the DNA encoding LV.3-1 as shown in FIG. 26.

(3) Construction of a DNA Encoding LV.2-1

Plasmid pKM1334LV2-1 comprising the DNA encoding LV.2-1 was obtained by the similar method described in 2. (1) of Reference Example 3 except that the plasmid pKM1334LV0 obtained in 1. (3) of Reference Example 2 was used instead of the plasmid pKM1334LV4-1.

(4) Construction of a DNA Encoding LV.2-2

Plasmid pKM1334LV2-2 comprising the DNA encoding LV.2-2 was obtained by the similar method described in 2. (1) of Reference Example 3 except that the synthetic DNA described in SEQ ID NO. 49 was used instead of the synthetic DNA described in SEQ ID NO. 48 as a primer.

(5) Construction of a DNA Encoding LV.4-2

3 μg of the plasmid pKM1334LV2-2 obtained in 2. (4) of Reference Example 3 was reacted with 10 units of restriction endonuclease KpnI at 37° C. for 1 hour. The reaction solution was fractionated by agarose gel electrophoresis to recover approximately 2 μg of a KpnI fragment of approximately 3.16 kb.

Subsequently, 3 μg of the plasmid pKM1334LV6 obtained in 1. (3) of Reference Example 2 was reacted with 10 units of restriction endonuclease KpnI at 37° C. for 1 hour. The reaction solution was fractionated by agarose gel electrophoresis to recover approximately 0.2 μg of a KpnI fragment of approximately 0.21 kb.

Figure 27:
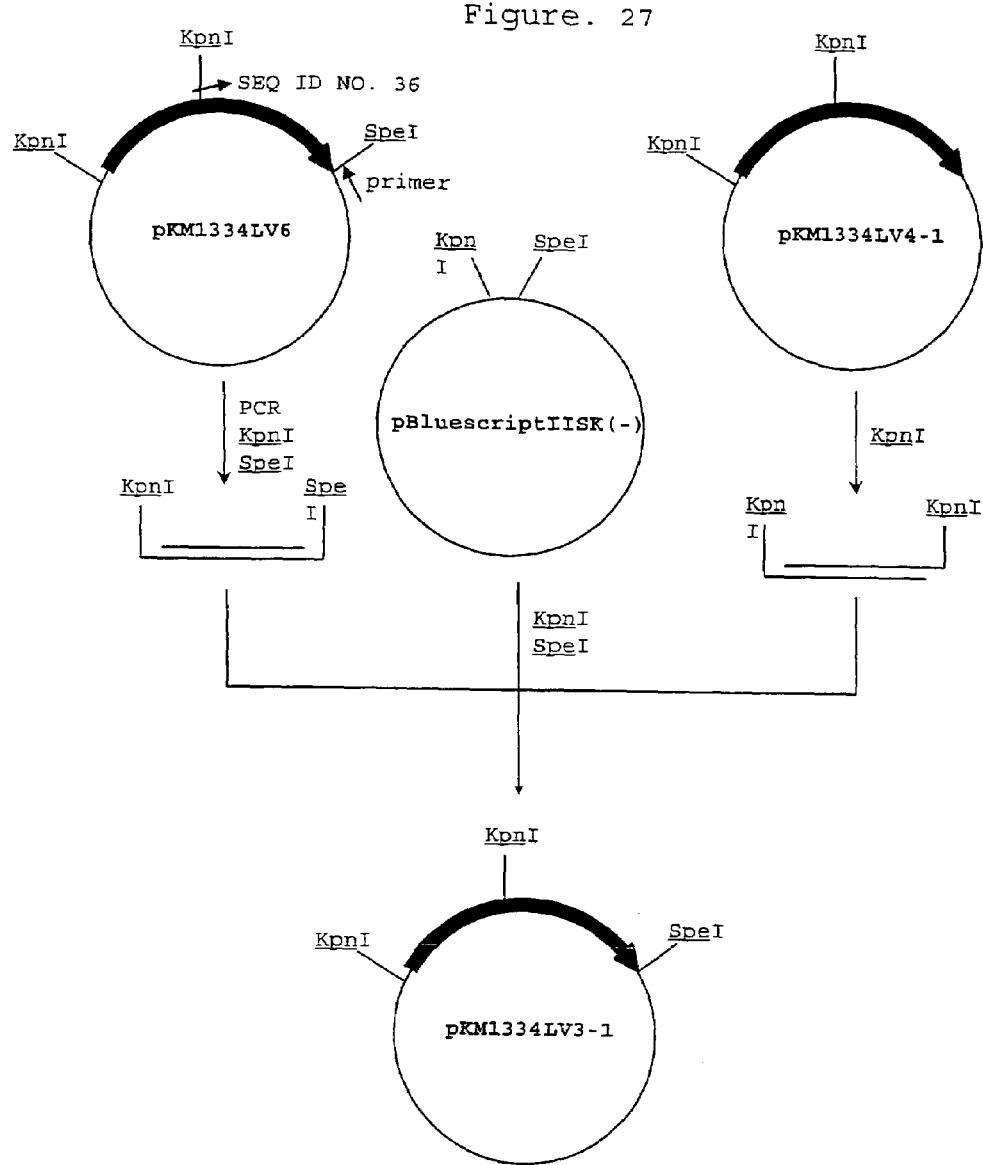
FIG. 27 is a flow chart showing construction of plasmid pKM1334LV3-1.

0.1 μg of the KpnI fragment derived from the plasmid pKM1334LV2-2 and 0.1 μg of the KpnI fragment derived from the plasmid pKM1334LV6 as obtained above were added to sterile water in a total amount of 10 μl, and ligated using Ligation High. *Escherichia coli* DH5α strain was transformed using the thus-obtained recombinant plasmid DNA solution to obtain plasmid pKM1334LV4-2 comprising the DNA encoding LV.4-2 as shown in FIG. 27.

(6) Construction of a DNA Encoding LV.3-2

3 μg of the plasmid pKM1334LV4-2 obtained in 2. (5) of Reference Example 3 was reacted with 10 units of restriction endonuclease Tth111I (manufactured by Takara Shuzo) and XmnI (manufactured by New England Biolabs) at 37° C. for 1 hour. The reaction solution was fractionated by agarose gel electrophoresis to recover approximately 2 μg of a Tth111I-XmnI fragment of approximately 2.24 kb.

Subsequently, 3 μg of the plasmid pKM1334LV0 obtained in 1. (3) of Reference Example 2 was reacted with 10 units of restriction endonuclease Tth111I and 10 units of restriction endonuclease XmnI at 37° C. for 1 hour. The reaction solution was fractionated by agarose gel electrophoresis to recover approximately 1 μg of a Tth111I-XmnI fragment of approximately 1.11 kb.

Figure 28:
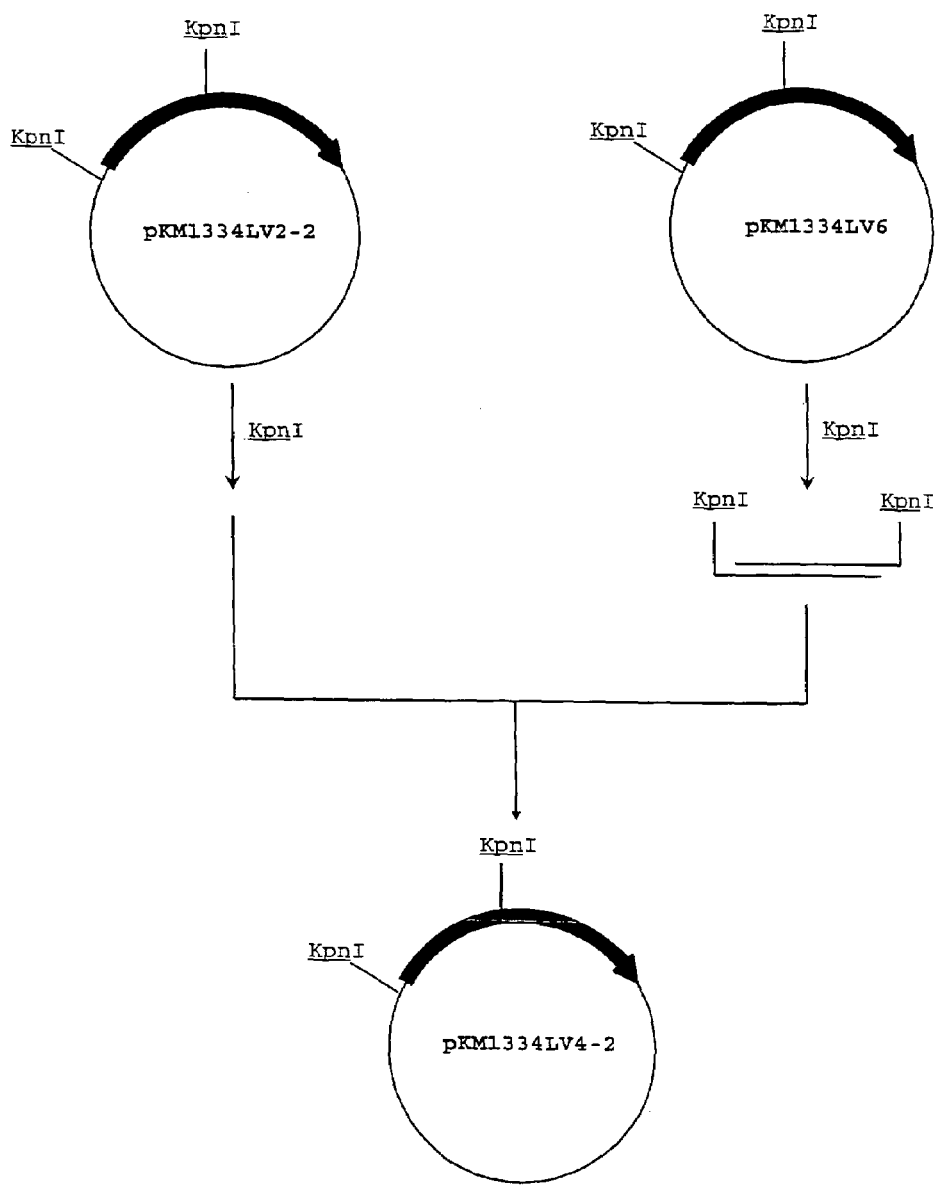
FIG. 28 is a flow chart showing construction of plasmid pKM1334LV4-2.

0.1 μg of the Tth111I-XmnI fragment derived from the plasmid pKM1334LV4-2 and 0.1 μg of the Tth111I-XmnI fragment derived from the plasmid pKM1334LV0 as obtained above were added to sterile water in a total amount of 10 μl, and ligated using Ligation High. *Escherichia coli* DH5α strain was transformed using the thus-obtained recombinant plasmid DNA solution to obtain plasmid pKM1334LV3-2 comprising the DNA encoding LV.3-2 as shown in FIG. 28.

3. Construction of Anti-FGF-8 Neutralizing CDR-Grafted Antibody Expression Vectors The EcoRI-BsiWI fragment comprising the DNA encoding VL of the expression vector pKANTEX1334HV0LV6 as obtained in 2. of Reference Example 2 was replaced with the EcoRI-BsiWI fragments comprising the DNAs encoding various VLs constructed in 2. of Reference Example 3 to construct anti-FGF-8 neutralizing CDR-grafted antibody expression vectors having the DNAs encoding various VLs. Specifically, six types, pKANTEX1334HV0LV4-1, pKANTEX1334HV0LV4-2, pKANTEX1334HV0LV3-1, pKANTEX1334HV0LV3-2, pKANTEX1334HV0LV2-1 and pKANTEX1334HV0LV2-2 were constructed.

4. Stable Expression of Anti-FGF-8 Neutralizing CDR-Grafted Antibodies Using CHO/DG44 Cells The stable expression of the various anti-FGF-8 neutralizing CDR-grafted antibodies in CHO/DG44 cells was performed by the method described in 2. (4) of Reference Example 1 using the anti-FGF-8 neutralizing CDR-grafted antibody expression vectors pKANTEx1334HV0LV0 and pKANTEX1334HV0LV6 obtained in 2. of Reference Example 2 and the anti-FGF-8 neutralizing CDR-grafted antibody expression vectors obtained in 3. of Reference Example 3.

5. Purification of Anti-FGF-8 Neutralizing CDR-Grafted Antibodies

The culturing of the CHO/DG44 cell-derived transformant expressing the various anti-FGF-8 neutralizing CDR-grafted antibodies obtained in 4. of Reference Example 3 and the purification of the anti-FGF-8 neutralizing CDR-grafted antibodies from the supernatant were performed by the method described in 3. (1) of Reference Example 1.

The antibody derived from the transformants which was introduced pKANTEX1334HV0LV0 was designated HV0LV0/CHO, the antibody derived from the transformants which was introduced pKANTEX1334HV0LV6 was designated HV0LV6/CHO, the antibody derived from the transformants which was introduced pKANTEX1334HV0LV4-1 was designated HV0LV4-1/CHO, the antibody derived from the transformants which was introduced pKANTEX1334HV0LV4-2 was designated HV0LV4-2/CHO, the antibody derived from the transformants which was introduced pKANTEX1334HV0LV3-1 was designated HV0LV3-1/CHO, the antibody derived from the transformants which was introduced pKANTEX1334HV0LV3-2 was designated HV0LV3-2/CHO, the antibody derived from the transformants which was introduced pKANTEX1334HV0LV2-1 was designated HV0LV2-1/CHO, and the antibody derived from the transformants which was introduced pKANTEX1334HV0LV2-2 was designated HV0LV2-2/CHO.

6. Analysis of Purified Anti-FGF-8 Neutralizing CDR-Grafted Antibodies

SDS-PAGE of the anti-FGF-8 neutralizing CDR-grafted antibodies obtained in 5. of Reference Example 3 was performed by the above method described in 4. of Reference Example 1. As a result, all of the antibodies were confirmed to be expressed as antibody molecules of the correct structures, and purified.

7. Measurement of FGF-8 Binding Activity of Anti-FGF-8 Neutralizing CDR-Grafted Antibodies by BIAcore Biosensor.

In order to examine the FGF-8 binding activity of the anti-FGF-8 neutralizing CDR-grafted antibodies obtained in 5. of Reference Example 3, the FGF-8 binding activity of the various anti-FGF-8 neutralizing CDR-grafted antibodies was measured and compared through BIAcore 2000 using compound 1 as a partial peptide of FGF-8 with the C terminal labeled with biotin in the following manner. The anti-FGF-8 neutralizing chimeric antibody KM3034 derived from CHO/DG44 cells obtained in 3. (1) of Reference Example 1 was used as a positive control.

HBS-EP was used as a sample diluent and a buffer during measurement. First, Sensor Chip SA (manufactured by BIACORE) was installed, and 5 μL of compound 1 labeled with biotin which had been adjusted to 0.05 μg/mL was added at a flow rate of 5 μL/min. Then, 5 μL of a 10 mmol/L glycine-hydrochloride solution (pH 1.5) was added twice continuously to wash the tip surface. The immobilization amount of the FGF-8 peptide was 35 RU.

60 μL of each of the antibody solutions was added to an FGF-8 peptide immobilized flow cell at a flow rate of 20 μL/min, and the dissociation reaction was then monitored for 3 minutes. After the dissociation reaction, 20 μL of 10 mmol/L glycine-hydrochloride solution (pH 1.5) was added twice continuously to regenerate the chip surface. This cycle was performed on the antibody solution at various concentrations (from 50 to 1.85 μg/mL) to obtain sensor grams at various concentrations. The sensor grams of the respective antibodies were converted to sensor grams of specific reactions by deduceing a sensor gram obtained using the chimeric antibody KM871 to GD3 as a negative control.

Figure 29:
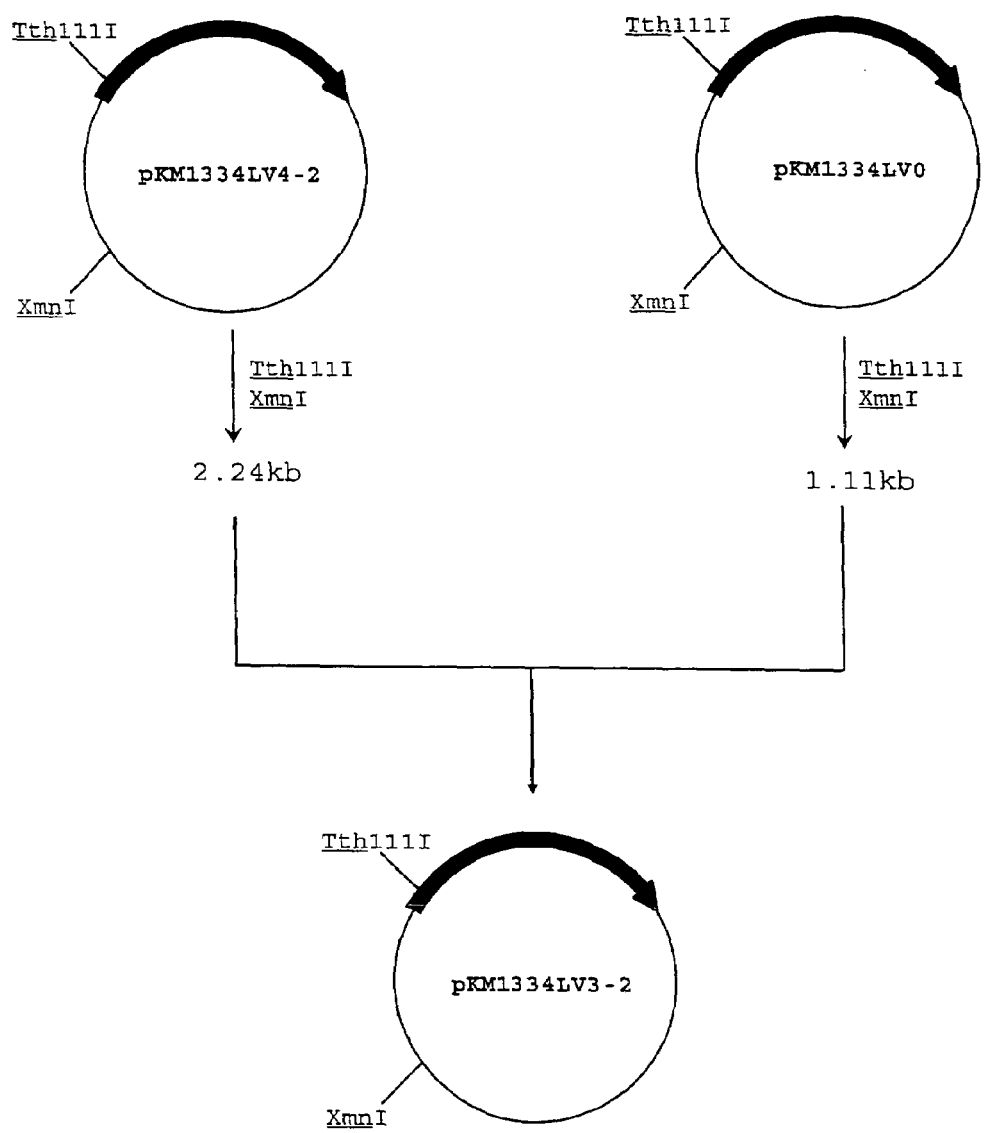
FIG. 29 is a flow chart showing construction of plasmid pKM1334LV3-2.

The sensor grams of the various antibodies at a concentration of 16.7 μg/mL were shown in FIG. 29. As is apparent from the sensorgram, dissociation was hardly observed at the time of the dissociation reaction of each antibody, so that it was difficult to obtain accurate dissociation constant. Accordingly, the binding activity of various antibodies was carried out by comparing intensity of binding [resonance signal (RU)] at the time of the binding reaction.

Consequently, as shown in FIG. 29, the chimeric antibodies KM3034 and the HV0LV6/CHO showed the highest binding reaction, and the HV0LV3-1/CHO, the HV0LV4-1/CHO and the HV0LV2-1/CHO showed the higher binding reaction. Meanwhile, the HV0LV3-2/CHO, the HV0LV2-2/CHO and the HV0LV4-2 showed the lower binding reaction, and the HV0LV0/CHO showed the lowest binding reaction. These results were consistent with the results obtained by using the YB2/0 cell-derived anti-FGF-8 neutralizing CDR-grafted antibodies described in 7. of Reference Example 2.

Figure 30:
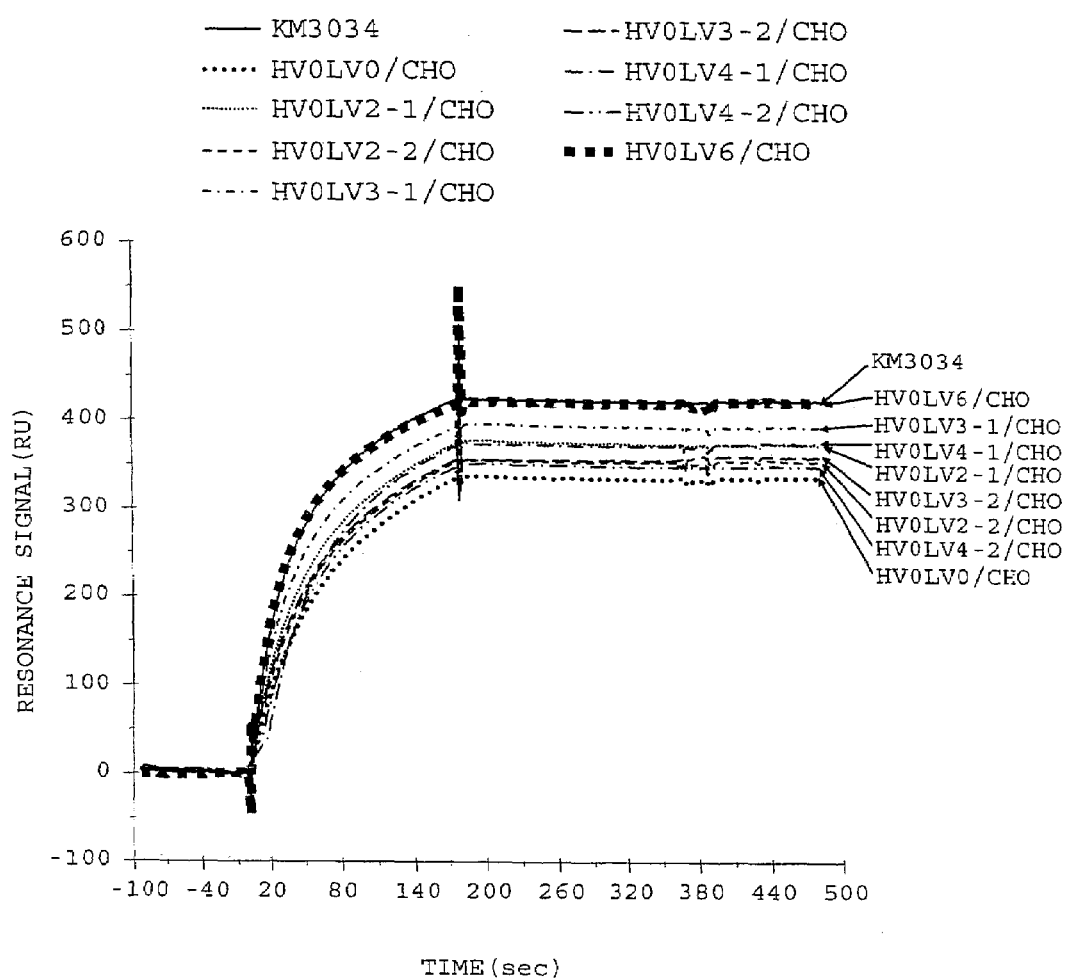
FIG. 30 is a graph showing the results of measuring FGF-8 binding activity of anti-FGF-8 neutralizing chimeric antibody KM3034 and anti-FGF-8 neutralizing CDR-grafted antibodies HV0LV0/CHO, HV0LV6/CHO, HV0LV4-1/CHO, HV0LV4-2/CHO, HV0LV3-1/CHO, HV0LV3-2/CHO, HV0LV2-1/CHO and HV0LV2-2/CHO by BIAcore 2000. The abscissa represents time (sec), and the ordinate represents a resonance signal (RU).

8. Measurement of Neutralizing Activity to FGF-8 of Anti-FGF-8 Neutralizing CDR-Grafted Antibodies Regarding the four anti-FGF-8 neutralizing CDR-grafted antibodies, the HV0HV0LV6/CHO, the HV0LV3-1/CHO, the HV0LV4-1/CHO and the HV0LV2-1/CHO in which the high binding reaction to FGf-8 was confirmed in 7. of Reference Example 3, the FGF-8 neutralizing activity was evaluated by the method described in 5. of Reference Example 2. The anti-FGF-8 neutralizing chimeric antibody KM3034 derived from CHO/DG44 cells obtained in 3. (1) of Reference Example 1 was used as a positive control, and the chimeric antibody KM2760 to human chemokine CCR4 described in WO 01/64754 was used as a negative control. The results are shown in FIG. 30. As shown in FIG. 30, the HV0LV6/CHO showed similar FGF-8 neutralizing activity to that of the chimeric antibody KM3034, and the HV0LV3-1/CHO showed the next high FGF-8 neutralizing activity. The HV0LV4-1/CHO showed the slightly lower FGF-8 neutralizing activity than the HV0LV3-1/CHO, and the HV0LV2-1/CHO showed the lowest neutralizing activity. Correlation was found between the intensity of the FGF-8 neutralizing activity and the intensity of the binding reaction measured by BIAcore.

REFERENCE EXAMPLE 4

Preparation of Anti-FGF-8 Neutralizing CDR-Grafted Antibodies Having Lower Antigenicity (2)

The results in Reference Example 3 revealed that among the modification of the 6 amino acid residues of LV6, the modification at poition 51 was essential for recovering the activity. With respect to the modification at position 2, it was suggested that the single modification contributed to cooperatively recovering the activity in combination with the modification at poition 51, though the effect on the recovery of the activity was small. The modification at position 14 and 15 were also suggested to contribute to cooperatively recovering the activity in combination with the modification at position 51. Meanwhile, the effect of the modification at position 50 was suggested to be low. Accordingly, for examining which of the modification at position 2, the modification at position 14 15 was more effective for recovery of the activity and for examining the effect of the modification at position 92, the production of anti-FGF-8 neutralizing CDR-grafted antibodies was reexamined.

1. Re-Designing of Amino Acid Sequences of VLs

Amino acid sequences of two VLs having the following modifications were designed. Each case shows modification from amino acid residues of LV.0.

In LV.4-3, 4 residues of Thr at position 14, Pro at position 15, Leu at position 51 and Tyr at position 92 were changed to Ser, Leu, Val and Phe, respectively, which are amino acid residues found in the mouse antibody KM1334.

In LV.3-3, 3 residues of Thr at position 14, Pro at position 15 and Leu at position 51 were changed to Ser, Leu and Val, respectively, which are amino acid residues found in the mouse antibody KM1334.

The amino acid sequence of LV.4-3 was described in SEQ ID NO. 50, and the amino acid sequence of LV.3-3 in SEQ ID NO. 51 respectively.

2. Construction of DNAs Encoding VLs

DNAs encoding the amino acid residues of various VLs of the anti-FGF-8 neutralizing CDR-grafted antibodies designed in 1. of Reference Example 4 were constructed as follows.

(1) Construction of a DNA Encoding LV.4-3

The DNA was constructed by the method described in 2. (5) of Reference Example 3 except that the plasmid pKM1334LV2-1 obtained in 2. (3) of Reference Example 3 was used instead of the plasmid pKM1334LV2-2 and the plasmid pKM1334LV3-2 obtained in 2. (6) of Reference Example 3 instead of the plasmid pKM1334LV6. As a result, the plasmid pKM1334LV4-3 comprising the DNA encoding LV.4-3 was obtained.

(2) Construction of a DNA Encoding LV.3-3

3 μg of the plasmid pKM1334LV4-3 obtained in 2. (1) of Reference Example 4 was reacted with 10 units of restriction endonuclease BamHI (manufactured by Takara Shuzo) and 10 units of restriction endonuclease SpeI at 37° C. for 1 hour. The reaction solution was fractionated by agarose gel electrophoresis to recover approximately 2.5 μg of a BamHI-SpeI fragment of approximately 3.23 kb.

Subsequently, 3 μg of the plasmid pKM1334LV0 obtained in 1. (3) of Reference Example 2 was reacted with 10 units of restriction endonuclease BamHI and 10 units of restriction endonuclease SepI at 37° C. for 1 hour. The reaction solution was fractionated by agarose gel electrophoresis to recover approximately 0.15 μg of a BamHI-SpeI fragment of approximately 0.13 kb.

Figure 31:
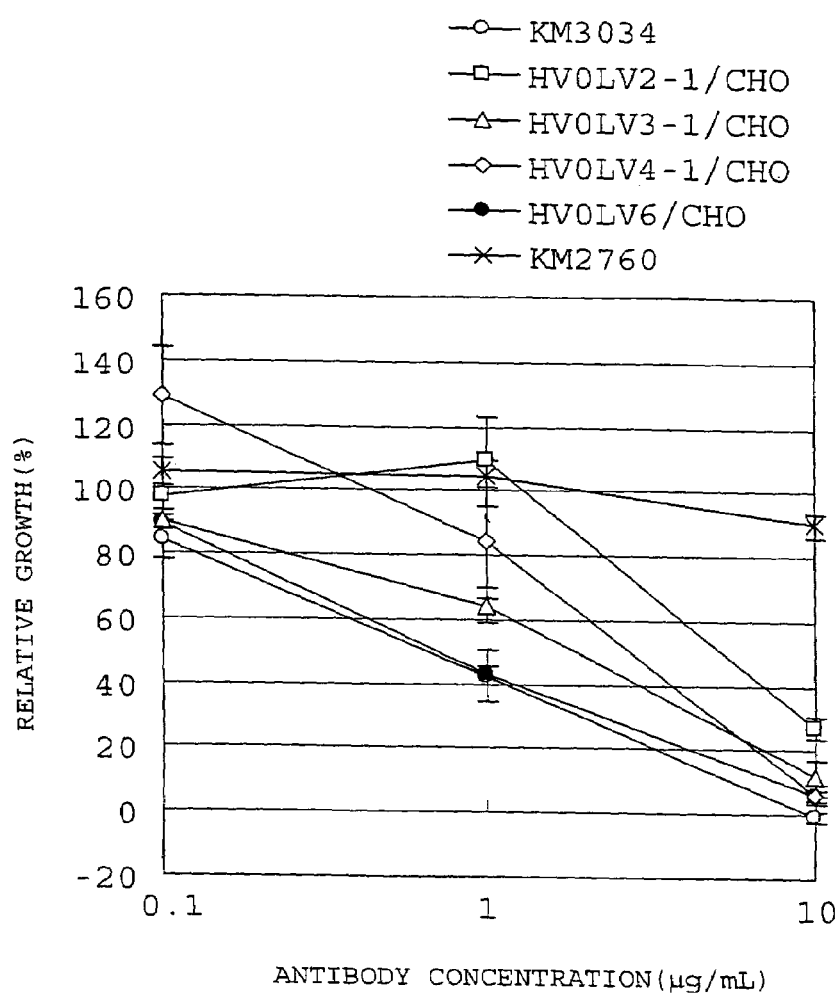
FIG. 31 is a graph showing neutralizing activity of anti-FGF-8 neutralizing chimeric antibody KM3034 and anti-FGF-8 neutralizing CDR-grafted antibodies HV0LV6/CHO, HV0LV4-1/CHO, HV0LV3-1/CHO and HV0LV2-1/CHO to FGF-8-dependent growth of mouse breast cancer cell line SC-3. The abscissa represents an antibody concentration (μg/mL), and the ordinate represents the relative growth (%) when the growth in the addition of FGF-8 alone is defined as 100%. ○ indicates activity of KM3034, ● activity of HV0LV6/CHO, ◇ HV0LV4-1/CHO, Δ activity of HV0LV3-1/CHO, □ activity of HV0LV2-1/CHO, and × activity of KM2760 as a negative control.

0.1 μg of the BamHI-SpeI fragment derived from the plasmid pKM1334LV4-3 and 0.1 μg of the BamHI-SpeI fragment derived from the plasmid pKM1334LV0 obtained above were added to sterile water in a total amount of 10 μl, and ligated using Ligation High. *Escherichia coli* DH5α strain was transformed using the thus-obtained recombinant plasmid DNA solution to obtain the plasmid pKM1334LV3-3 comprising the DNA encoding LV3-3 as shown in FIG. 31.

3. Construction of Anti-FGF-8 Neutralizing CDR-Grafted Antibody Expression Vectors The anti-FGF-8 neutralizing CDR-grafted antibody expression vectors having DNAs encoding various VLs were constructed by replacing the EcoRI-BsiWI fragment comprising the DNA encoding VL of the expression vector pKANTEX1334HV0LV6 obtained in 2. of Reference Example 2 with the EcoRI-BsiWI fragments comprising the DNAs encoding various VLs as constructed in 2. of Reference Example 4. Specifically, two types, pKANTEX1334HV0LV4-3 and pKANTEX1334HV0LV3-3 were constructed.

4. Stable Expression of Anti-FGF-8 Neutralizing CDR-Grafted Antibodies Using CHO/DG44 Cells The stable expression of the anti-FGF-8 neutralizing CDR-grafted antibodies in CHO/DG44 cells was performed by the method described in 2. (4) of Reference Example 1 using the anti-FGF-8 neutralizing CDR-grafted antibody expression vectors obtained in 3. of Reference Example 4.

5. Purification of Anti-FGF-8 Neutralizing CDR-Grafted Antibodies

The culturing of the CHO/DG44 cell-derived transformant expressing the various anti-FGF-8 neutralizing CDR-grafted antibodies as obtained in 4. of Reference Example 4 and the purification of the anti-FGF-8 neutralizing CDR-grafted antibodies from the supernatant were performed by the method described in 3. (1) of Reference Example 1. The antibody derived from the transformant with the pKANTEX1334HV0LV4-3 introduced was designated HV0LV4-3/CHO, and the antibody derived from the transformant with the pKANTEX1334HV0LV3-3 introduced was designated HV0LV3-3/CHO.

6. Analysis of Purified Anti-FGF-8 Neutralizing CDR-Grafted Antibodies

SDS-PAGE of the anti-FGF-8 neutralizing CDR-grafted antibodies obtained in 5. of Reference Example 4 was performed by the method described in 4. of Reference Example 1. As a result, it was confirmed that every antibodies were expressed as antibody molecules of the correct structures, and purified.

7. Measurement of FGF-8 Binding Activity of Anti-FGF-8 Neutralizing CDR-Grafted Antibodies The FGF-8 binding activity of the anti-FGF-8 neutralizing CDR-grafted antibodies HV0LV6/CHO and HV0LV3-1/CHO obtained in 5. of Reference Example 3 and the anti-FGF-8 neutralizing CDR-grafted antibodies HV0LV4-3/CHO and HV0LV3-3/CHO obtained in 5. of Reference Example 4 was measured by the method described in 7. of Reference Example 3. The CHO/DG44 cell-derived anti-FGF-8 neutralizing chimeric antibody KM3034 obtained in 3. (1) of Reference Example 1 was used as a positive control.

Figure 32:
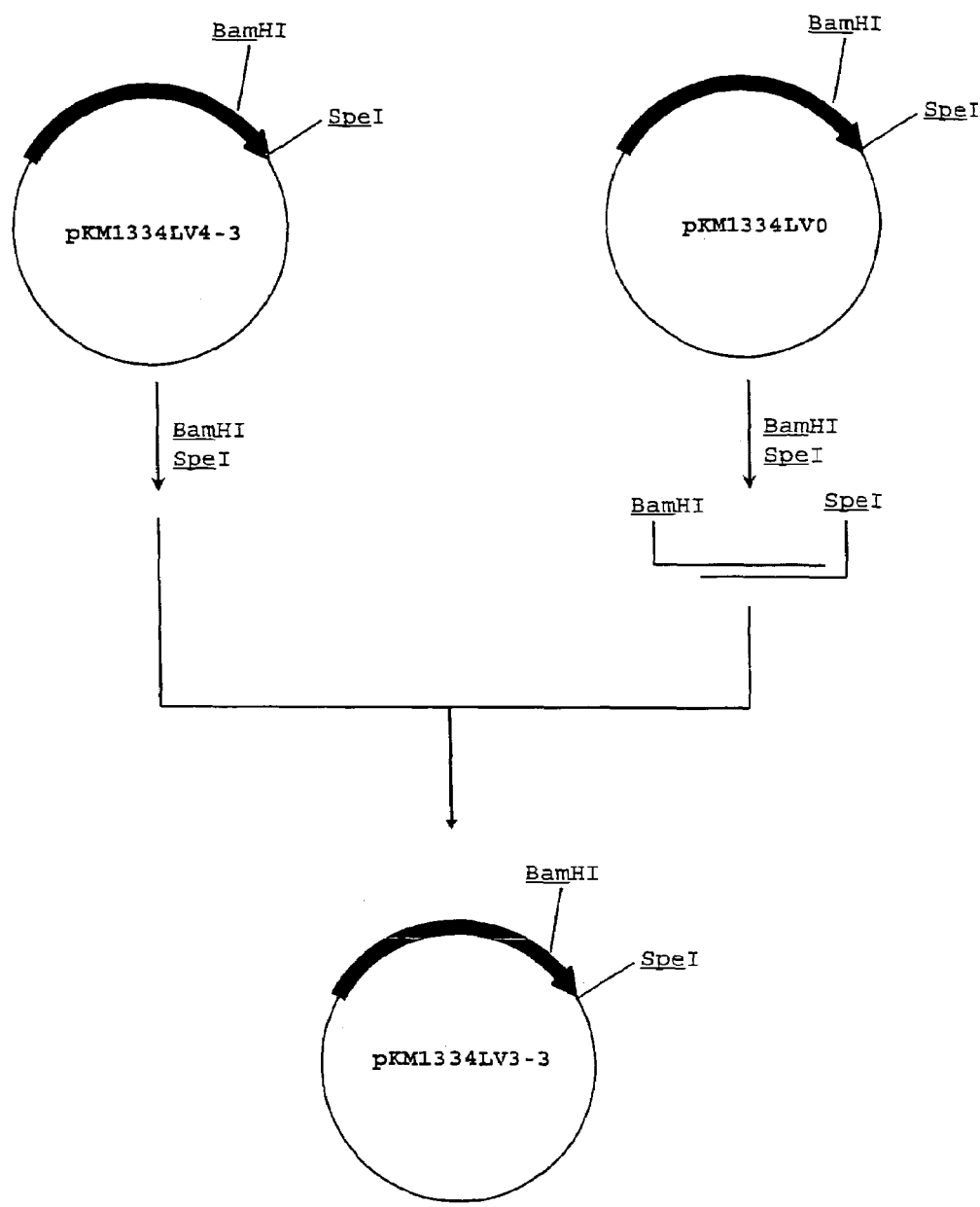
FIG. 32 is a flow chart showing construction of plasmid pKM1334LV3-3.

Sensor grams of the various antibodies at a concentration of 16.7 µg/mL were shown in FIG. 32. As is apparent from the sensor grams, dissociation was hardly observed at the time of the dissociation reaction of the antibodies, so that it was difficult to obtain accurate dissociation constant. Accordingly, the binding activity of the various antibodies was compared in terms of the binding [resonance signal (RU)] at the time of binding reaction. Consequently, as shown in FIG. 32, the chimeric antibody KM3034 showed the highest binding reaction, and the HV0LV4-3/CHO showed the higher binding reaction than that of the HV0LV3-1/CHO and similar to that of the HV0LV6/CHO. The binding reaction of the HV0LV3-3/CHO was lower than that of the HV0LV3-1. These results suggested that regarding the height of the binding reaction, the modifications at position of 14 and 15 functioned more cooperatively than the modifications at position of 2, and the modifications at position of 92 was essential for the recovery of the activity.

Figure 33:
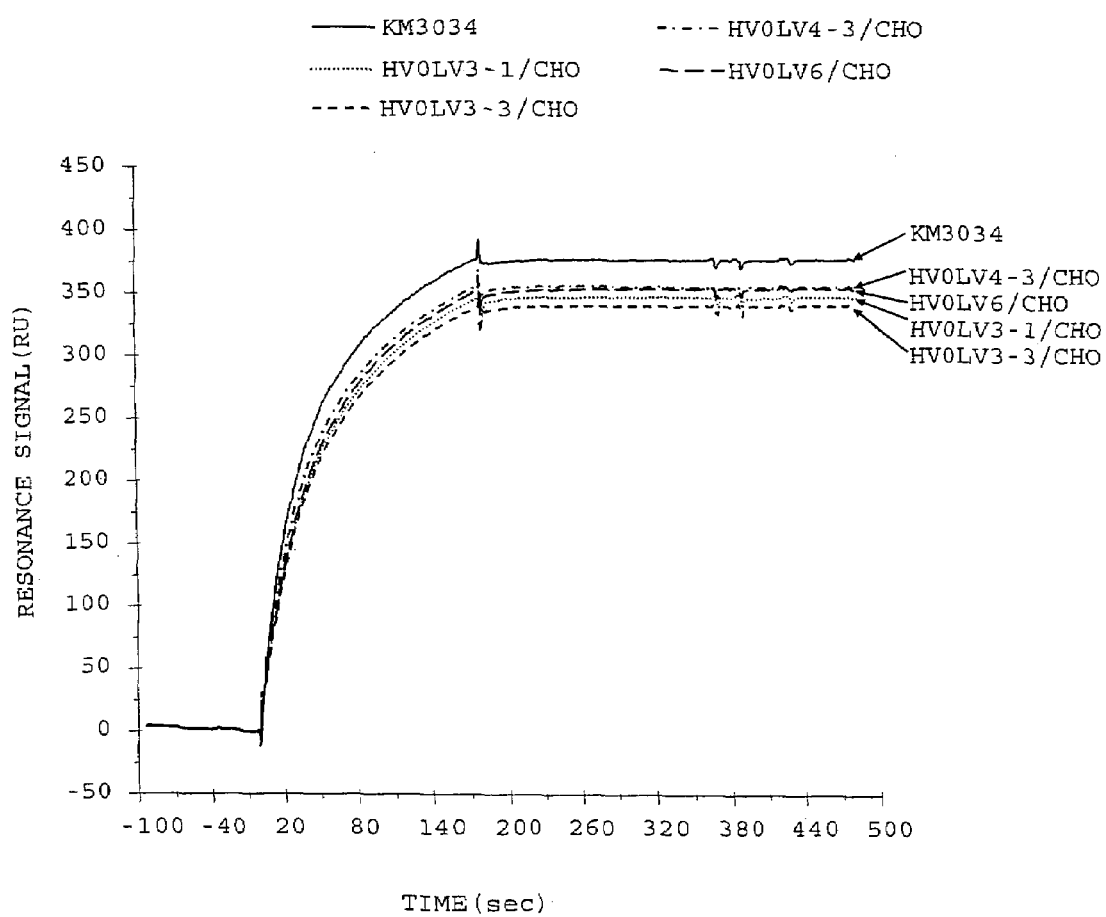
FIG. 33 is a graph showing the results of measuring FGF-8 binding activity of anti-FGF-8 neutralizing chimeric antibody KM3034 and anti-FGF-8 neutralizing CDR-grafted antibodies HV0LV6/CHO, HV0LV3-1/CHO, HV0LV4-3/CHO and HV0LV3-3/CHO by BIAcore 2000. The abscissa represents time (sec), and the ordinate represents a resonance signal (RU).
Figure 34:
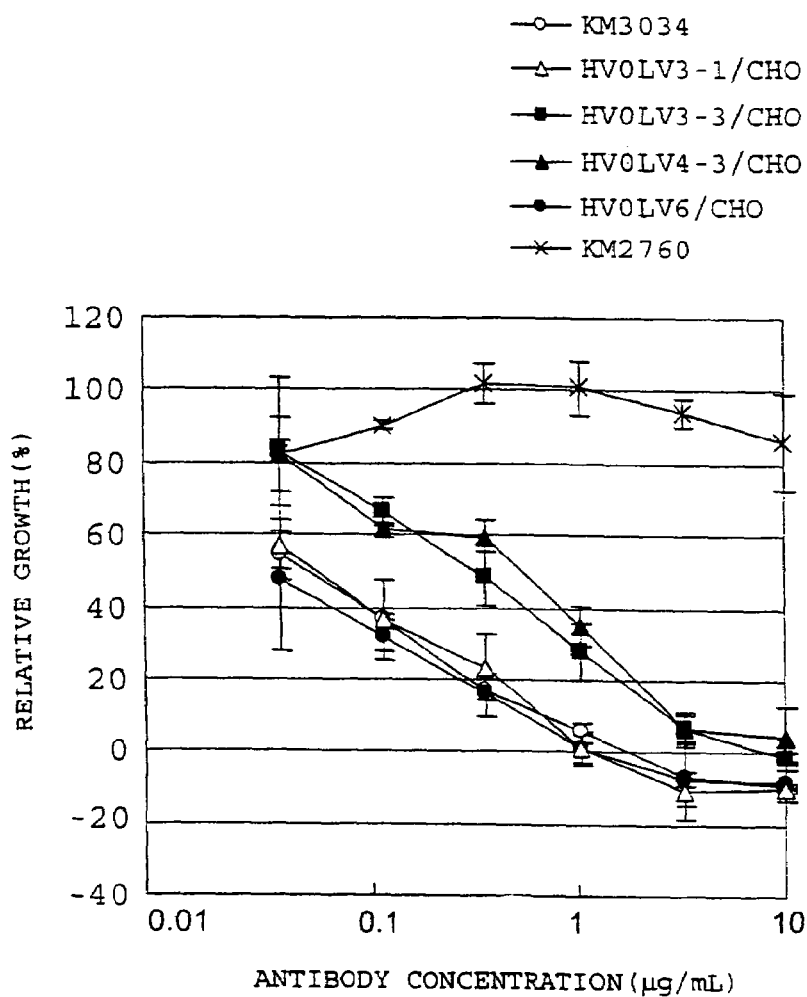
FIG. 34 is a graph showing neutralizing activity of anti-FGF-8 neutralizing chimeric antibody KM3034 and anti-FGF-8 neutralizing CDR-grafted antibodies HV0LV6/CHO, HV0LV3-1/CHO, HV0LV4-3/CHO and HV0LV3-3/CHO to FGF-8-dependent growth of mouse breast cancer cell line SC-3. The abscissa represents an antibody concentration (μg/mL), and the ordinate represents the relative growth (%) when the growth in the addition of FGF-8 alone is defined as 100%. ○ indicates activity of KM3034, ● activity of HV0LV6/CHO, Δ activity of HV0LV3-1/CHO, ▲ activity of HV0LV4-3/CHO, ■ activity of HV0LV3-3/CHO, and × activity of KM2760 as a negative control.

8. Measurement of Neutralizing Activity to FGF-8 of Anti-FGF-8 Neutralizing CDR-Grafted Antibodies The FGF-8 neutralizing activity of the anti-FGF-8 neutralizing CDR-grafted antibodies HV0LV6/CHO and HV0LV3-1/CHO obtained in 5. of Reference Example 3 and the anti-FGF-8 neutralizing CDR-grafted antibodies HV0LV4-3/CHO and HV0LV3-3/CHO obtained in 5. of Reference Example 4 was evaluated by the method described in 5. of Reference Example 2. The CHO/DG44 cell-derived-anti-FGF-8 neutralizing chimeric antibody KM3034 obtained in 3. (1) of Reference Example 1 was used as a positive control, and the chimeric antibody KM2760 to human chemokine CCR4 described in WO 01/64754 was used as a negative control. The results were shown in FIG. 33. As shown in FIG. 33, the HV0LV6/CHO and the HV0LV3-1/CHO showed the similar FGF-8 neutralizing activity as the chimeric antibody KM3034. Meanwhile, the HV0LV4-3/CHO and the HV0LV3-3/CHO showed the similar neutralizing activity which was approximately half that of the chimeric antibody KM3034. The neutralizing activity of the HV0LV3-1/CHO and the HV0LV4-3/CHO showed no correlation with the height of the binding reaction measured by BIAcore, and it was suggested that the amino acid residue at position 2 and the amino acid residues at position 14 and 15 gave the independent influences on the FGF-8 binding activity for FGF-8 and the FGF-8 neutralizing activity for cells.

In view of the foregoing various evaluation results, the CHO/DG44 cell-derived CDR-grafted antibody HV0LV6/CHO showing the high binding reaction and FGF-8 neutralizing activity similar to the chimeric antibody KM3034 was designated KM8034, and the CHO/DG44 cell-derived transformant highly expressing KM8034 was designated KM8034 in the same manner. The CHO/DG44 cell-derived CDR-grafted antibody HV0LV4-3/CHO showing the high binding reaction similar to that of KM8034 was designated KM8035, and the CHO/DG44 cell-derived transformant highly expressing KM8035 was designated KM8035 in the same manner. The VL amino acid sequence LV.4-3 of KM8035 was described in SEQ ID NO. 38. Furthermore, transformant KM8035 was deposited as FERM BP-8082 in International Patent Organism Depositary, National Institute of Advanced Industrial Science and Technology (AIST Tsukuba Central 6, 1-1-1 Higashi, Tsukubashi Ibaraki, 305-8566, Japan) on Jun. 20, 2002. The CHO/DG44 cell-derived CDR-grafted antibody HV0LV3-1/CHO showing the high FGF-8 neutralizing activity similar to that of KM8034 was designated KM8036, and the CHO/DG44 cell-derived transformant highly expressing KM8036 was designated KM8036 in the same manner. The VL amino acid sequence LV.3-1 of KM8036 was described in SEQ ID NO. 39. Transformant KM8036 was deposited as FERM BP-8083 in International Patent Organism Depositary, National Institute of Advanced Industrial Science and Technology (AIST Tsukuba Central 6, 1-1-1 Higashi, Tsukubashi Ibaraki, 305-8566, Japan) on Jun. 20, 2002.

The anti-FGF-8 neutralizing CDR-grafted antibody KM8034 showed the high binding reaction and FGF-8 neutralizing activity similar to those of the chimeric antibody KM3034, and the antigenicity in humans is reduced than the chimeric antibody. Thus, the higher therapeutic effect than that of the chimeric antibody is expected. The anti-FGF-8 neutralizing CDR-grafted antibodies KM8036 and KM8035 might be slightly lower than KM8034 in the binding activity and the FGF-8 neutralizing activity. However, since the amino acid residues of FR of the V region derived from mouse antibody KM1334 are 3 residues and 4 residues, the immunogenicity thereof is expected to be more decreased than that of KM8034.

INDUSTRIAL APPLICABILITY

The present invention provides an agent for preventing or treating arthritis, a cartilage protecting agent, a joint destruction inhibitor and a synovial membrane growth inhibitor comprising an anti-FGF-8 neutralizing antibody as an active ingredient, as well as a diagnostic agent of arthritis comprising an anti-FGF-8 antibody as an active ingredient and a method for judging arthritis using the antibody.

"Sequence Listing Free Text"

SEQ ID NO. 13—Primer for amplifying VH of KM1334
SEQ ID NO. 14—Primer for amplifying VH of KM1334
SEQ ID NO. 15—Primer for amplifying VL of KM1334
SEQ ID NO. 16—Primer for amplifying VH of KM1334
SEQ ID NO. 17—Peptide of human FGF-8 with a cysteine residue added to the C-terminal (23rd to 46th amino acid residues)
SEQ ID NO. 18—Amino acid sequence, HV.0 of VH of an anti-FGF-8 neutralizing CDR-grafted antibody designed
SEQ ID NO. 19—Amino acid sequence, LV.0 of VL of an anti-FGF-8 neutralizing CDR-grafted antibody designed
SEQ ID NO. 20—Amino acid sequence, HV.6 of VH of an anti-FGF-8 neutralizing CDR-grafted antibody designed
SEQ ID NO. 21—Amino acid sequence, LV.6 of VL of an anti-FGF-8 neutralizing CDR-grafted antibody designed
SEQ ID NO. 22—DNA encoding HV.0
SEQ ID NO. 23—Synthetic DNA for construction of DNA encoding HV.0
SEQ ID NO. 24—Synthetic DNA for construction of DNA encoding HV.0
SEQ ID NO. 25—Synthetic DNA for construction of DNA encoding HV.0
SEQ ID NO. 26—Synthetic DNA for construction of DNA encoding HV.0
SEQ ID NO. 27—DNA encoding HV.6
SEQ ID NO. 28—Synthetic DNA for construction of DNA encoding HV.6
SEQ ID NO. 29—Synthetic DNA for construction of DNA encoding HV.6
SEQ ID NO. 30—Synthetic DNA for construction of DNA encoding HV.6
SEQ ID NO. 31—Synthetic DNA for construction of DNA encoding HV.6
SEQ ID NO. 32—DNA encoding LV.0
SEQ ID NO. 33—Synthetic DNA for construction of DNA encoding LV.0
SEQ ID NO. 34—Synthetic DNA for construction of DNA encoding LV.0
SEQ ID NO. 35—Synthetic DNA for construction of DNA encoding LV.0
SEQ ID NO. 36—Synthetic DNA for construction of DNA encoding LV.0
SEQ ID NO. 37—DNA encoding LV.6
SEQ ID NO. 38—Synthetic DNA for construction of DNA encoding LV.6
SEQ ID NO. 39—Synthetic DNA for construction of DNA encoding LV.6
SEQ ID NO. 40—Synthetic DNA for construction of DNA encoding LV.6
SEQ ID NO. 41—Synthetic DNA for construction of DNA encoding LV.6
SEQ ID NO. 42—Amino acid sequence, LV.4-1 of VL of an anti-FGF-8 neutralizing CDR-grafted antibody designed
SEQ ID NO. 43—Amino acid sequence, LV.4-2 of VL of an anti-FGF-8 neutralizing CDR-grafted antibody designed
SEQ ID NO. 44—Amino acid sequence, LV.3-1 of VL of an anti-FGF-8 neutralizing CDR-grafted antibody designed
SEQ ID NO. 45—Amino acid sequence, LV.3-2 of VL of an anti-FGF-8 neutralizing CDR-grafted antibody designed
SEQ ID NO. 46—Amino acid sequence, LV.2-1 of VL of an anti-FGF-8 neutralizing CDR-grafted antibody designed
SEQ ID NO. 47—Amino acid sequence, LV.2-2 of VL of an anti-FGF-8 neutralizing CDR-grafted antibody designed
SEQ ID NO. 48—Primer for construction of DNA encoding LV.3-1
SEQ ID NO. 49—Primer for construction of DNA encoding LV.2-2
SEQ ID NO. 50—amino acid sequence, LV.4-3 of VL of an anti-FGF-8 neutralizing CDR-grafted antibody designed
SEQ ID NO. 51—amino acid sequence, LV.3-3 of VL of an anti-FGF-8 neutralizing CDR-grafted antibody designed

The invention claimed is:

1. A method of treating arthritis, comprising administering to a patient, as an active ingredient, an antibody which specifically binds to FGF-8 to inhibit activity of FGF-8,
   wherein the antibody is a monoclonal antibody selected from an antibody produced by a hybridoma, a humanized antibody and an antigen-binding fragment thereof,
   wherein the humanized antibody is a human chimeric antibody or a human complementarity determining region (CDR)-grafted antibody comprising CDRs of VH and VL of a monoclonal antibody which specifically binds to FGF-8 to inhibit activity of FGF-8 and CH and CL of a human antibody,
   wherein CDR1, CDR2 and CDR3 of VH comprise the amino acid sequences of SEQ ID NOS: 7, 8 and 9 respectively and CDR1, CDR2 and CDR3 of VL comprise the amino acid sequences of SEQ ID NOS: 10, 11 and 12 respectively.

2. A method of treating arthritis, comprising administering to a patient, as an active ingredient, an antibody which specifically binds to FGF-8 to inhibit activity of FGF-8,
   wherein the antibody is a monoclonal antibody selected from an antibody produced by a hybridoma, a humanized antibody and an antigen-binding fragment thereof,
   wherein the humanized antibody is a human chimeric antibody or a human complementarity determining region (CDR)-grafted antibody comprising CDRs of VH and VL of a monoclonal antibody which specifically binds to FGF-8 to inhibit activity of FGF-8 and CH and CL of a human antibody,
   wherein VH comprises the amino acid sequence of SEQ ID NO: 18 or 20 and VL comprises the amino acid sequence of SEQ ID NO: 19, 21, 42, 43, 44, 45, 46, 47, 50 or 51.

3. The method according to claim 2, wherein the human CDR-grafted antibody is any of the following human CDR-grafted antibodies (a) to (c),
   (a) a human CDR-grafted antibody in which VH comprises the amino acid sequence of SEQ ID NO: 18 and VL comprises the amino acid a sequence of SEQ ID NO: 21,
   (b) a human CDR-grafted antibody in which VH comprises the amino acid sequence of SEQ ID NO: 18 and VL comprises the amino acid sequence of SEQ ID NO: 44, and
   (c) a human CDR-grafted antibody in which VH comprises the amino acid sequence of SEQ ID NO: 18 and VL comprises an amino an the sequence of SEQ ID NO: 50.

4. A method of treating arthritis, comprising administering to a patient, as an active ingredient, an antibody which specifically binds to FGF-8 to inhibit activity of FGF-8,
   wherein the antibody is a monoclonal antibody selected from an antibody produced by a hybridoma, a humanized antibody and an antigen-binding fragment thereof,
   wherein the humanized antibody is a human chimeric antibody or a human complementarity determining region (CDR)-grafted antibody comprising CDRs of VH and VL of a monoclonal antibody which specifically binds to FGF-8 to inhibit activity of FGF-8 and CH and CL of a human antibody,
   wherein the human CDR-grafted antibody is any of the following human CDR -grafted antibodies (a) to (c),
   (a) a human CDR-grafted antibody produced by transformant KM8037 (FERM BP-8084),
   (b) a human CDR-grafted antibody produced by transformant KM8035 (FERM BP-8082), and
   (c) a human CDR-grafted antibody produced by transformant KM8036 (FERM BP-8083).

* * * * *